United States Patent
Koide et al.

(10) Patent No.: US 11,459,400 B2
(45) Date of Patent: Oct. 4, 2022

(54) METHODS AND COMPOSITION FOR MODIFYING ENZYMES

(71) Applicant: The University of Chicago, Chicago, IL (US)

(72) Inventors: Shohei Koide, Chicago, IL (US); Shun-Ichi Tanaka, Chicago, IL (US); Akiko Koide, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 15/745,496

(22) PCT Filed: Jul. 15, 2016

(86) PCT No.: PCT/US2016/042516
§ 371 (c)(1),
(2) Date: Jan. 17, 2018

(87) PCT Pub. No.: WO2017/015119
PCT Pub. Date: Jan. 26, 2017

(65) Prior Publication Data
US 2018/0208678 A1 Jul. 26, 2018

Related U.S. Application Data

(60) Provisional application No. 62/193,955, filed on Jul. 17, 2015.

(51) Int. Cl.
| | |
|---|---|
| *G01N 33/53* | (2006.01) |
| *G01N 33/569* | (2006.01) |
| *G01N 33/573* | (2006.01) |
| *C07K 16/40* | (2006.01) |
| *C12Q 1/26* | (2006.01) |
| *C12Q 1/34* | (2006.01) |
| *C12Q 1/48* | (2006.01) |
| *C12Q 1/527* | (2006.01) |
| *C12Q 1/533* | (2006.01) |
| *C12Q 1/00* | (2006.01) |
| *C12N 9/38* | (2006.01) |
| *C07K 14/78* | (2006.01) |
| *C12N 9/20* | (2006.01) |
| *C12Q 1/25* | (2006.01) |
| *G01N 33/58* | (2006.01) |
| *G01N 33/60* | (2006.01) |

(52) U.S. Cl.
CPC .............. *C07K 16/40* (2013.01); *C07K 14/78* (2013.01); *C12N 9/20* (2013.01); *C12N 9/2471* (2013.01); *C12Q 1/00* (2013.01); *C12Q 1/25* (2013.01); *C12Q 1/26* (2013.01); *C12Q 1/34* (2013.01); *C12Q 1/48* (2013.01); *C12Q 1/527* (2013.01); *C12Q 1/533* (2013.01); *G01N 33/573* (2013.01); *G01N 33/582* (2013.01); *G01N 33/60* (2013.01); *C07K 2317/70* (2013.01); *C07K 2317/76* (2013.01); *C07K 2317/92* (2013.01); *C07K 2318/20* (2013.01); *C07K 2319/00* (2013.01); *C07K 2319/01* (2013.01); *C07K 2319/20* (2013.01); *C12Y 101/01001* (2013.01); *C12Y 301/01003* (2013.01); *C12Y 302/01023* (2013.01)

(58) Field of Classification Search
CPC ........................................................ C07K 16/40
See application file for complete search history.

(56) References Cited

U.S. PATENT DOCUMENTS

| | | |
|---|---|---|
| 6,673,901 B2 | 1/2004 | Koide |
| 2010/0311094 A1 | 12/2010 | Mui et al. |
| 2014/0377776 A1 | 12/2014 | Salafsky |

FOREIGN PATENT DOCUMENTS

| | | | |
|---|---|---|---|
| WO | WO 2004/039845 | | 5/2004 |
| WO | WO 2008/031098 | * | 3/2008 |
| WO | WO 2010/028214 | | 3/2010 |
| WO | WO 2010/028214 A2 | * | 3/2010 |

OTHER PUBLICATIONS

Bowie et al. (Science, 1990, 247:1306-1310) (Year: 1990).*
Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000,10:398-400) (Year: 2000).*
Bornscheuer et al., "Engineering the third wave of biocatalysis" *Nature*, 2012, 485:185-194.
Chen et al., "Enzyme engineering for nonaqueous solvents: random mutagenesis to enhance activity of subtilisin E in polar organic media." *Biotechnology* (N.Y.), 1991, 9:1073-1077.

(Continued)

*Primary Examiner* — Gary B Nickol
*Assistant Examiner* — Lakia J Jackson-Tongue
(74) *Attorney, Agent, or Firm* — Norton Rose Fulbright US LLP

(57) ABSTRACT

Aspects of the disclosure relate to compositions of enzyme-binding polypeptides (EBPs) that modify the substrate specificity of an enzyme and a method for identifying an EBP that modifies substrate specificity of an enzyme binding at least one substrate, the method comprising: contacting the enzyme with a polypeptide library comprising a plurality of EBPs that bind different epitopes of the enzyme; identifying EBPs that bind to the enzyme to form an EBP-enzyme complex; assaying for the activity level and substrate specificity of the EBP-enzyme complex; and identifying EBPs that modify the substrate specificity of the enzyme by identifying EBPs that, when in an EBP-enzyme complex, have a different substrate specificity than un-complexed EBP; wherein the catalytic rate constant of the EBP-enzyme complex is ≥50% of the un-complexed enzyme for at least one substrate and/or wherein the EBP-enzyme complex retains binding to a substrate.

14 Claims, 14 Drawing Sheets
Specification includes a Sequence Listing.

(56) References Cited

OTHER PUBLICATIONS

Chen-Goodspeed et al., "Enhancements, Relaxation and Reversal of the Stereoselectivity for Phosphotriesterase by Rational Evolution of Active Site Residues", *Biochemistry*, 2001, 40:1332-1339.

Davids et al., "Strategies for the discovery and engineering of enzymes for biocatalysis" *Curr. Opin. Chem. Biol.*, 2013, 17:215-220.

Erickson, "Stretching fibronectin" *J. Muscle Res. Cell Motility*, 2002, 23(5-6):575-580.

Gilbreth et al., "A Dominant Conformational Role for Amino Acid Diversity in Minimalist Protein-Protein Interfaces" *J. Mol. Biol.*, 2008, 3 81:407-418.

Gilbreth et al., "Isoform-specific monobody inhibitors of small ubiquitin-related modifiers engineered using structure-guided library design" *Proc Natl. Acad. Sci. U.S.A.*, 2011, 108:7751-7756.

Goldsmith et al., "Directed enzyme evolution: beyond the low-hanging fruit" *Curr. Opin. Struct. Biol.*, 2012, 22:406-412.

Grebien et al., "Targeting the SH2-Kinase Interface in Bcr-Abl Inhibits Leukemogenesis" *Cell*, 2011, 147:306-319.

International Search Report and Written Opinion issued in International Patent Application No. PCT/US16/42516, dated Dec. 27, 2016.

Koide et al., "High-affinity single-domain binding proteins with a binary-code interface" *Proc. Natl. Acad. Sci. U.S.A.*, 2007, 104:6632-6637.

Koide et al., "Teaching an old scaffold new tricks: Monobodies constructed using alternative surfaces of the FN3 scaffold" *J. Mol. Biol.*, 2012, 415:393-405.

Koide et al., "The fibronectin type III domain as a scaffold for novel binding proteins" *J. Molec. Biol.*, 1998,284:1141-1151.

Koide, "Monobodies: antibody mimics based on the scaffold of the fibronectin type III domain" *Methods Mol. Biol.*, 2007, 352:95-109.

Mak et al., "Computational enzyme design: transitioning from catalytic proteins to enzymes" *Curr. Opin. Struct. Biol.*, 2014, 27:87-94.

Pankov et al., "Fibronectin at a glance" *J. Cell Sci.*, 2002, 115(pt20):3861-3863.

Schmitt et al., "Blocking the tunnel: engineering of *Candida rugosa* lipase mutants with short chain length specificity" *Protein Eng.*, 2002, 15:595-601.

Sechler et al., "Modulatory Roles for Integrin Activation and the Synergy Site of Fibronectin during Matrix Assembly" *Molec. Biol. Cell.*, 1997, 8(12):2563-2573.

Sha et al., "Dissection of the BCR-ABL signaling network using highly specific monobody inhibitors to the SHP2 SH2 domains" *Proc Natl. Acad. Sci. U.S.A.*, 2013, 110:14924-14929.

Song et al., "Cloning and expression of a β-Galactosidase Gene of *Bacillus Circulans*" *Biosci. Biotechnol. Biochem.*, 2011, 75:1194-1197.

Van der Veen et al., "Rational design of cyclodextrin glycosyltransferase from *Bacillus circulans* strain 251 to increase α-cyclodextrin production" *J. Mol. Biol.*, 2000, 296:1027-1038.

Wilks et al., "A specific, highly active malate dehydrogenase by redesign of a lactate dehydrogenase framework" *Science*, 1988, 242:1541-1544.

Wojcik et al., "A potent and highly specific FN3 monobody inhibitor of the Abl SH2 domain" *Nat. Struct. Mol. Biol.*, 2010, 17:519-527.

Jacobs et al., "FN3 Domain Engineering", *Protein Engineering*, Kaumaya (Ed.), 2012.

Partial Supplemental Search Report and Provisional Opinion for EP16828310.9, dated Dec. 5, 2018.

Portnoff et al., "Ubiquibodies, Synthetic E3 Ubiquitin Ligases Endowed with Unnatural Substrate Specificity for Targeted Protein Silencing", *The Journal of Biological Chemistry* 289:11, 7844-7855, 2014.

* cited by examiner

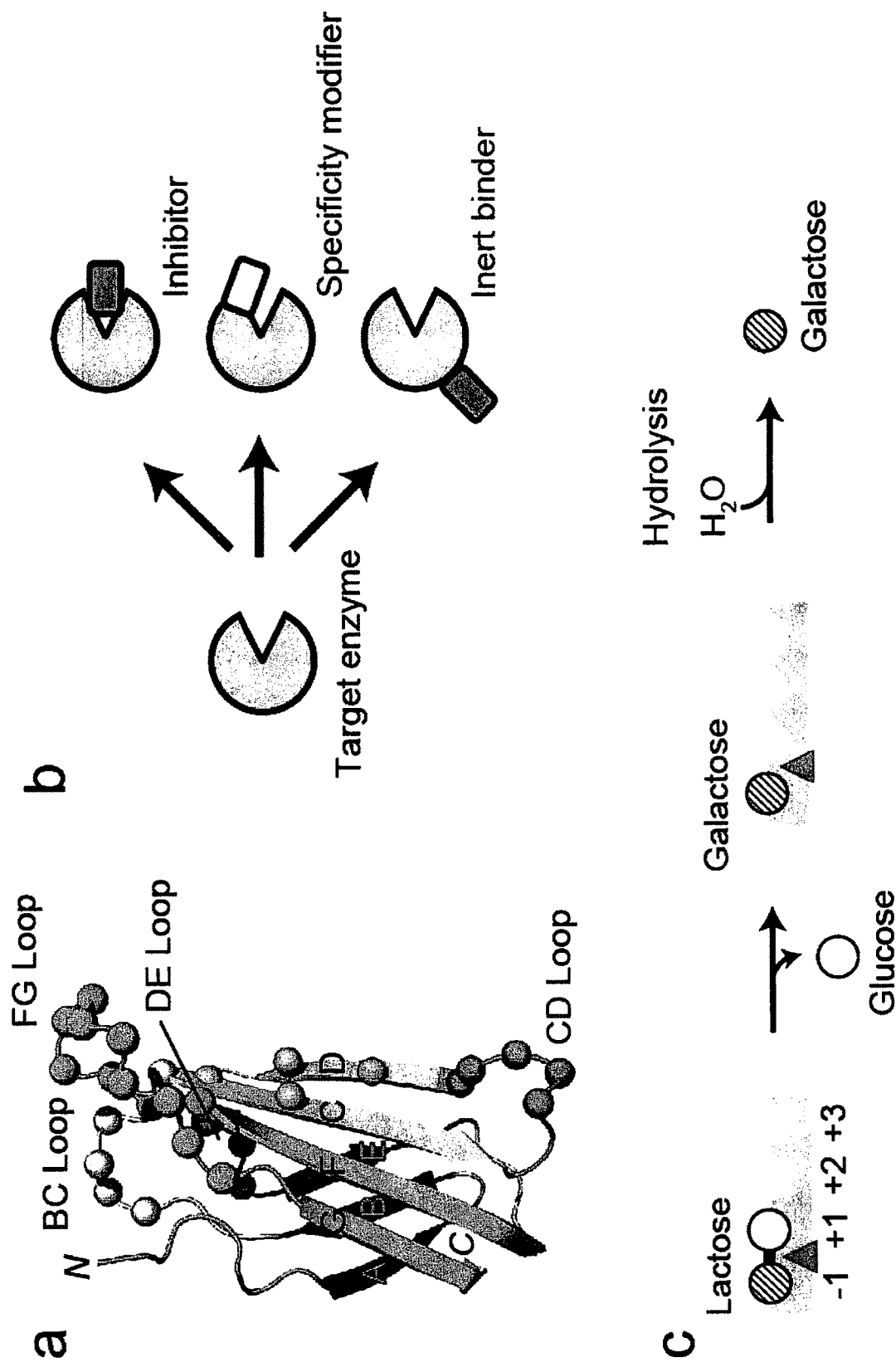
FIG. 1A-C

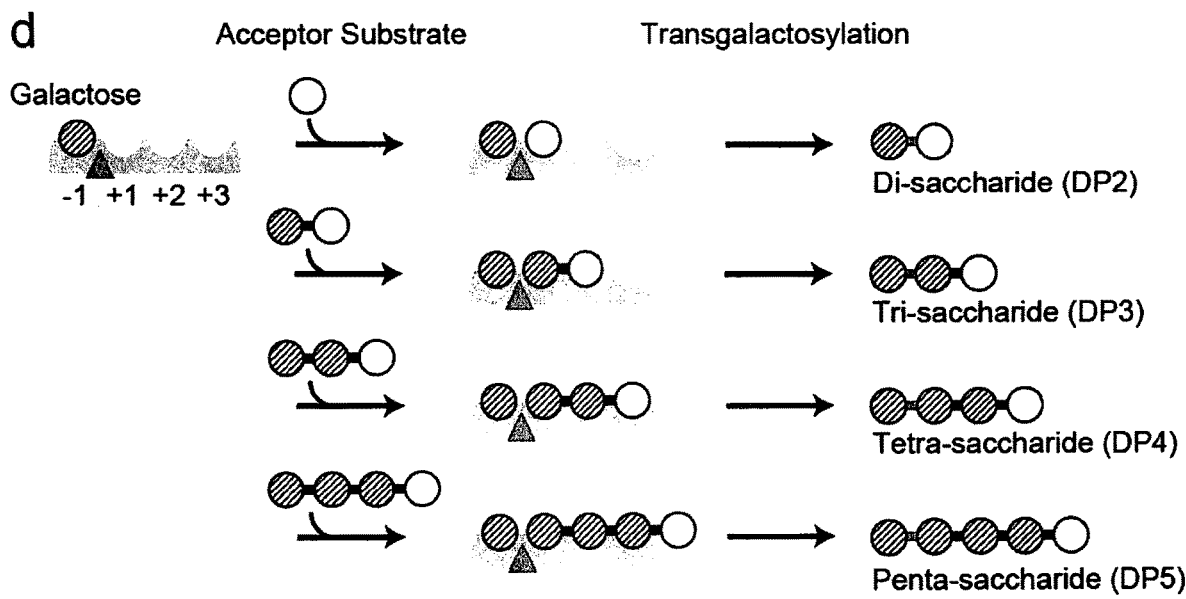
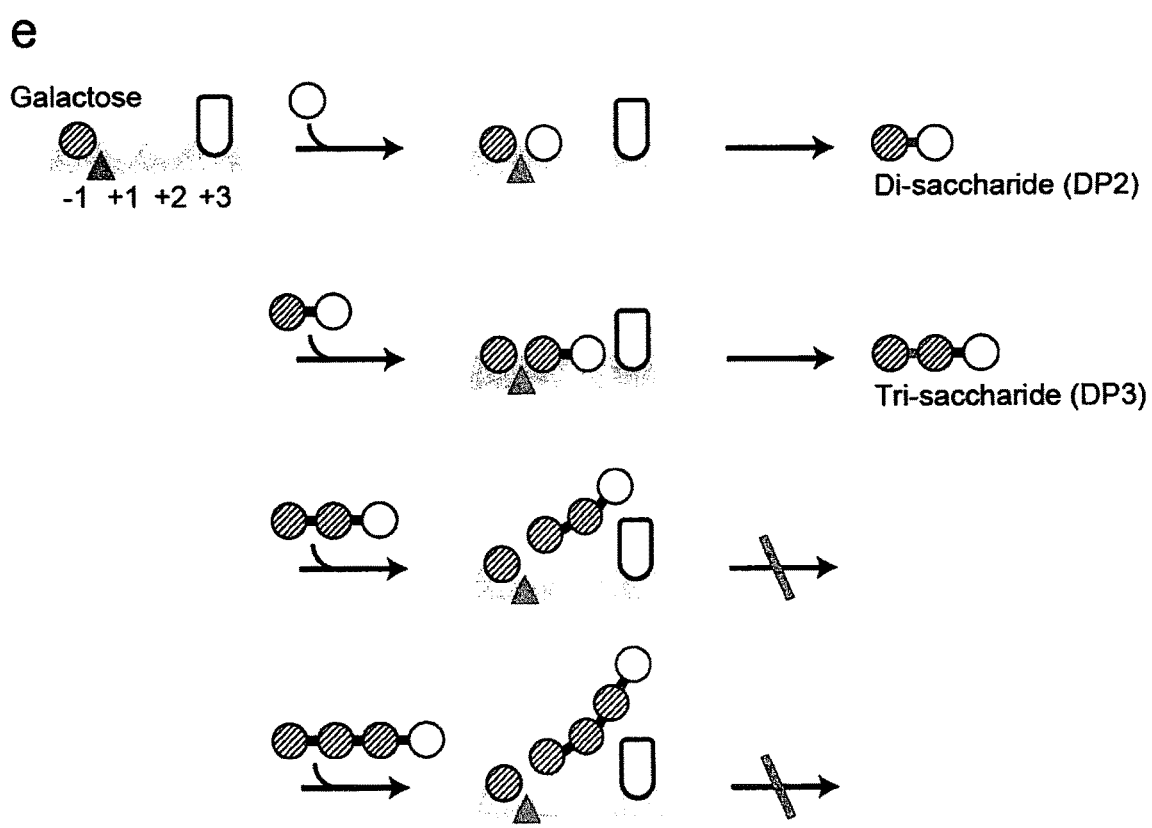
FIG. 1D-E

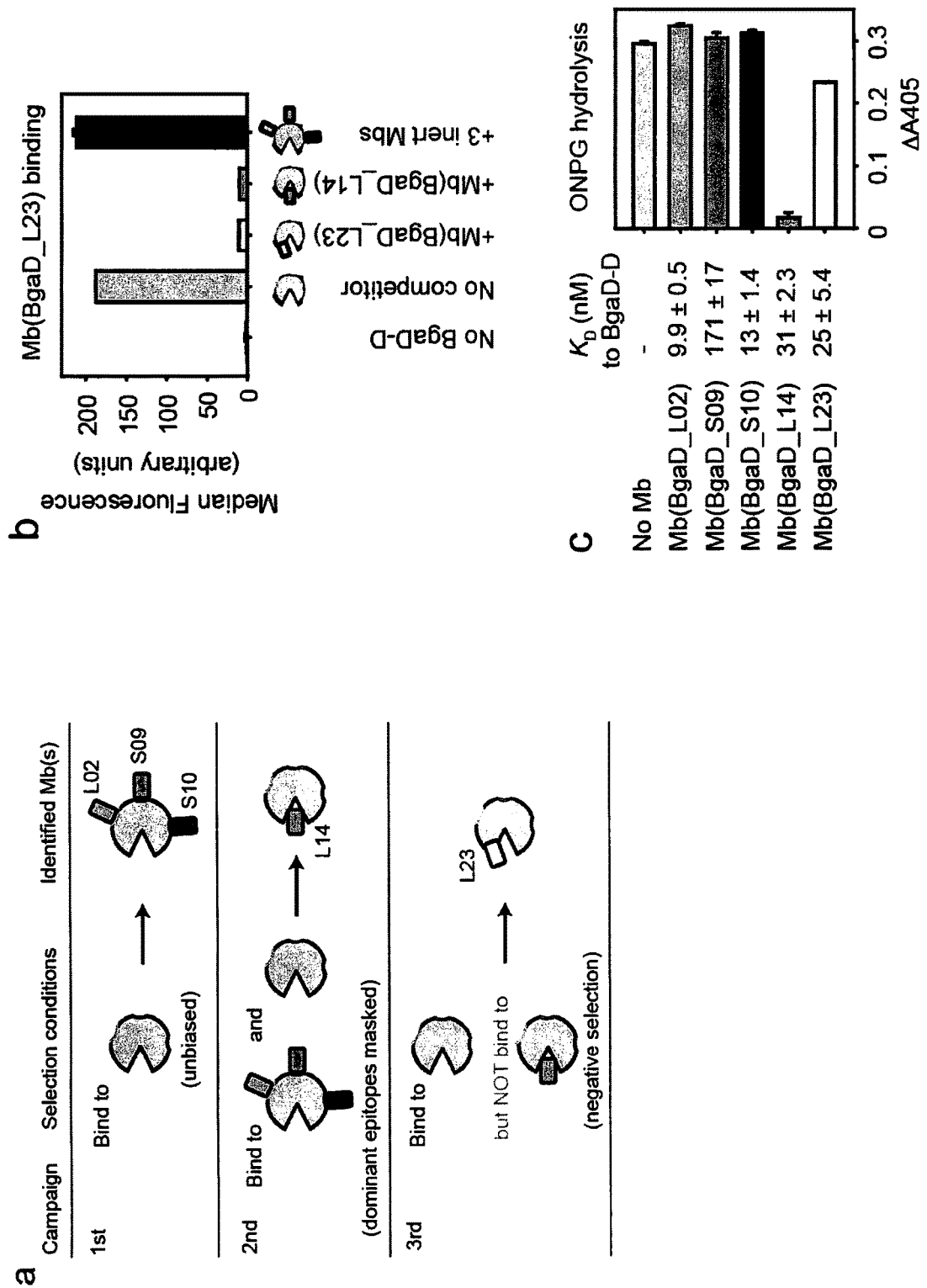
FIG. 2A-C

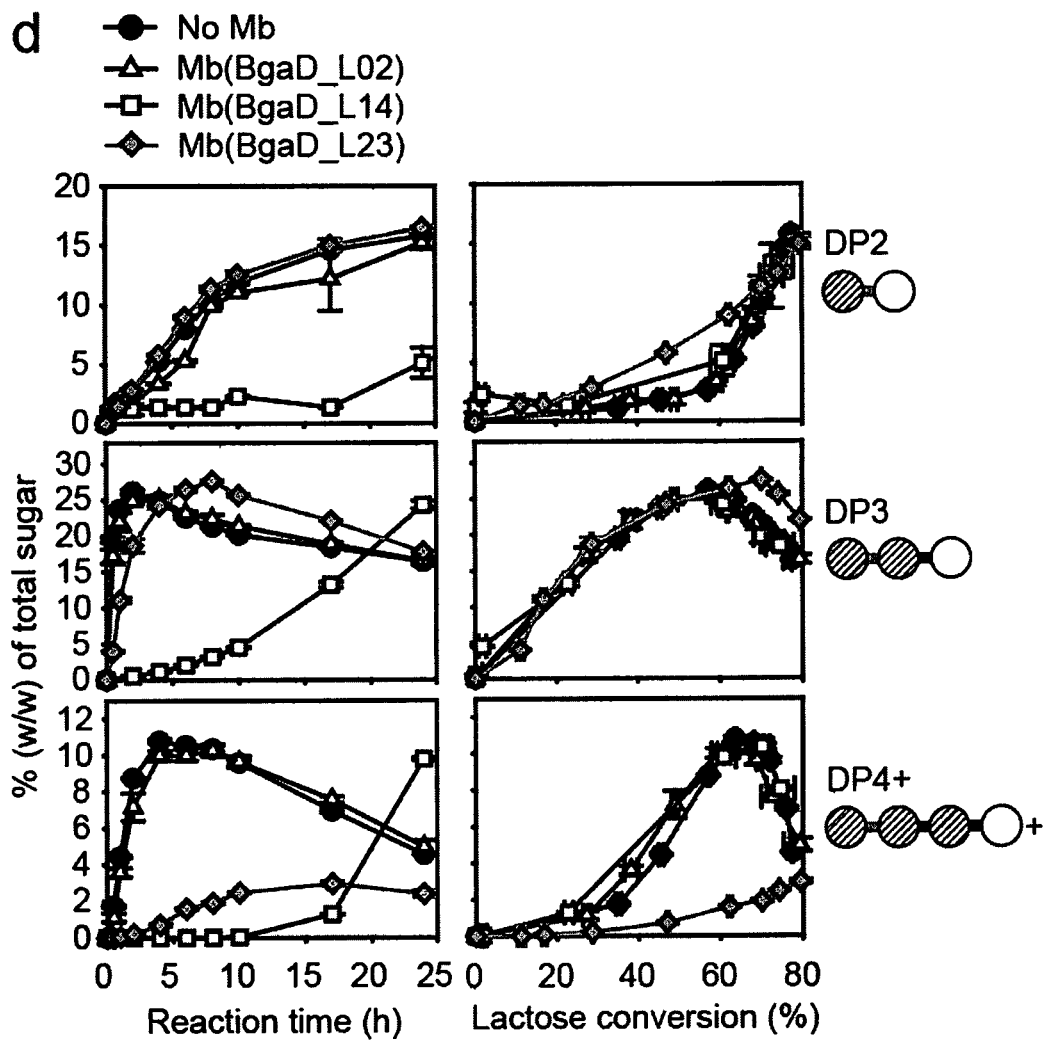
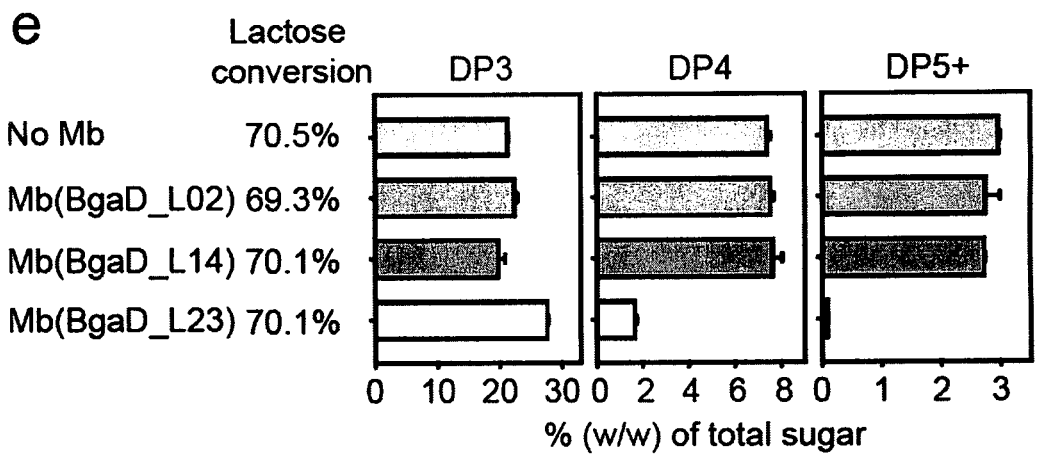
FIG. 2D-E

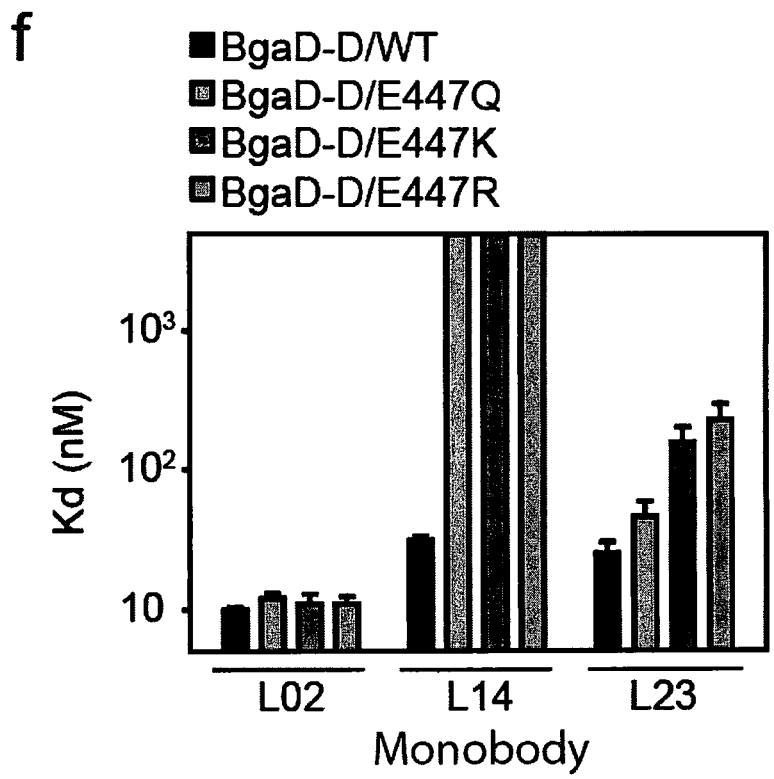
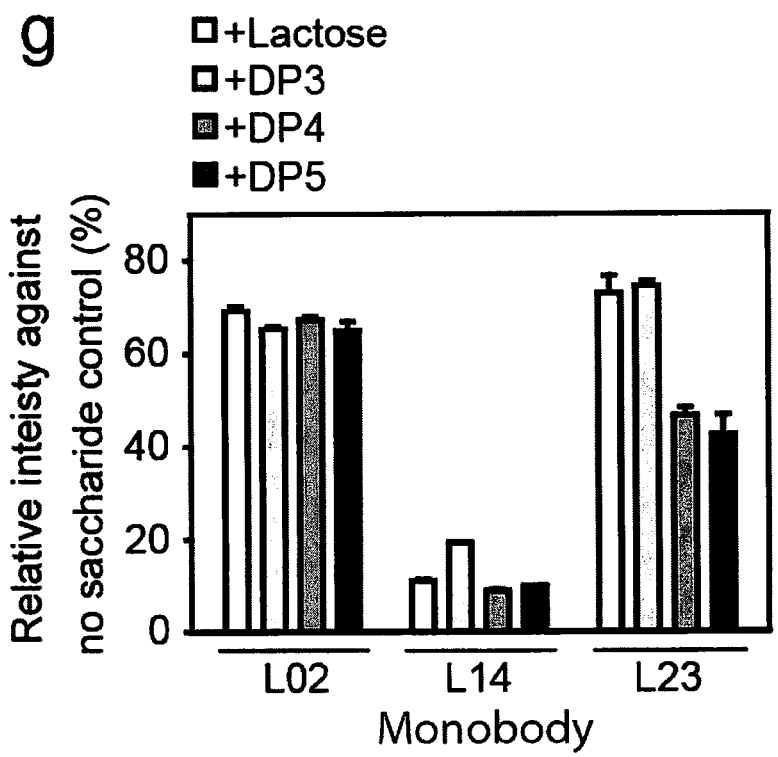
FIG. 2F-G

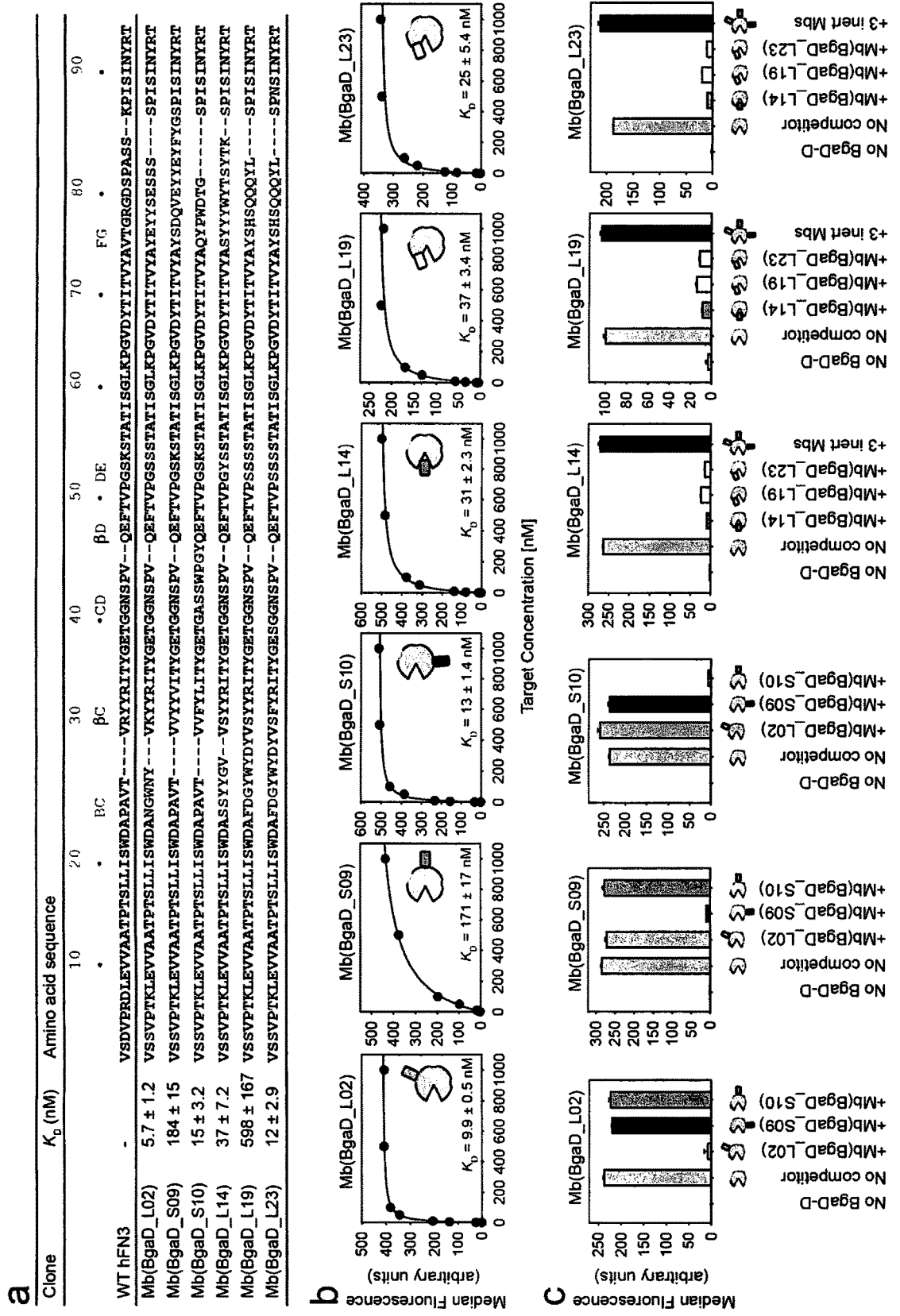
FIG. 3A-C

FIG. 9A-B

SEQUENCE LISTING

<160> NUMBER OF SEQ ID NOS: 117

<210> SEQ ID NO 1
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 1

Val Ser Ser Val Pro Thr Lys Leu Glu Val Val Ala Ala Thr Pro Thr
1               5                   10                  15

Ser Leu Leu Ile Ser Trp Asp Ala Met Asp His Thr Pro Tyr Val Tyr
            20                  25                  30

Tyr Tyr Arg Ile Thr Tyr Gly Glu Thr Gly Gly Asn Ser Pro Val Gln
        35                  40                  45

Glu Phe Thr Val Pro Gly Tyr Tyr Ser Thr Ala Thr Ile Ser Gly Leu
    50                  55                  60

Lys Pro Gly Val Asp Tyr Thr Ile Thr Val Tyr Ala Gly Asp Leu Ser
65                  70                  75                  80

Trp Asn Phe Asp Phe Tyr Ser Pro Ile Ser Ile Asn Tyr Arg Thr
                85                  90                  95

<210> SEQ ID NO 2
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 2

Val Ser Ser Val Pro Thr Lys Leu Glu Val Val Ala Ala Thr Pro Thr
1               5                   10                  15

Ser Leu Leu Ile Ser Trp Asp Ala Ile Phe Trp Ser Val Ala Tyr Tyr
            20                  25                  30

Arg Ile Thr Tyr Gly Glu Thr Gly Gly Asn Ser Pro Val Gln Glu Phe
        35                  40                  45

Thr Val Pro Gly Tyr Tyr Ser Thr Ala Thr Ile Ser Gly Leu Lys Pro
    50                  55                  60

Gly Val Asp Tyr Thr Ile Thr Val Tyr Ala Gly Asp Leu Ser Trp Asn
65                  70                  75                  80

Phe Asp Phe Tyr Ser Pro Ile Ser Ile Asn Tyr Arg Thr
            85                  90

<210> SEQ ID NO 3
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 3

Val Ser Ser Val Pro Thr Lys Leu Glu Val Val Ala Ala Thr Pro Thr
1               5                   10                  15

Ser Leu Leu Ile Ser Trp Asp Ala Gly Gln Ser Tyr Val Tyr Tyr Tyr
            20                  25                  30

Arg Ile Thr Tyr Gly Glu Thr Gly Gly Asn Ser Pro Val Gln Glu Phe
            35                  40                  45

Thr Val Pro Gly Tyr Tyr Ser Thr Ala Thr Ile Ser Gly Leu Lys Pro
    50                  55                  60

Gly Val Asp Tyr Thr Ile Thr Val Tyr Ala Gly Asp Leu Ser Trp Asn
65                  70                  75                  80

Phe Asp Phe Tyr Ser Pro Ile Ser Ile Asn Tyr Arg Thr
            85                  90

<210> SEQ ID NO 4
<211> LENGTH: 97
<212> TYPE: PRT
<213> ORGANISM: Artificial Sequence
<220> FEATURE:
<223> OTHER INFORMATION: Synthetic Peptide

<400> SEQUENCE: 4

Val Ser Ser Val Pro Thr Lys Leu Glu Val Val Ala Ala Thr Pro Thr
1               5                   10                  15

Ser Leu Leu Ile Ser Trp Asp Ala Tyr Phe Trp Gly Tyr Tyr Tyr Ser
            20                  25                  30

Val Trp Tyr Tyr Arg Ile Thr Tyr Gly Glu Thr Gly Gly Asn Ser Pro
            35                  40                  45

Val Gln Glu Phe Thr Val Pro Gly Tyr Ser Thr Ala Thr Ile Ser
    50                  55                  60

Gly Leu Lys Pro Gly Val Asp Tyr Thr Ile Thr Val Tyr Ala Ile Met
65                  70                  75                  80

Glu Ser Trp Tyr Tyr Gly Ser Tyr Ser Pro Ile Ser Ile Asn Tyr Arg
            85                  90                  95

Thr

<210> SEQ ID NO 5
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 5

Val Ser Ser Val Pro Thr Lys Leu Glu Val Val Ala Ala Thr Pro Thr
1               5                   10                  15

Ser Leu Leu Ile Ser Trp Asp Ala Gly Val Lys Gly Trp Asn Tyr Val
            20                  25                  30

Asp Tyr Tyr Arg Ile Thr Tyr Gly Glu Thr Gly Gly Asn Ser Pro Val

```
                35                  40                  45
Gln Glu Phe Thr Val Pro Gly Tyr Tyr Ser Thr Ala Thr Ile Ser Gly
    50                  55                  60

Leu Lys Pro Gly Val Asp Tyr Thr Ile Thr Val Tyr Ala Lys Gly Trp
65                  70                  75                  80

Tyr Gly Tyr Asp Tyr Ser Pro Ile Ser Ile Asn Tyr Arg Thr
                85                  90

<210> SEQ ID NO 6
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 6

Val Ser Ser Val Pro Thr Lys Leu Glu Val Val Ala Ala Thr Pro Thr
1               5                   10                  15

Ser Leu Leu Ile Ser Trp Asp Ala Asp Tyr Tyr Asn Val Met Tyr Tyr
                20                  25                  30

Arg Ile Thr Tyr Gly Glu Thr Gly Gly Asn Ser Pro Val Gln Glu Phe
                35                  40                  45

Thr Val Pro Gly Tyr Ser Ser Thr Ala Thr Ile Ser Gly Leu Lys Pro
    50                  55                  60

Gly Val Asp Tyr Thr Ile Thr Val Tyr Ala Gly Leu Tyr Asp Trp Gly
65                  70                  75                  80

Tyr Tyr His Ser Pro Ile Ser Ile Asn Tyr Arg Thr
                85                  90

<210> SEQ ID NO 7
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 7

Val Ser Ser Val Pro Thr Lys Leu Glu Val Val Ala Ala Thr Pro Thr
1               5                   10                  15

Ser Leu Leu Ile Ser Trp Asp Ala Pro Val Tyr Trp Asn His Val Asn
                20                  25                  30

Tyr Tyr Arg Ile Thr Tyr Gly Glu Thr Gly Gly Asn Ser Pro Val Gln
                35                  40                  45

Glu Phe Thr Val Pro Gly Tyr Tyr Ser Thr Ala Thr Ile Ser Gly Leu
    50                  55                  60

Lys Pro Gly Val Asp Tyr Thr Ile Thr Val Tyr Ala Gly Ser Phe His
65                  70                  75                  80

Tyr Pro Tyr Gln Glu Tyr Ser Pro Ile Ser Ile Asn Tyr Arg Thr
                85                  90                  95

<210> SEQ ID NO 8
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 8

Val Ser Ser Val Pro Thr Lys Leu Glu Val Val Ala Ala Thr Pro Thr
1               5                   10                  15
```

Ser Leu Leu Ile Ser Trp Asp Ala Asn Gly Trp Asn Tyr Val Lys Tyr
             20                  25                  30

Tyr Arg Ile Thr Tyr Gly Glu Thr Gly Gly Asn Ser Pro Val Gln Glu
         35                  40                  45

Phe Thr Val Pro Gly Ser Ser Thr Ala Thr Ile Ser Gly Leu Lys
 50                  55                  60

Pro Gly Val Asp Tyr Thr Ile Thr Val Tyr Ala Tyr Glu Tyr Tyr Ser
 65                  70                  75                  80

Glu Ser Ser Ser Pro Ile Ser Ile Asn Tyr Arg Thr
                 85                  90

<210> SEQ ID NO 9
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 9

Val Ser Ser Val Pro Thr Lys Leu Glu Val Val Ala Ala Thr Pro Thr
 1               5                  10                  15

Ser Leu Leu Ile Ser Trp Asp Ala Gln Gly Trp Asn Tyr Val Gln Tyr
             20                  25                  30

Tyr Arg Ile Thr Tyr Gly Glu Thr Gly Gly Asn Ser Pro Val Gln Glu
         35                  40                  45

Phe Thr Val Pro Gly Tyr Ser Ser Thr Ala Thr Ile Ser Gly Leu Lys
 50                  55                  60

Pro Gly Val Asp Tyr Thr Ile Thr Val Tyr Ala Tyr Glu Tyr Tyr Ser
 65                  70                  75                  80

Val Gly Tyr Glu Ser Pro Ile Ser Ile Asn Tyr Arg Thr
                 85                  90

<210> SEQ ID NO 10
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 10

Val Ser Ser Val Pro Thr Lys Leu Glu Val Val Ala Ala Thr Pro Thr
 1               5                  10                  15

Ser Leu Leu Ile Ser Trp Asp Ala Trp Ala Ser Phe Asn Tyr Val Ser
             20                  25                  30

Tyr Tyr Arg Ile Thr Tyr Gly Glu Thr Gly Gly Asn Ser Pro Val Gln
         35                  40                  45

Glu Phe Thr Val Pro Gly Tyr Ser Ser Thr Ala Thr Ile Ser Gly Leu
 50                  55                  60

Lys Pro Gly Val Asp Tyr Thr Ile Thr Val Tyr Ala Gln Glu Tyr Tyr
 65                  70                  75                  80

Arg Gly Thr Ser Tyr Ala Pro Ser Pro Ile Ser Ile Asn Tyr Arg Thr
                 85                  90                  95

<210> SEQ ID NO 11
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 11

Val Ser Ser Val Pro Thr Lys Leu Glu Val Val Ala Ala Thr Pro Thr
1               5                   10                  15

Ser Leu Leu Ile Ser Trp Asp Ala Ser Gly Trp Asn Tyr Val Ser Tyr
            20                  25                  30

Tyr Arg Ile Thr Tyr Gly Glu Thr Gly Gly Asn Ser Pro Val Gln Glu
        35                  40                  45

Phe Thr Val Pro Gly Tyr Ser Ser Thr Ala Thr Ile Ser Gly Leu Lys
    50                  55                  60

Pro Gly Val Asp Tyr Thr Ile Thr Val Tyr Ala Tyr Glu Phe Tyr Ser
65                  70                  75                  80

Ser Tyr Gly Ser Pro Ile Ser Ile Asn Tyr Arg Thr
                85                  90

<210> SEQ ID NO 12
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 12

Val Ser Ser Val Pro Thr Lys Leu Glu Val Val Ala Ala Thr Pro Thr
1               5                   10                  15

Ser Leu Leu Ile Ser Trp Asp Ala Tyr Gly Trp Asn Tyr Val Ser Tyr
            20                  25                  30

Tyr Arg Ile Thr Tyr Gly Glu Thr Gly Gly Asn Ser Pro Val Gln Glu
        35                  40                  45

Phe Thr Val Pro Gly Ser Ser Ser Thr Ala Thr Ile Ser Gly Leu Lys
    50                  55                  60

Pro Gly Val Asp Tyr Thr Ile Thr Val Tyr Ala Tyr Glu Phe Tyr Ser
65                  70                  75                  80

Ser Tyr Gly Ser Pro Ile Ser Ile Asn Tyr Arg Thr
                85                  90

<210> SEQ ID NO 13
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 13

Val Ser Ser Val Pro Thr Lys Leu Glu Val Val Ala Ala Thr Pro Thr
1               5                   10                  15

Ser Leu Leu Ile Ser Trp Asp Ala Trp Ala Ser Phe Asn Tyr Val Ser
            20                  25                  30

Tyr Tyr Arg Ile Thr Tyr Gly Glu Thr Gly Gly Asn Ser Pro Val Gln
        35                  40                  45

Glu Phe Thr Val Pro Gly Tyr Ser Ser Thr Ala Thr Ile Ser Gly Leu
    50                  55                  60

Lys Pro Gly Val Asp Tyr Thr Ile Thr Val Tyr Ala Tyr Glu Phe Tyr
65                  70                  75                  80

Ser Ser Tyr Gly Ser Pro Ile Ser Ile Asn Tyr Arg Thr
                85                  90

<210> SEQ ID NO 14

<211> LENGTH: 93
<212> TYPE: PRT
<213> ORGANISM: Artificial Sequence
<220> FEATURE:
<223> OTHER INFORMATION: Synthetic Peptide

<400> SEQUENCE: 14

Val Ser Ser Val Pro Thr Lys Leu Glu Val Val Ala Ala Thr Pro Thr
1               5                   10                  15

Ser Leu Leu Ile Ser Trp Asp Ala Gly Asp Tyr Trp Val Tyr Tyr Tyr
            20                  25                  30

Arg Ile Thr Tyr Gly Glu Thr Gly Gly Asn Ser Pro Val Gln Glu Phe
        35                  40                  45

Thr Val Pro Gly Tyr Ser Ser Thr Ala Thr Ile Ser Gly Leu Lys Pro
    50                  55                  60

Gly Val Asp Tyr Thr Ile Thr Val Tyr Ala Gly Asp Leu Ser Phe Asn
65                  70                  75                  80

Thr Tyr Tyr Tyr Ser Pro Ile Ser Ile Asn Tyr Arg Thr
                85                  90

<210> SEQ ID NO 15
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 15

Val Ser Ser Val Pro Thr Lys Leu Glu Val Val Ala Ala Thr Pro Thr
1               5                   10                  15

Ser Leu Leu Ile Ser Trp Asp Ala Gln Gly Tyr Pro Val Tyr Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Ser Thr Ala Thr Ile Ser Gly Leu Lys Pro
    50                  55                  60

Gly Val Asp Tyr Thr Ile Thr Val Tyr Ala Gly Asp Leu Ser Phe Asn
65                  70                  75                  80

Thr Tyr Tyr Tyr Ser Pro Ile Ser Ile Asn Tyr Arg Thr
                85                  90

<210> SEQ ID NO 16
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 16

Val Ser Ser Val Pro Thr Lys Leu Glu Val Val Ala Ala Thr Pro Thr
1               5                   10                  15

Ser Leu Leu Ile Ser Trp Asp Ala Tyr Tyr Gly Asp Val Tyr Tyr Tyr
            20                  25                  30

Arg Ile Thr Tyr Gly Glu Thr Gly Gly Asn Ser Pro Val Gln Glu Phe
        35                  40                  45

Thr Val Pro Gly Tyr Ser Ser Thr Ala Thr Ile Ser Gly Leu Lys Pro
    50                  55                  60

Gly Val Asp Tyr Thr Ile Thr Val Tyr Ala Gly Asp Leu Ser Phe Asn
65                  70                  75                  80

Thr Tyr Tyr Tyr Ser Pro Ile Ser Ile Asn Tyr Arg Thr
                85                  90

<210> SEQ ID NO 17
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 17

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Ser Thr Ala Thr Ile Ser Gly Leu Lys Pro
        50                  55                  60

Gly Val Asp Tyr Thr Ile Thr Val Tyr Ala Gly Asp Ile Ala Phe Asn
65                  70                  75                  80

Trp Tyr Tyr Tyr Ser Pro Ile Ser Ile Asn Tyr Arg Thr
                85                  90

<210> SEQ ID NO 18
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 18

Val Ser Ser Val Pro Thr Lys Leu Glu Val Val Ala Ala Thr Pro Thr
1               5                   10                  15

Ser Leu Leu Ile Ser Trp Asp Ala Trp Arg Gly Glu Gly Val Ala Tyr
            20                  25                  30

Tyr Arg Ile Thr Tyr Gly Glu Thr Gly Gly Asn Ser Pro Val Gln Glu
            35                  40                  45

Phe Thr Val Pro Gly Ser Ser Ser Thr Ala Thr Ile Ser Gly Leu Lys
        50                  55                  60

Pro Gly Val Asp Tyr Thr Ile Thr Val Tyr Ala Gly Asp Ile Ala Phe
65                  70                  75                  80

Asn Trp Tyr Tyr Tyr Ser Pro Ile Ser Ile Asn Tyr Arg Thr
                85                  90

<210> SEQ ID NO 19
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 19

Val Ser Ser Val Pro Thr Lys Leu Glu Val Val Ala Ala Thr Pro Thr
1               5                   10                  15

Ser Leu Leu Ile Ser Trp Asp Ala Tyr Tyr Pro Ser Trp Gly Val Ser
            20                  25                  30

Tyr Tyr Arg Ile Thr Tyr Gly Glu Thr Gly Gly Asn Ser Pro Val Gln
            35                  40                  45

Glu Phe Thr Val Pro Gly Ser Ser Tyr Thr Ala Thr Ile Ser Gly Leu

```
                    50                  55                  60
Lys Pro Gly Val Asp Tyr Thr Ile Thr Val Tyr Ala Gly Asp Ile Ala
 65                  70                  75                  80

Phe Asn Trp Tyr Tyr Tyr Ser Pro Ile Ser Ile Asn Tyr Arg Thr
                 85                  90                  95

<210> SEQ ID NO 20
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 20

Val Ser Ser Val Pro Thr Lys Leu Glu Val Val Ala Ala Thr Pro Thr
 1               5                  10                  15

Ser Leu Leu Ile Ser Trp Asp Ala Tyr Ser Tyr Pro Val Ser Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Ser Thr Ala Thr Ile Ser Gly Leu Lys Pro
                 50                  55                  60

Gly Val Asp Tyr Thr Ile Thr Val Tyr Ala Gly Asp Ile Ala Phe Asn
 65                  70                  75                  80

Trp Tyr Tyr Tyr Ser Pro Ile Ser Ile Asn Tyr Arg Thr
                 85                  90

<210> SEQ ID NO 21
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 21

Val Ser Ser Val Pro Thr Lys Leu Glu Val Val Ala Ala Thr Pro Thr
 1               5                  10                  15

Ser Leu Leu Ile Ser Trp Asp Ala Tyr Glu His Trp Ser Gly Val Tyr
                20                  25                  30

Tyr Tyr Arg Ile Thr Tyr Gly Glu Thr Gly Gly Asn Ser Pro Val Gln
                35                  40                  45

Glu Phe Thr Val Pro Gly Tyr Ser Ser Thr Ala Thr Ile Ser Gly Leu
                50                  55                  60

Lys Pro Gly Val Asp Tyr Thr Ile Thr Val Tyr Ala Tyr Ser Tyr Ser
 65                  70                  75                  80

Tyr Ala Ser Met Tyr Ser Pro Ile Ser Ile Asn Tyr Arg Thr
                 85                  90

<210> SEQ ID NO 22
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 22

Val Ser Ser Val Pro Thr Lys Leu Glu Val Val Ala Ala Thr Pro Thr
 1               5                  10                  15

Ser Leu Leu Ile Ser Trp Asp Ala Tyr Glu His Trp Ser Gly Val Tyr
                20                  25                  30
```

Tyr Tyr Arg Ile Thr Tyr Gly Glu Thr Gly Gly Asn Ser Pro Val Gln
            35                  40                  45

Glu Phe Thr Val Pro Ser Tyr Ser Ser Thr Ala Thr Ile Ser Gly Leu
 50                  55                  60

Lys Pro Gly Val Asp Tyr Thr Ile Thr Val Tyr Ala Tyr Ser Tyr Ser
 65                  70                  75                  80

Tyr Ala Ser Met Tyr Ser Pro Ile Ser Ile Asn Tyr Arg Thr
                 85                  90

<210> SEQ ID NO 23
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 23

Val Ser Ser Val Pro Thr Lys Leu Glu Val Val Ala Ala Thr Pro Thr
 1               5                  10                  15

Ser Leu Leu Ile Ser Trp Asp Ala Tyr Glu His Trp Ser Gly Val Tyr
                20                  25                  30

Tyr Tyr Arg Ile Thr Tyr Gly Glu Thr Gly Gly Asn Ser Pro Val Gln
            35                  40                  45

Glu Phe Thr Val Pro Gly Ser Ser Thr Ala Thr Ile Ser Gly Leu
 50                  55                  60

Lys Pro Gly Val Asp Tyr Thr Ile Thr Val Tyr Ala Tyr Ser Tyr Ser
 65                  70                  75                  80

Tyr Ala Ser Met Tyr Ser Pro Ile Ser Ile Asn Tyr Arg Thr
                 85                  90

<210> SEQ ID NO 24
<211> LENGTH: 98
<212> TYPE: PRT
<213> ORGANISM: Artificial Sequence
<220> FEATURE:
<223> OTHER INFORMATION: Synthetic Peptide

<400> SEQUENCE: 24

Val Ser Ser Val Pro Thr Lys Leu Glu Val Val Ala Ala Thr Pro Thr
 1               5                  10                  15

Ser Leu Leu Ile Ser Trp Asp Ala Tyr Val Tyr Gln Ser Ser Ser Asp
                20                  25                  30

Val Tyr Tyr Tyr Arg Ile Thr Tyr Gly Glu Thr Gly Gly Asn Ser Pro
            35                  40                  45

Val Gln Glu Phe Thr Val Pro Gly Ser Ser Ser Thr Ala Thr Ile Ser
 50                  55                  60

Gly Leu Lys Pro Gly Val Asp Tyr Thr Ile Thr Val Tyr Ala Tyr Gly
 65                  70                  75                  80

Trp Trp Gly Ser Tyr Tyr Ser Phe Ala Ser Pro Ile Ser Ile Asn Tyr
                 85                  90                  95

Arg Thr

<210> SEQ ID NO 25
<211> LENGTH: 93
<212> TYPE: PRT
<213> ORGANISM: Artificial Sequence
<220> FEATURE:
<223> OTHER INFORMATION: Synthetic Peptide

```
<400> SEQUENCE: 25

Val Ser Ser Val Pro Thr Lys Leu Glu Val Val Ala Ala Thr Pro Thr
1               5                   10                  15

Ser Leu Leu Ile Ser Trp Asp Ala Tyr Tyr Ser Tyr Pro Tyr Tyr Val
                20                  25                  30

Ser Tyr Tyr Arg Ile Thr Tyr Gly Glu Thr Gly Gly Asn Ser Pro Val
                35                  40                  45

Gln Glu Phe Thr Val Pro Gly Ser Ser Thr Ala Thr Ile Ser Gly
        50                  55                  60

Leu Lys Pro Gly Val Asp Tyr Thr Ile Thr Val Tyr Ala Tyr Asp Asp
65                  70                  75                  80

Trp Gly Trp Thr Ser Pro Ile Ser Ile Asn Tyr Arg Thr
                85                  90

<210> SEQ ID NO 26
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 26

Val Ser Ser Val Pro Thr Lys Leu Glu Val Val Ala Ala Thr Pro Thr
1               5                   10                  15

Ser Leu Leu Ile Ser Trp Asp Ala Tyr Lys Ser Leu Gly Gly Val Asp
                20                  25                  30

Tyr Tyr Arg Ile Thr Tyr Gly Glu Thr Gly Gly Asn Ser Pro Val Gln
                35                  40                  45

Glu Phe Thr Val Pro Gly Ser Ser Ser Thr Ala Thr Ile Ser Gly Leu
        50                  55                  60

Lys Pro Gly Val Asp Tyr Thr Ile Thr Val Tyr Ala Gly Tyr Leu Trp
65                  70                  75                  80

Tyr Pro Tyr Gly Glu Trp Ser Pro Ile Ser Ile Asn Tyr Arg Thr
                85                  90                  95

<210> SEQ ID NO 27
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 27

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Tyr Tyr
                20                  25                  30

Ile Ile Thr Tyr Gly Glu Thr Gly Ala Ala Val Trp Pro Gly His Gln
                35                  40                  45

Glu Phe Thr Val Pro Gly Ser Lys Ser Thr Ala Thr Ile Ser Gly Leu
        50                  55                  60

Lys Pro Gly Val Asp Tyr Thr Ile Thr Val Tyr Ala Val Gly Pro Trp
65                  70                  75                  80

Asp Tyr Tyr Ser Pro Ile Ser Ile Asn Tyr Arg Thr
                85                  90

<210> SEQ ID NO 28
<211> LENGTH: 92
```

```
<212> TYPE: PRT
<213> ORGANISM: Artificial Sequence
<220> FEATURE:
<223> OTHER INFORMATION: Synthetic Peptide

<400> SEQUENCE: 28

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Tyr Tyr
                20                  25                  30

His Ile Thr Tyr Gly Glu Thr Gly Ala Ala Val Trp Pro Gly His Gln
            35                  40                  45

Glu Phe Thr Val Pro Gly Ser Lys Ser Thr Ala Thr Ile Ser Gly Leu
        50                  55                  60

Lys Pro Gly Val Asp Tyr Thr Ile Thr Val Tyr Ala Gln Gly Pro Trp
65                  70                  75                  80

Val Gly Tyr Ser Pro Ile Ser Ile Asn Tyr Arg Thr
                85                  90

<210> SEQ ID NO 29
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 29

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Tyr Tyr
                20                  25                  30

His Ile Thr Tyr Gly Glu Thr Gly Ala Ala Val Trp Pro Gly His Gln
            35                  40                  45

Glu Phe Thr Val Pro Gly Ser Lys Ser Thr Ala Thr Ile Ser Gly Leu
        50                  55                  60

Lys Pro Gly Val Asp Tyr Thr Ile Thr Val Tyr Ala Gln Ser Gly Trp
65                  70                  75                  80

Tyr Arg Tyr Ser Pro Ile Ser Ile Asn Tyr Arg Thr
                85                  90

<210> SEQ ID NO 30
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 30

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Phe Tyr
                20                  25                  30

Val Ile Thr Tyr Gly Glu Thr Gly Ala Ala Val Trp Pro Gly His Gln
            35                  40                  45

Glu Phe Thr Val Pro Gly Ser Lys Ser Thr Ala Thr Ile Ser Gly Leu
        50                  55                  60

Lys Pro Gly Val Asp Tyr Thr Ile Thr Val Tyr Ala Gln Gly Gly Arg
65                  70                  75                  80

Trp Lys Ser Ser Pro Ile Ser Ile Asn Tyr Arg Thr
```

<210> SEQ ID NO 31
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 31

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Phe Tyr
            20                  25                  30

Val Ile Thr Tyr Gly Glu Thr Gly Ala Ala Val Trp Pro Gly Tyr Gln
        35                  40                  45

Glu Phe Thr Val Pro Gly Ser Lys Ser Thr Ala Thr Ile Ser Gly Leu
    50                  55                  60

Lys Pro Gly Val Asp Tyr Thr Ile Thr Val Tyr Ala Gln His Pro Trp
65                  70                  75                  80

Met Glu Ser Ser Pro Ile Ser Ile Asn Tyr Arg Thr
                85                  90

<210> SEQ ID NO 32
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 32

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Phe Tyr
            20                  25                  30

Val Ile Thr Tyr Gly Glu Thr Gly Ala Val Trp Pro Gly Tyr Gln Glu
        35                  40                  45

Phe Thr Val Pro Gly Ser Lys Ser Thr Ala Thr Ile Ser Gly Leu Lys
    50                  55                  60

Pro Gly Val Asp Tyr Thr Ile Thr Val Tyr Ala Gln Ser Pro Phe Trp
65                  70                  75                  80

Val Trp Ser Pro Ile Ser Ile Asn Tyr Arg Thr
                85                  90

<210> SEQ ID NO 33
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 33

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

Leu Ile Thr Tyr Gly Glu Thr Gly His Ser Ala Ala Trp Pro Gln Ala
        35                  40                  45

Phe Thr Val Pro Gly Ser Lys Ser Thr Ala Thr Ile Ser Gly Leu Lys
    50                  55                  60

Pro Gly Val Asp Tyr Thr Ile Thr Val Tyr Ala Gln Gly Gln Tyr Tyr
65                  70                  75                  80

Gln Tyr Ser Pro Ile Ser Ile Asn Tyr Arg Thr
            85                  90

<210> SEQ ID NO 34
<211> LENGTH: 90
<212> TYPE: PRT
<213> ORGANISM: Artificial Sequence
<220> FEATURE:
<223> OTHER INFORMATION: Synthetic Peptide

<400> SEQUENCE: 34

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

Val Ile Thr Tyr Gly Glu Thr Gly Gly Ser Gly Trp Pro Gln Ala Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Gln Gly Ser Phe Tyr Ser
65                  70                  75                  80

Tyr Ser Pro Ile Ser Ile Asn Tyr Arg Thr
            85                  90

<210> SEQ ID NO 35
<211> LENGTH: 90
<212> TYPE: PRT
<213> ORGANISM: Artificial Sequence
<220> FEATURE:
<223> OTHER INFORMATION: Synthetic Peptide

<400> SEQUENCE: 35

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

Val Ile Thr Tyr Gly Glu Thr Gly Gly Pro Gly Trp Pro Gln Thr Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Gln Gly Pro His Met Leu
65                  70                  75                  80

Tyr Ser Pro Ile Ser Ile Asn Tyr Arg Thr
            85                  90

<210> SEQ ID NO 36
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 36

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Tyr Tyr
            20                  25                  30

Val Ile Thr Tyr Gly Glu Thr Gly His His Trp Pro Gly Tyr Gln Glu
            35                  40                  45

Phe Thr Val Pro Gly Ser Lys Ser Thr Ala Thr Ile Ser Gly Leu Lys
     50                  55                  60

Pro Gly Val Asp Tyr Thr Ile Thr Val Tyr Ala Gln Gly Pro Trp Tyr
65                  70                  75                  80

Ser Tyr Ser Pro Ile Ser Ile Asn Tyr Arg Thr
                85                  90

<210> SEQ ID NO 37
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 37

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Tyr Tyr
            20                  25                  30

Val Ile Thr Tyr Gly Glu Thr Gly Ala Ser Ser Trp Pro Gly Tyr Gln
            35                  40                  45

Glu Phe Thr Val Pro Gly Ser Lys Ser Thr Ala Thr Ile Ser Gly Leu
     50                  55                  60

Lys Pro Gly Val Asp Tyr Thr Ile Thr Val Tyr Ala Gln Gly Pro Phe
65                  70                  75                  80

Val Ser Tyr Ser Pro Ile Ser Ile Asn Tyr Arg Thr
                85                  90

<210> SEQ ID NO 38
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 38

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

Leu Ile Thr Tyr Gly Glu Thr Gly Phe Ser Tyr Gly Phe Pro Gln Ala
            35                  40                  45

Phe Thr Val Pro Gly Ser Lys Ser Thr Ala Thr Ile Ser Gly Leu Lys
     50                  55                  60

Pro Gly Val Asp Tyr Thr Ile Thr Val Tyr Ala Ser Thr Val Asp Gly
65                  70                  75                  80

His Ser Ser Pro Ile Ser Ile Asn Tyr Arg Thr
                85                  90

<210> SEQ ID NO 39
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 39

Val Ser Ser Val Pro Thr Lys Leu Glu Val Val Ala Ala Thr Pro Thr

```
                1               5                   10                  15
Ser Leu Leu Ile Ser Trp Asp Ala Pro Ala Val Thr Val Asp Phe Tyr
            20                  25                  30

Leu Ile Thr Tyr Gly Glu Thr Gly Gly Pro Ser Trp Pro Gln Ala Phe
            35                  40                  45

Ala Val Pro Gly Ser Lys Ser Thr Ala Thr Ile Ser Gly Leu Lys Pro
    50                  55                  60

Gly Val Asp Tyr Thr Ile Thr Val Tyr Ala Ser Ser Ser Ser Arg Ile
65                  70                  75                  80

Ser Ser Ser Ser Ser Lys Pro Ile Ser Ile Asn Tyr Arg Thr
                85                  90

<210> SEQ ID NO 40
<211> LENGTH: 90
<212> TYPE: PRT
<213> ORGANISM: Artificial Sequence
<220> FEATURE:
<223> OTHER INFORMATION: Synthetic Peptide

<400> SEQUENCE: 40

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Leu Ile Thr Tyr Gly Glu Thr Gly Gly Pro Ser Trp Pro Gln Ala Phe
            35                  40                  45

Ala Val Pro Gly Ser Lys Ser Thr Ala Thr Ile Ser Gly Leu Lys Pro
    50                  55                  60

Gly Val Asp Tyr Thr Ile Thr Val Tyr Ala Glu His Pro Tyr Phe Ser
65                  70                  75                  80

Gly Ser Pro Ile Ser Ile Asn Tyr Arg Thr
                85                  90

<210> SEQ ID NO 41
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 41

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

Ile Ile Thr Tyr Gly Glu Thr Gly Tyr Val Gly Ser Trp Pro Gln Ala
            35                  40                  45

Phe Thr Val Pro Gly Ser Lys Ser Thr Ala Thr Ile Ser Gly Leu Lys
    50                  55                  60

Pro Gly Val Asp Tyr Thr Ile Thr Val Tyr Ala Tyr Ser Val Tyr Gly
65                  70                  75                  80

His Trp Ser Pro Ile Ser Ile Asn Tyr Arg Thr
                85                  90

<210> SEQ ID NO 42
<211> LENGTH: 92
<212> TYPE: PRT
<213> ORGANISM: Artificial Sequence
<220> FEATURE:
```

<223> OTHER INFORMATION: Synthetic Peptide

<400> SEQUENCE: 42

Val Ser Ser Val Pro Thr Lys Leu Glu Val Ala Ala Thr Pro Thr
1               5                   10                  15

Ser Leu Leu Ile Ser Trp Asp Ala Pro Ala Val Thr Val Asp Leu Tyr
            20                  25                  30

Leu Ile Thr Tyr Gly Glu Thr Gly Gly Phe Ser Trp Pro Gln Thr Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Tyr Lys Tyr Pro Tyr Gly
65                  70                  75                  80

Val Tyr Lys Ser Pro Ile Ser Ile Asn Tyr Arg Thr
                85                  90

<210> SEQ ID NO 43
<211> LENGTH: 90
<212> TYPE: PRT
<213> ORGANISM: Artificial Sequence
<220> FEATURE:
<223> OTHER INFORMATION: Synthetic Peptide

<400> SEQUENCE: 43

Val Ser Ser Val Pro Thr Lys Leu Glu Val Ala Ala Thr Pro Thr
1               5                   10                  15

Ser Leu Leu Ile Ser Trp Asp Ala Pro Ala Val Thr Val Asp Leu Tyr
            20                  25                  30

Val Ile Thr Tyr Gly Glu Thr Gly Gly Tyr Ser Trp Pro Gln Thr Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Tyr Tyr Asn Tyr Asn Asp
65                  70                  75                  80

Tyr Ser Pro Ile Ser Ile Asn Tyr Arg Thr
                85                  90

<210> SEQ ID NO 44
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 44

Val Ser Ser Val Pro Thr Lys Leu Glu Val Ala Ala Thr Pro Thr
1               5                   10                  15

Ser Leu Leu Ile Ser Trp Asp Ala Pro Ala Val Thr Val Asp Leu Tyr
            20                  25                  30

Ile Ile Thr Tyr Gly Glu Thr Gly Gly Ser Ala Trp Pro Gln Thr Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Tyr Ser Tyr Tyr Gly Val
65                  70                  75                  80

Glu Gly Ser Pro Ile Ser Ile Asn Tyr Arg Thr
                85                  90

-continued

<210> SEQ ID NO 45
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 45

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

Ile Ile Thr Tyr Gly Glu Thr Gly Gly Ser Ala Trp Pro Gln Thr Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Tyr Ser Val Asn Pro Tyr
65                  70                  75                  80

Tyr Met Ser Tyr Ser Pro Ile Ser Ile Asn Tyr Arg Thr
                85                  90

<210> SEQ ID NO 46
<211> LENGTH: 90
<212> TYPE: PRT
<213> ORGANISM: Artificial Sequence
<220> FEATURE:
<223> OTHER INFORMATION: Synthetic Peptide

<400> SEQUENCE: 46

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Phe Ile Thr Tyr Gly Glu Thr Gly Gly Ser Ser Trp Val Gln Thr Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Gly Pro Trp Asp Tyr
65                  70                  75                  80

Tyr Ser Pro Ile Ser Ile Asn Tyr Arg Thr
                85                  90

<210> SEQ ID NO 47
<211> LENGTH: 90
<212> TYPE: PRT
<213> ORGANISM: Artificial Sequence
<220> FEATURE:
<223> OTHER INFORMATION: Synthetic Peptide

<400> SEQUENCE: 47

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

Val Ile Thr Tyr Gly Glu Thr Gly Gly Ser Ser Trp Pro Gln Ala Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala His Ser Trp Asp His Ser
65                  70                  75                  80

Tyr Ser Pro Ile Ser Ile Asn Tyr Arg Thr
            85                  90

<210> SEQ ID NO 48
<211> LENGTH: 90
<212> TYPE: PRT
<213> ORGANISM: Artificial Sequence
<220> FEATURE:
<223> OTHER INFORMATION: Synthetic Peptide

<400> SEQUENCE: 48

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
                20                  25                  30

Val Ile Thr Tyr Gly Glu Thr Gly Gly Ser Ser Trp Pro Gln Ala Phe
            35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala His Ser Phe Gln Gly Pro
65                  70                  75                  80

Tyr Ser Pro Ile Ser Ile Asn Tyr Arg Thr
            85                  90

<210> SEQ ID NO 49
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 49

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
                20                  25                  30

Val Ile Thr Tyr Gly Glu Thr Gly Pro Gly Ser Gly Trp Pro Gln Ala
            35                  40                  45

Phe Thr Val Pro Gly Ser Lys Ser Thr Ala Thr Ile Ser Gly Leu Lys
    50                  55                  60

Pro Gly Val Asp Tyr Thr Ile Thr Val Tyr Ala Tyr Ser Trp Ser Gly
65                  70                  75                  80

Val Leu Gly Ser Pro Ile Ser Ile Asn Tyr Arg Thr
            85                  90

<210> SEQ ID NO 50
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 50

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
                20                  25                  30

Val Ile Thr Tyr Gly Glu Thr Gly Gly Val Val Trp Pro Gln Ala Phe
            35                  40                  45

Thr Val Pro Gly Ser Lys Ser Thr Ala Thr Ile Ser Gly Leu Lys Pro
            50                  55                  60

Gly Val Asp Tyr Thr Ile Thr Val Tyr Ala Gly Met Val Tyr Ser Tyr
 65                  70                  75                  80

Pro Tyr Arg Glu Tyr Ser Pro Ile Ser Ile Asn Tyr Arg Thr
                 85                  90

<210> SEQ ID NO 51
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 51

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Val Leu Tyr
                20                  25                  30

Leu Ile Thr Tyr Gly Glu Thr Gly Gly Asn Ser Pro Val Gln Glu Phe
            35                  40                  45

Ala Val Pro Gly Ser Lys Ser Thr Ala Thr Ile Ser Gly Leu Lys Pro
 50                  55                  60

Gly Val Asp Tyr Thr Ile Thr Val Tyr Ala Tyr Tyr Glu Ala Ala
 65                  70                  75                  80

Tyr Gly Ser Tyr Glu Phe Tyr Ser Pro Ile Ser Ile Asn Tyr Arg Thr
                 85                  90                  95

<210> SEQ ID NO 52
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 52

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Val Tyr Tyr
                20                  25                  30

Val Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Tyr Ser Asp Gln Val Glu
 65                  70                  75                  80

Tyr Tyr Glu Tyr Phe Tyr Gly Ser Pro Ile Ser Ile Asn Tyr Arg Thr
                 85                  90                  95

<210> SEQ ID NO 53
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 53

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Val Leu Tyr

```
            20                  25                  30
Val Ile Thr Tyr Gly Glu Thr Gly Asn Ser Pro Val Gln Glu Phe
            35                  40                  45

Ala Val Pro Gly Ser Lys Ser Thr Ala Thr Ile Ser Gly Leu Lys Pro
50                  55                  60

Gly Val Asp Tyr Thr Ile Thr Val Tyr Ala Tyr Pro His Ser Met
65                  70                  75                  80

Val Trp Pro Tyr Ser His Ser Ser Pro Ile Ser Ile Asn Tyr Arg Thr
                85                  90                  95
```

<210> SEQ ID NO 54
<211> LENGTH: 90
<212> TYPE: PRT
<213> ORGANISM: Artificial Sequence
<220> FEATURE:
<223> OTHER INFORMATION: Synthetic Peptide

<400> SEQUENCE: 54

```
Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Phe Tyr
            20                  25                  30

Val Ile Thr Tyr Gly Glu Thr Gly Asn Ser Pro Val Gln Glu Phe
            35                  40                  45

Thr Val Pro Gly Ser Lys Ser Thr Ala Thr Ile Ser Gly Leu Lys Pro
50                  55                  60

Gly Val Asp Tyr Thr Ile Thr Val Tyr Ala Gln Tyr Gly Trp Ala Arg
65                  70                  75                  80

Ser Ser Pro Ile Ser Ile Asn Tyr Arg Thr
                85                  90
```

<210> SEQ ID NO 55
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 55

```
Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Phe Tyr
            20                  25                  30

Val Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
50                  55                  60

Gly Val Asp Tyr Thr Ile Thr Val Tyr Ala Tyr Ala Val Glu Pro Tyr
65                  70                  75                  80

Phe Glu Tyr Ser Pro Ile Ser Ile Asn Tyr Arg Thr
                85                  90
```

<210> SEQ ID NO 56
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 56

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Leu Tyr
                20                  25                  30

Val Ile Thr Tyr Gly Glu Thr Gly Asn Ser Pro Val Gln Glu Phe
            35                  40                  45

Ala Val Pro Gly Ser Lys Ser Thr Ala Thr Ile Ser Gly Leu Lys Pro
    50                  55                  60

Gly Val Asp Tyr Thr Ile Thr Val Tyr Ala Tyr Asp Leu Trp Tyr Pro
65                  70                  75                  80

Tyr Val Tyr Gly Ser Pro Ile Ser Ile Asn Tyr Arg Thr
                85                  90

<210> SEQ ID NO 57
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 57

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
                20                  25                  30

Phe Ile Thr Tyr Gly Glu Thr Gly Asn Ser Pro Val Gln Glu Phe
            35                  40                  45

Ala Val Pro Gly Ser Lys Ser Thr Ala Thr Ile Ser Gly Leu Lys Pro
    50                  55                  60

Gly Val Asp Tyr Thr Ile Thr Val Tyr Ala Pro Trp Asn Gly Gly Tyr
65                  70                  75                  80

Ile Asp Ser Pro Ile Ser Ile Asn Tyr Arg Thr
                85                  90

<210> SEQ ID NO 58
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 58

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Leu Tyr
                20                  25                  30

Ile Ile Thr Tyr Gly Glu Thr Gly Gly Tyr Gly Gly Trp Pro Gln Ala
            35                  40                  45

Phe Thr Val Pro Gly Ser Lys Ser Thr Ala Thr Ile Ser Gly Leu Lys
    50                  55                  60

Pro Gly Val Asp Tyr Thr Ile Thr Val Tyr Ala His Asn Trp Ser Gly
65                  70                  75                  80

Gly Tyr Ser Pro Ile Ser Ile Asn Tyr Arg Thr
                85                  90

<210> SEQ ID NO 59
<211> LENGTH: 91
<212> TYPE: PRT

```
<213> ORGANISM: Artificial Sequence
<220> FEATURE:
<223> OTHER INFORMATION: Synthetic Peptide

<400> SEQUENCE: 59

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Phe Tyr
                20                  25                  30

Val Ile Thr Tyr Gly Glu Thr Gly Ala His Trp Pro Gly Tyr Gln Lys
            35                  40                  45

Phe Thr Val Pro Gly Ser Lys Ser Thr Ala Thr Ile Ser Gly Leu Lys
50                  55                  60

Pro Gly Val Asp Tyr Thr Ile Thr Val Tyr Ala Gln Phe Pro Trp Tyr
65                  70                  75                  80

Met Gly Ser Pro Ile Ser Ile Asn Tyr Arg Thr
                85                  90

<210> SEQ ID NO 60
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 60

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Tyr Tyr
                20                  25                  30

Val Ile Thr Tyr Gly Glu Thr Gly Ala His Ala Trp Pro Gly Tyr Gln
            35                  40                  45

Glu Phe Thr Val Pro Gly Ser Lys Ser Thr Ala Thr Ile Ser Gly Leu
50                  55                  60

Lys Pro Gly Val Asp Tyr Thr Ile Thr Val Tyr Ala Gln Tyr Pro Trp
65                  70                  75                  80

Tyr Gly Gly Ser Pro Ile Ser Ile Asn Tyr Arg Thr
                85                  90

<210> SEQ ID NO 61
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 61

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Tyr Tyr
                20                  25                  30

Tyr Ile Thr Tyr Gly Glu Thr Gly Ala Ser Ser Trp Pro Gly Tyr Gln
            35                  40                  45

Glu Phe Thr Val Pro Gly Ser Lys Ser Thr Ala Thr Ile Ser Gly Leu
50                  55                  60

Lys Pro Gly Val Asp Tyr Thr Ile Thr Val Tyr Ala Gln Ser Gly Trp
65                  70                  75                  80

Tyr Lys Tyr Ser Pro Ile Ser Ile Asn Tyr Arg Thr
                85                  90
```

<210> SEQ ID NO 62
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 62

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Phe Tyr
                20                  25                  30

Leu Ile Thr Tyr Gly Glu Thr Gly Ala Ser Ser Trp Pro Gly Tyr Gln
            35                  40                  45

Glu Phe Thr Val Pro Gly Ser Lys Ser Thr Ala Thr Ile Ser Gly Leu
50                  55                  60

Lys Pro Gly Val Asp Tyr Thr Ile Thr Val Tyr Ala Gln Tyr Pro Trp
65                  70                  75                  80

Asp Thr Gly Ser Pro Ile Ser Ile Asn Tyr Arg Thr
                85                  90

<210> SEQ ID NO 63
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 63

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Tyr Tyr
                20                  25                  30

Tyr Ile Thr Tyr Gly Glu Thr Gly Ala Ser Ser Trp Pro Gly Tyr Gln
            35                  40                  45

Glu Phe Thr Val Pro Gly Ser Lys Ser Thr Ala Thr Ile Ser Gly Leu
50                  55                  60

Lys Pro Gly Val Asp Tyr Thr Ile Thr Val Tyr Ala Gln Tyr Gly Trp
65                  70                  75                  80

Tyr Ser Gly Ser Pro Ile Ser Ile Asn Tyr Arg Thr
                85                  90

<210> SEQ ID NO 64
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 64

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Phe Tyr
                20                  25                  30

Val Ile Thr Tyr Gly Glu Thr Gly Ala His Ala Trp Pro Gly Tyr Gln
            35                  40                  45

Glu Phe Thr Val Pro Gly Ser Lys Ser Thr Ala Thr Ile Ser Gly Leu
50                  55                  60

Lys Pro Gly Val Asp Tyr Thr Ile Thr Val Tyr Ala Gln Tyr Gly Tyr
65                  70                  75                  80

His Gln Ser Ser Pro Ile Ser Ile Asn Tyr Arg Thr
                85                  90

<210> SEQ ID NO 65
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 65

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Phe Tyr
                20                  25                  30

Val Ile Thr Tyr Gly Glu Thr Gly Ser Ala Trp Pro Gly Tyr Gln Glu
            35                  40                  45

Phe Thr Val Pro Gly Ser Lys Ser Thr Ala Thr Ile Ser Gly Leu Lys
        50                  55                  60

Pro Gly Val Asp Tyr Thr Ile Thr Val Tyr Ala Gln Tyr Pro Tyr Tyr
65                  70                  75                  80

Gly Ser Ser Pro Ile Ser Ile Asn Tyr Arg Thr
                85                  90

<210> SEQ ID NO 66
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 66

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Phe Tyr
                20                  25                  30

Val Ile Thr Tyr Gly Glu Thr Gly Tyr Ala Trp Pro Gly Tyr Gln Glu
            35                  40                  45

Phe Thr Val Pro Gly Ser Lys Ser Thr Ala Thr Ile Ser Gly Leu Lys
        50                  55                  60

Pro Gly Val Asp Tyr Thr Ile Thr Val Tyr Ala Val Gly Pro Tyr Val
65                  70                  75                  80

Val Tyr Ser Pro Ile Ser Ile Asn Tyr Arg Thr
                85                  90

<210> SEQ ID NO 67
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 67

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Leu Tyr
                20                  25                  30

Val Ile Thr Tyr Gly Glu Thr Gly Pro Gly His Ser Ala Trp Pro Gln

```
                    35                  40                  45
Ala Phe Thr Val Pro Gly Ser Lys Ser Thr Ala Thr Ile Ser Gly Leu
 50                      55                  60

Lys Pro Gly Val Asp Tyr Thr Ile Thr Val Tyr Ala Tyr Trp Asp Trp
 65                  70                  75                  80

Asp Ser His Arg Tyr Ser Pro Ile Ser Ile Asn Tyr Arg Thr
                 85                  90

<210> SEQ ID NO 68
<211> LENGTH: 90
<212> TYPE: PRT
<213> ORGANISM: Artificial Sequence
<220> FEATURE:
<223> OTHER INFORMATION: Synthetic Peptide

<400> SEQUENCE: 68

Val Ser Ser Val Pro Thr Lys Leu Glu Val Val Ala Ala Thr Pro Thr
  1               5                  10                  15

Ser Leu Leu Ile Ser Trp Asp Ala Pro Ala Val Thr Val Val Leu Tyr
                 20                  25                  30

Val Ile Thr Tyr Gly Glu Thr Gly Ser Gly Ser Trp Pro Gln Ala Phe
             35                  40                  45

Thr Val Pro Gly Ser Lys Ser Thr Ala Thr Ile Ser Gly Leu Lys Pro
 50                      55                  60

Gly Val Asp Tyr Thr Ile Thr Val Tyr Ala Val Met Pro Trp Tyr Arg
 65                  70                  75                  80

Ser Ser Pro Ile Ser Ile Asn Tyr Arg Thr
                 85                  90

<210> SEQ ID NO 69
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 69

Val Ser Ser Val Pro Thr Lys Leu Glu Val Val Ala Ala Thr Pro Thr
  1               5                  10                  15

Ser Leu Leu Ile Ser Trp Asp Ala Pro Ala Val Thr Val Val Phe Tyr
                 20                  25                  30

Ile Ile Thr Tyr Gly Glu Thr Gly Ala Ala Val Trp Pro Gly His Gln
             35                  40                  45

Glu Phe Thr Val Pro Gly Ser Lys Ser Thr Ala Thr Ile Ser Gly Leu
 50                      55                  60

Lys Pro Gly Val Asp Tyr Thr Ile Thr Val Tyr Ala Val Gly Pro Trp
 65                  70                  75                  80

Asp Tyr Tyr Ser Pro Ile Ser Ile Asn Tyr Arg Thr
                 85                  90

<210> SEQ ID NO 70
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 70

Val Ser Ser Val Pro Thr Lys Leu Glu Val Val Ala Ala Thr Pro Thr
  1               5                  10                  15
```

```
Ser Leu Leu Ile Ser Trp Asp Ala Pro Ala Val Thr Val Val Phe Tyr
            20                  25                  30

Val Ile Thr Tyr Gly Glu Thr Gly Val His Trp Pro Gly Tyr Gln Lys
        35                  40                  45

Phe Thr Val Pro Gly Ser Lys Ser Thr Ala Thr Ile Ser Gly Leu Lys
    50                  55                  60

Pro Gly Val Asp Tyr Thr Ile Thr Val Tyr Ala Gln Phe Pro Trp Tyr
65                  70                  75                  80

Met Gly Ser Pro Ile Ser Ile Asn Tyr Arg Thr
                85                  90

<210> SEQ ID NO 71
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 71

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

Leu Ile Thr Tyr Gly Glu Thr Gly Gly Tyr Ser Trp Pro Gln Thr Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Tyr Lys Tyr Pro Tyr Gly
65                  70                  75                  80

Val Tyr Lys Ser Pro Ile Ser Ile Asn Tyr Arg Thr
                85                  90

<210> SEQ ID NO 72
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 72

Val Ser Ser Val Pro Thr Lys Leu Glu Val Val Ala Ala Thr Pro Thr
1               5                   10                  15

Ser Leu Leu Ile Ser Trp Asp Ala Ile Phe Trp Asn Val Ala Tyr Tyr
            20                  25                  30

Arg Ile Thr Tyr Gly Glu Thr Gly Gly Asn Ser Pro Val Gln Glu Phe
        35                  40                  45

Thr Val Pro Gly Tyr Ser Ser Thr Ala Thr Ile Ser Gly Leu Lys Pro
    50                  55                  60

Gly Val Asp Tyr Thr Ile Thr Val Tyr Ala Gly Asp Leu Ser Trp Asn
65                  70                  75                  80

Phe Asp Phe Tyr Ser Pro Ile Ser Ile Asn Tyr Arg Thr
                85                  90

<210> SEQ ID NO 73
<211> LENGTH: 97
<212> TYPE: PRT
<213> ORGANISM: Artificial Sequence
<220> FEATURE:
<223> OTHER INFORMATION: Synthetic Peptide
```

<400> SEQUENCE: 73

Val Ser Ser Val Pro Thr Lys Leu Glu Val Val Ala Ala Thr Pro Thr
1               5                   10                  15

Ser Leu Leu Ile Ser Trp Asp Ala Tyr Phe Trp Gly Trp Tyr Tyr Ser
                20                  25                  30

Val Trp Tyr Tyr Arg Ile Thr Tyr Gly Glu Thr Gly Gly Asn Ser Pro
            35                  40                  45

Val Gln Glu Phe Thr Val Pro Gly Tyr Ser Ser Thr Ala Thr Ile Ser
    50                  55                  60

Gly Leu Lys Pro Gly Val Asp Tyr Thr Ile Thr Val Tyr Ala Ile Met
65                  70                  75                  80

Glu Ser Trp Tyr Tyr Gly Ser Tyr Ser Pro Ile Ser Ile Asn Tyr Arg
                85                  90                  95

Thr

<210> SEQ ID NO 74
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 74

Val Ser Ser Val Pro Thr Lys Leu Glu Val Val Ala Ala Thr Pro Thr
1               5                   10                  15

Ser Leu Leu Ile Ser Trp Asp Ala Ser Ser Tyr Tyr Gly Val Val Ser
                20                  25                  30

Tyr Tyr Arg Ile Thr Tyr Gly Glu Thr Gly Gly Asn Ser Pro Val Gln
            35                  40                  45

Glu Phe Thr Val Pro Gly Tyr Ser Ser Thr Ala Thr Ile Ser Gly Leu
    50                  55                  60

Lys Pro Gly Val Asp Tyr Thr Ile Thr Val Tyr Ala Ser Tyr Tyr Tyr
65                  70                  75                  80

Trp Tyr Thr Ser Tyr Thr Lys Ser Pro Ile Ser Ile Asn Tyr Arg Thr
                85                  90                  95

<210> SEQ ID NO 75
<211> LENGTH: 97
<212> TYPE: PRT
<213> ORGANISM: Artificial Sequence
<220> FEATURE:
<223> OTHER INFORMATION: Synthetic Peptide

<400> SEQUENCE: 75

Val Ser Ser Val Pro Thr Lys Leu Glu Val Val Ala Ala Thr Pro Thr
1               5                   10                  15

Ser Leu Leu Ile Ser Trp Asp Ala Ser Ser Tyr Tyr Gly Val Val Glu
                20                  25                  30

Tyr Tyr Arg Ile Thr Tyr Gly Glu Thr Gly Gly Asn Ser Pro Val Gln
            35                  40                  45

Glu Phe Thr Val Pro Gly Tyr Ser Ser Thr Ala Thr Ile Ser Gly Leu
    50                  55                  60

Lys Pro Gly Val Asp Tyr Thr Ile Thr Val Tyr Ala Phe Tyr Tyr Tyr
65                  70                  75                  80

Trp Tyr Ser Tyr Ser Ser Val Ser Pro Ile Ser Ile Asn Tyr Arg
                85                  90                  95

Thr

<210> SEQ ID NO 76
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 76

```
Val Ser Ser Val Pro Thr Lys Leu Glu Val Val Ala Ala Thr Pro Thr
1               5                   10                  15

Ser Leu Leu Ile Ser Trp Asp Ala Ser Tyr Arg Ser His Trp Val His
            20                  25                  30

Tyr Tyr Arg Ile Thr Tyr Gly Glu Thr Gly Gly Asn Ser Pro Val Gln
        35                  40                  45

Glu Phe Thr Val Pro Ser Ser Ser Thr Ala Thr Ile Ser Gly Leu
    50                  55                  60

Lys Pro Gly Val Asp Tyr Thr Ile Thr Val Tyr Ala Met Asp Tyr Pro
65                  70                  75                  80

Gly Met Trp Tyr Gly Ser Pro Ile Ser Ile Asn Tyr Arg Thr
                85                  90
```

<210> SEQ ID NO 77
<211> LENGTH: 100
<212> TYPE: PRT
<213> ORGANISM: Artificial Sequence
<220> FEATURE:
<223> OTHER INFORMATION: Synthetic Peptide

<400> SEQUENCE: 77

```
Val Ser Ser Val Pro Thr Lys Leu Glu Val Val Ala Ala Thr Pro Thr
1               5                   10                  15

Ser Leu Leu Ile Ser Trp Asp Ala Trp Ser Ala Gln Asp Glu Tyr Tyr
            20                  25                  30

Ile Ser Tyr Tyr Arg Ile Thr Tyr Gly Glu Thr Gly Gly Asn Ser Pro
            35                  40                  45

Val Gln Glu Phe Thr Val Pro Ser Ser Ser Thr Ala Thr Ile Ser
    50                  55                  60

Gly Leu Lys Pro Gly Val Asp Tyr Thr Ile Thr Val Tyr Ala Met Tyr
65                  70                  75                  80

Ala Ser Tyr Ser Lys Gln Tyr Trp Gly Gln Gly Ser Pro Ile Ser Ile
                85                  90                  95

Asn Tyr Arg Thr
            100
```

<210> SEQ ID NO 78
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 78

```
Val Ser Ser Val Pro Thr Lys Leu Glu Val Val Ala Ala Thr Pro Thr
1               5                   10                  15

Ser Leu Leu Ile Ser Trp Asp Ala Glu Ser Trp Tyr Trp Pro Tyr Tyr
            20                  25                  30

Val Ser Tyr Tyr Arg Ile Thr Tyr Gly Glu Thr Gly Gly Asn Ser Pro
        35                  40                  45
```

```
Val Gln Glu Phe Thr Val Pro Ser Ser Ser Thr Ala Thr Ile Ser
 50                  55                  60

Gly Leu Lys Pro Gly Val Asp Tyr Thr Ile Thr Val Tyr Ala Phe Glu
 65                  70                  75                  80

His His Glu Gln Arg Tyr Tyr Ser Pro Ile Ser Ile Asn Tyr Arg Thr
                 85                  90                  95
```

<210> SEQ ID NO 79
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 79

```
Val Ser Ser Val Pro Thr Lys Leu Glu Val Val Ala Ala Thr Pro Thr
  1               5                  10                  15

Ser Leu Leu Ile Ser Trp Asp Ala Trp Asp Trp Val Tyr Pro Tyr Tyr
                 20                  25                  30

Val Ser Tyr Tyr Arg Ile Thr Tyr Gly Glu Thr Gly Gly Asn Ser Pro
                 35                  40                  45

Val Gln Glu Phe Thr Val Pro Ser Ser Ser Thr Ala Thr Ile Ser
 50                  55                  60

Gly Leu Lys Pro Gly Val Asp Tyr Thr Ile Thr Val Tyr Ala Tyr Ser
 65                  70                  75                  80

His Tyr Gln Met Ser Glu Tyr Ser Pro Ile Ser Ile Asn Tyr Arg Thr
                 85                  90                  95
```

<210> SEQ ID NO 80
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 80

```
Val Ser Ser Val Pro Thr Lys Leu Glu Val Val Ala Ala Thr Pro Thr
  1               5                  10                  15

Ser Leu Leu Ile Ser Trp Asp Ala Ser Tyr Pro Trp Trp Ser Tyr Val
                 20                  25                  30

Ser Tyr Tyr Arg Ile Thr Tyr Gly Glu Thr Gly Gly Asn Ser Pro Val
                 35                  40                  45

Gln Glu Phe Thr Val Pro Ser Ser Ser Thr Ala Thr Ile Ser Gly
 50                  55                  60

Leu Lys Pro Gly Val Asp Tyr Thr Ile Thr Val Tyr Ala Tyr Ser His
 65                  70                  75                  80

Tyr Gln Met Ser Glu Tyr Ser Pro Ile Ser Ile Asn Tyr Arg Thr
                 85                  90                  95
```

<210> SEQ ID NO 81
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 81

```
Val Ser Ser Val Pro Thr Lys Leu Glu Val Val Ala Ala Thr Pro Thr
  1               5                  10                  15
```

Ser Leu Leu Ile Ser Trp Asp Ala Phe Asp Gly Tyr Trp Tyr Asp Tyr
            20                  25                  30

Val Ser Tyr Tyr Arg Ile Thr Tyr Gly Glu Thr Gly Gly Asn Ser Pro
        35                  40                  45

Val Gln Glu Phe Thr Val Pro Ser Ser Ser Thr Ala Thr Ile Ser
    50                  55                  60

Gly Leu Lys Pro Gly Val Asp Tyr Thr Ile Thr Val Tyr Ala Tyr Ser
65                  70                  75                  80

His Ser Gln Gln Gln Tyr Leu Ser Pro Ile Ser Ile Asn Tyr Arg Thr
                85                  90                  95

<210> SEQ ID NO 82
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 82

Val Ser Ser Val Pro Thr Lys Leu Glu Val Val Ala Ala Thr Pro Thr
1               5                   10                  15

Ser Leu Leu Ile Ser Trp Asp Thr Tyr Ser Tyr Ser Pro Tyr Asn Tyr
            20                  25                  30

Val Ser Tyr Tyr Arg Ile Thr Tyr Gly Glu Thr Gly Gly Asn Ser Pro
        35                  40                  45

Val Gln Glu Phe Thr Val Pro Ser Ser Ser Thr Ala Thr Ile Ser
    50                  55                  60

Gly Leu Lys Pro Gly Val Asp Tyr Thr Ile Thr Val Tyr Ala Tyr Ser
65                  70                  75                  80

His Tyr Gln Met Ser Glu Tyr Ser Pro Ile Ser Ile Asn Tyr Arg Thr
                85                  90                  95

<210> SEQ ID NO 83
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 83

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Leu Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Phe Pro Ser Tyr Val Trp
65                  70                  75                  80

Trp Tyr Asn Pro Ile Ser Pro Ile Ser Ile Asn Tyr Arg Thr
                85                  90

<210> SEQ ID NO 84
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 84

```
Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

His Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Tyr His Tyr Trp Ser Gly
65                  70                  75                  80

Val Tyr Ser Tyr Tyr Pro Ser Pro Ile Ser Ile Asn Tyr Arg Thr
                85                  90                  95
```

<210> SEQ ID NO 85
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 85

```
Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

His Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Tyr Tyr Tyr Trp Ser Gly
65                  70                  75                  80

Val Tyr Ser Tyr Tyr Pro Ser Pro Ile Ser Ile Asn Tyr Arg Thr
                85                  90                  95
```

<210> SEQ ID NO 86
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 86

```
Val Ser Ser Val Pro Thr Lys Leu Glu Val Val Ala Ala Thr Pro Thr
1               5                   10                  15

Ser Leu Leu Ile Ser Trp Asp Ala Phe Asp Gly Tyr Trp Tyr Asp Tyr
            20                  25                  30

Val Ser Tyr Tyr Arg Ile Thr Tyr Gly Glu Thr Gly Gly Asn Ser Pro
        35                  40                  45

Val Gln Val Phe Thr Val Pro Ser Ser Ser Thr Ala Thr Ile Ser
    50                  55                  60

Gly Leu Lys Pro Gly Val Asp Tyr Thr Ile Thr Val Tyr Ala Tyr Ser
65                  70                  75                  80

His Ser Gln Leu Gln Tyr Leu Ser Pro Ile Ser Ile Asn Tyr Arg Thr
                85                  90                  95
```

<210> SEQ ID NO 87
<211> LENGTH: 96

```
<212> TYPE: PRT
<213> ORGANISM: Artificial Sequence
<220> FEATURE:
<223> OTHER INFORMATION: Synthetic Peptide

<400> SEQUENCE: 87

Val Ser Ser Val Pro Thr Lys Leu Glu Val Val Ala Ala Thr Pro Thr
 1               5                  10                  15

Ser Leu Leu Ile Ser Trp Asp Ala Phe Asp Gly Tyr Trp Tyr Asp Tyr
                20                  25                  30

Val Ser Phe Tyr Arg Ile Thr Tyr Gly Glu Ser Gly Gly Asn Ser Pro
            35                  40                  45

Val Gln Glu Phe Thr Val Pro Ser Ser Ser Thr Ala Thr Ile Ser
        50                  55                  60

Gly Leu Lys Pro Gly Val Asp Tyr Thr Ile Thr Val Tyr Ala Tyr Ser
65                  70                  75                  80

His Ser Gln Gln Gln Tyr Leu Ser Pro Asn Ser Ile Asn Tyr Arg Thr
                85                  90                  95

<210> SEQ ID NO 88
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 88

Val Ser Ser Val Pro Thr Lys Leu Glu Val Val Ala Ala Ala Pro Thr
 1               5                  10                  15

Thr Leu Leu Ile Ser Trp Asp Ala Phe Asp Gly Tyr Trp Tyr Asp Tyr
                20                  25                  30

Val Ser Tyr Tyr Arg Ile Thr Tyr Gly Glu Thr Gly Gly Asn Ser Pro
            35                  40                  45

Val Gln Glu Phe Thr Val Pro Ser Ser Ser Thr Ala Ile Ile Ser
        50                  55                  60

Gly Leu Lys Pro Gly Val Asp Tyr Thr Ile Thr Val Tyr Ala Tyr His
65                  70                  75                  80

His Ser Gln Gln Gln Tyr Leu Ser Pro Ile Ser Ile Asn Tyr Arg Thr
                85                  90                  95

<210> SEQ ID NO 89
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 89

Val Ser Ser Val Pro Thr Lys Leu Glu Val Val Ala Ala Thr Pro Thr
 1               5                  10                  15

Ser Leu Leu Ile Ser Trp Asp Ala Phe Asp Gly Tyr Trp Tyr Tyr Tyr
                20                  25                  30

Val Ser Tyr Tyr Arg Ile Thr Tyr Gly Glu Thr Gly Gly Asn Ser Pro
            35                  40                  45

Val Gln Glu Phe Thr Val Pro Ser Ser Ser Thr Ala Thr Ile Thr
        50                  55                  60

Gly Leu Lys Pro Gly Val Gly Tyr Thr Ile Thr Val Tyr Ala Tyr Ser
65                  70                  75                  80

His Ser Gln Leu Gln Tyr Leu Ser Pro Ile Ser Ile Asn Tyr Arg Thr
```

<210> SEQ ID NO 90
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 90

Val Ser Ser Val Pro Thr Lys Leu Glu Val Val Ala Ala Thr Pro Thr
1               5                   10                  15

Ser Leu Leu Ile Ser Trp Asp Ala Phe Asp Gly Tyr Trp Tyr Asp Tyr
            20                  25                  30

Val Ser Tyr Tyr Arg Ile Thr Tyr Gly Glu Thr Gly Gly Asn Ser Pro
        35                  40                  45

Val Gln Glu Phe Thr Val Pro Ser Ser Ser Thr Ala Thr Ile Thr
    50                  55                  60

Gly Leu Lys Pro Gly Val Asp Tyr Thr Ile Ala Val Tyr Ala Phe Ser
65                  70                  75                  80

His Ser Gln Leu Gln Tyr Leu Ser Pro Asn Ser Ile Asn Tyr Arg Thr
                85                  90                  95

<210> SEQ ID NO 91
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 91

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 92
<211> LENGTH: 97
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (30)..(30)
<223> OTHER INFORMATION: Pyrrolysine
<220> FEATURE:
<221> NAME/KEY: MISC_FEATURE
<222> LOCATION: (31)..(31)
<223> OTHER INFORMATION: Selenocysteine
<220> FEATURE:
<221> NAME/KEY: MISC_FEATURE
<222> LOCATION: (33)..(33)
<223> OTHER INFORMATION: Pyrrolysine
<220> FEATURE:
<221> NAME/KEY: misc_feature
<222> LOCATION: (41)..(46)
<223> OTHER INFORMATION: Xaa can be any naturally occurring amino acid
<220> FEATURE:
<221> NAME/KEY: MISC_FEATURE
<222> LOCATION: (47)..(47)
<223> OTHER INFORMATION: X or absent
<220> FEATURE:
<221> NAME/KEY: misc_feature
<222> LOCATION: (76)..(82)
<223> OTHER INFORMATION: Xaa can be any naturally occurring amino acid
<220> FEATURE:
<221> NAME/KEY: MISC_FEATURE
<222> LOCATION: (83)..(83)
<223> OTHER INFORMATION: X or absent
<220> FEATURE:
<221> NAME/KEY: MISC_FEATURE
<222> LOCATION: (84)..(84)
<223> OTHER INFORMATION: X or absent
<220> FEATURE:
<221> NAME/KEY: MISC_FEATURE
<222> LOCATION: (85)..(85)
<223> OTHER INFORMATION: X or absent
<220> FEATURE:
<221> NAME/KEY: MISC_FEATURE
<222> LOCATION: (86)..(86)
<223> OTHER INFORMATION: X or absent
<220> FEATURE:
<221> NAME/KEY: MISC_FEATURE
<222> LOCATION: (87)..(87)
<223> OTHER INFORMATION: X or absent
<220> FEATURE:
<221> NAME/KEY: MISC_FEATURE
<222> LOCATION: (88)..(88)
<223> OTHER INFORMATION: X or absent
<220> FEATURE:
<221> NAME/KEY: MISC_FEATURE
<222> LOCATION: (89)..(89)
<223> OTHER INFORMATION: X or absent

<400> SEQUENCE: 92

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Xaa Xaa Tyr
            20                  25                  30

Xaa Ile Thr Tyr Gly Glu Thr Gly Xaa Xaa Xaa Xaa Xaa Xaa Gln Glx
        35                  40                  45

Phe Glx Val Pro Gly Ser Lys Ser Thr Ala Thr Ile Ser Gly Leu Lys
    50                  55                  60

Pro Gly Val Asp Tyr Thr Ile Thr Val Tyr Ala Xaa Xaa Xaa Xaa Xaa
65                  70                  75                  80

Xaa Xaa Xaa Xaa Xaa Xaa Xaa Ser Pro Ile Ser Ile Asn Tyr Arg
                85                  90                  95

Thr

<210> SEQ ID NO 93
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 93

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Val Ile Thr Tyr Gly Glu Thr Gly Gly Ala Gly Ala Tyr Gly Gln Phe
        35                  40                  45

```
Ala Val Pro Gly Ser Lys Ser Thr Ala Thr Ile Ser Gly Leu Lys Pro
        50                  55                  60

Gly Val Asp Tyr Thr Ile Thr Val Tyr Ala Thr Gln Trp Gly Tyr Gln
 65                  70                  75                  80

Val Ser Ser Pro Ile Ser Ile Asn Tyr Arg Thr
                 85                  90
```

<210> SEQ ID NO 94
<211> LENGTH: 96
<212> TYPE: PRT
<213> ORGANISM: Artificial Sequence
<220> FEATURE:
<223> OTHER INFORMATION: Synthetic Peptide

<400> SEQUENCE: 94

```
Val Ser Ser Val Pro Thr Lys Leu Glu Val Val Ala Ala Thr Pro Thr
  1               5                  10                  15

Ser Leu Leu Ile Ser Trp Asp Ala Pro Ala Val Thr Val Asp Tyr Tyr
                 20                  25                  30

Val Ile Thr Tyr Gly Glu Thr Gly His Ser Pro Ser Gly Ser Gln Phe
             35                  40                  45

Ala Val Pro Gly Ser Lys Ser Thr Ala Thr Ile Ser Gly Leu Lys Pro
        50                  55                  60

Gly Val Asp Tyr Thr Ile Thr Val Tyr Ala Trp Ser Tyr Met Lys Gly
 65                  70                  75                  80

Gly Thr Trp Ile Arg Ser Met Ser Pro Ile Ser Ile Asn Tyr Arg Thr
                 85                  90                  95
```

<210> SEQ ID NO 95
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 95

```
Val Ser Ser Val Pro Thr Lys Leu Glu Val Val Ala Ala Thr Pro Thr
  1               5                  10                  15

Ser Leu Leu Ile Ser Trp Asp Ala Pro Ala Val Thr Val Val His Tyr
                 20                  25                  30

Phe Ile Thr Tyr Gly Glu Thr Gly Ser Ala Val Pro Pro Ser Gln Lys
             35                  40                  45

Phe Lys Val Pro Gly Ser Lys Ser Thr Ala Thr Ile Ser Gly Leu Lys
        50                  55                  60

Pro Gly Val Asp Tyr Thr Ile Thr Val Tyr Ala Lys Tyr Asp Tyr Trp
 65                  70                  75                  80

Gly Tyr Met Gly Tyr Tyr Ser Pro Ile Ser Ile Asn Tyr Arg Thr
                 85                  90                  95
```

<210> SEQ ID NO 96
<211> LENGTH: 90
<212> TYPE: PRT
<213> ORGANISM: Artificial Sequence
<220> FEATURE:
<223> OTHER INFORMATION: Synthetic Peptide

<400> SEQUENCE: 96

```
Val Ser Ser Val Pro Thr Lys Leu Glu Val Val Ala Ala Thr Pro Thr
  1               5                  10                  15
```

Ser Leu Leu Ile Ser Trp Asp Ala Pro Ala Val Thr Val Asp Tyr Tyr
            20                  25                  30

Val Ile Thr Tyr Gly Glu Thr Gly Gly Trp Pro Ser Ser Gln Phe
        35                  40                  45

Ala Val Pro Gly Ser Lys Ser Thr Ala Thr Ile Ser Gly Leu Lys Pro
 50                  55                  60

Gly Val Asp Tyr Thr Ile Thr Val Tyr Ala Gln Arg Asp Tyr His Val
65                  70                  75                  80

Tyr Ser Pro Ile Ser Ile Asn Tyr Arg Thr
                85                  90

<210> SEQ ID NO 97
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 97

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Asp Phe Tyr
            20                  25                  30

Val Ile Thr Tyr Gly Glu Thr Gly Ala Trp Gly Pro Gly Tyr Gln Phe
        35                  40                  45

Ala Val Pro Gly Ser Lys Ser Thr Ala Thr Ile Ser Gly Leu Lys Pro
 50                  55                  60

Gly Val Asp Tyr Thr Ile Thr Val Tyr Ala Gln Tyr Gln Gly Ser Ser
65                  70                  75                  80

Val Ser Ser Pro Ile Ser Ile Asn Tyr Arg Thr
                85                  90

<210> SEQ ID NO 98
<211> LENGTH: 90
<212> TYPE: PRT
<213> ORGANISM: Artificial Sequence
<220> FEATURE:
<223> OTHER INFORMATION: Synthetic Peptide

<400> SEQUENCE: 98

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Asp Tyr Tyr
            20                  25                  30

Val Ile Thr Tyr Gly Glu Thr Gly Ser His Gly Gly Gly Gln Phe
        35                  40                  45

Ala Val Pro Gly Ser Lys Ser Thr Ala Thr Ile Ser Gly Leu Lys Pro
 50                  55                  60

Gly Val Asp Tyr Thr Ile Thr Val Tyr Ala Gln His Gly Tyr Ala Val
65                  70                  75                  80

Tyr Ser Pro Ile Ser Ile Asn Tyr Arg Thr
                85                  90

<210> SEQ ID NO 99
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 99

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Val Ile Thr Tyr Gly Glu Thr Gly Ser Ser Gly Pro Ser Ser Gln Phe
        35                  40                  45

Ala Val Pro Gly Ser Lys Ser Thr Ala Thr Ile Ser Gly Leu Lys Pro
    50                  55                  60

Gly Val Asp Tyr Thr Ile Thr Val Tyr Ala Gln Gly Tyr His Gln Gly
65                  70                  75                  80

Tyr Trp Val Ser Ser Pro Ile Ser Ile Asn Tyr Arg Thr
                85                  90

<210> SEQ ID NO 100
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 100

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Val Ile Thr Tyr Gly Glu Thr Gly His Ser Pro Ser Gly Ser Gln Phe
        35                  40                  45

Ala Val Pro Gly Ser Lys Ser Thr Ala Thr Ile Ser Gly Leu Lys Pro
    50                  55                  60

Gly Val Asp Tyr Thr Ile Thr Val Tyr Ala Thr Gln Trp Gly Tyr Gln
65                  70                  75                  80

Val Ser Ser Pro Ile Ser Ile Asn Tyr Arg Thr
                85                  90

<210> SEQ ID NO 101
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 101

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Val Ile Thr Tyr Gly Glu Thr Gly Gly Ser His Gly Gly Gly Gln Phe
        35                  40                  45

Ala Val Pro Gly Ser Lys Ser Thr Ala Thr Ile Ser Gly Leu Lys Pro
    50                  55                  60

Gly Val Asp Tyr Thr Ile Thr Val Tyr Ala Thr Gln Trp Gly Tyr Gln
65                  70                  75                  80

Val Ser Ser Pro Ile Ser Ile Asn Tyr Arg Thr
                85                  90

<210> SEQ ID NO 102
<211> LENGTH: 93

```
<212> TYPE: PRT
<213> ORGANISM: Artificial Sequence
<220> FEATURE:
<223> OTHER INFORMATION: Synthetic Peptide

<400> SEQUENCE: 102

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Val Ile Thr Tyr Gly Glu Thr Gly Trp Ser His Gly Ser Ser Gln Phe
        35                  40                  45

Ala Val Pro Gly Ser Lys Ser Thr Ala Thr Ile Ser Gly Leu Lys Pro
    50                  55                  60

Gly Val Asp Tyr Thr Ile Thr Val Tyr Ala Gln Gly Tyr His Gln Gly
65                  70                  75                  80

Tyr Trp Val Ser Ser Pro Ile Ser Ile Asn Tyr Arg Thr
                85                  90

<210> SEQ ID NO 103
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 103

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Leu His Tyr
            20                  25                  30

Leu Ile Thr Tyr Gly Glu Thr Gly Gly Val Val Pro Pro Ser Gln Lys
        35                  40                  45

Phe Lys Val Pro Gly Ser Lys Ser Thr Ala Thr Ile Ser Gly Leu Lys
    50                  55                  60

Pro Gly Val Asp Tyr Thr Ile Thr Val Tyr Ala Lys Ser Tyr Ser Met
65                  70                  75                  80

Trp Tyr Ser Pro Ile Ser Ile Asn Tyr Arg Thr
                85                  90

<210> SEQ ID NO 104
<211> LENGTH: 92
<212> TYPE: PRT
<213> ORGANISM: Artificial Sequence
<220> FEATURE:
<223> OTHER INFORMATION: Synthetic Peptide

<400> SEQUENCE: 104

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val His Tyr
            20                  25                  30

Tyr Ile Thr Tyr Gly Glu Thr Gly Gly Pro Ser Ser Pro Ser Gln Lys
        35                  40                  45

Phe Lys Val Pro Gly Ser Lys Ser Thr Ala Thr Ile Ser Gly Leu Lys
    50                  55                  60

Pro Gly Val Asp Tyr Thr Ile Thr Val Tyr Ala Tyr Tyr Trp Trp Arg
65                  70                  75                  80

Gly Tyr Ser Asn Pro Ile Ser Ile Asn Tyr Arg Thr
```

<210> SEQ ID NO 105
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 105

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val His Tyr
            20                  25                  30

Phe Ile Thr Tyr Gly Glu Thr Gly Ser Ala Val Pro Pro Ser Gln Lys
        35                  40                  45

Phe Lys Val Pro Gly Ser Lys Ser Thr Ala Thr Ile Ser Gly Leu Lys
    50                  55                  60

Pro Gly Val Asp Tyr Thr Ile Thr Val Tyr Ala Tyr Phe Gly Ser Tyr
65                  70                  75                  80

Tyr Asp Trp Val Gln Ser Pro Ile Ser Ile Asn Tyr Arg Thr
                85                  90

<210> SEQ ID NO 106
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 106

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val His His Tyr
            20                  25                  30

Phe Ile Thr Tyr Gly Glu Thr Gly Tyr Ser Pro Ser Pro Ser Gln Lys
        35                  40                  45

Phe Ala Val Pro Gly Ser Lys Ser Thr Ala Thr Ile Ser Gly Leu Lys
    50                  55                  60

Pro Gly Val Asp Tyr Thr Ile Thr Val Tyr Ala Tyr Tyr Pro Gly Trp
65                  70                  75                  80

Arg Gly Tyr Tyr Gln Glu Ser Pro Ile Ser Ile Asn Tyr Arg Thr
                85                  90                  95

<210> SEQ ID NO 107
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 107

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
            20                  25                  30

Val Ile Thr Tyr Gly Glu Thr Gly Ser Trp Gly Tyr Tyr Ala Gln Glu
        35                  40                  45

Phe Thr Val Pro Gly Ser Lys Ser Thr Ala Thr Ile Ser Gly Leu Lys
    50                  55                  60

Pro Gly Val Asp Tyr Thr Ile Thr Val Tyr Ala Phe Gly Gly Tyr Tyr
65                  70                  75                  80

Asn Trp Leu Ser Ser Pro Ile Ser Ile Asn Tyr Arg Thr
                85                  90

<210> SEQ ID NO 108
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 108

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val His His Tyr
                20                  25                  30

Val Ile Thr Tyr Gly Glu Thr Gly Ser His Val Pro Val Ser Gln Lys
            35                  40                  45

Phe Ala Val Pro Gly Ser Lys Ser Thr Ala Thr Ile Ser Gly Leu Lys
    50                  55                  60

Pro Gly Val Asp Tyr Thr Ile Thr Val Tyr Ala Tyr Phe Gly Gln Tyr
65                  70                  75                  80

Tyr Glu Trp Ile Tyr Ser Pro Ile Ser Ile Asn Tyr Arg Thr
                85                  90

<210> SEQ ID NO 109
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 109

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val His Tyr
                20                  25                  30

Leu Ile Thr Tyr Gly Glu Thr Gly Ala Pro Val Pro Pro Ser Gln Lys
            35                  40                  45

Phe Lys Val Pro Gly Ser Lys Ser Thr Ala Thr Ile Ser Gly Leu Lys
    50                  55                  60

Pro Gly Val Asp Tyr Thr Ile Thr Val Tyr Ala Tyr Tyr Pro Gly Trp
65                  70                  75                  80

Arg Gly Tyr Tyr Gln Glu Ser Pro Asn Ser Ile Asn Tyr Arg Thr
                85                  90                  95

<210> SEQ ID NO 110
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 110

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val His His Tyr
                20                  25                  30

Leu Ile Thr Tyr Gly Glu Gly Tyr Val Pro Ser Gln Lys
            35                  40                  45

Phe Ala Val Pro Gly Ser Lys Ser Thr Ala Thr Ile Ser Gly Leu Lys
 50                  55                  60

Pro Gly Val Asp Tyr Thr Ile Thr Val Tyr Ala Phe Gly Gly Tyr Tyr
 65                  70                  75                  80

Asn Trp Leu Ser Ser Pro Ile Ser Ile Asn Tyr Arg Thr
                85                  90

<210> SEQ ID NO 111
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 111

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val His His Tyr
                20                  25                  30

Leu Ile Thr Tyr Gly Glu Thr Gly Phe His Val Pro Ser Gln Lys
            35                  40                  45

Phe Ala Val Pro Gly Ser Lys Ser Thr Ala Thr Ile Ser Gly Leu Lys
 50                  55                  60

Pro Gly Val Asp Tyr Thr Ile Thr Val Tyr Ala Phe Gly Gly Tyr Tyr
 65                  70                  75                  80

Asn Trp Leu Ser Ser Pro Ile Ser Ile Asn Tyr Arg Thr
                85                  90

<210> SEQ ID NO 112
<211> LENGTH: 94
<212> TYPE: PRT
<213> ORGANISM: Artificial Sequence
<220> FEATURE:
<223> OTHER INFORMATION: Synthetic Peptide

<400> SEQUENCE: 112

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val His His Tyr
                20                  25                  30

Leu Ile Thr Tyr Gly Glu Thr Gly Gly Ser Val Pro Val Ser Gln Lys
            35                  40                  45

Phe Ala Val Pro Gly Ser Lys Ser Thr Ala Thr Ile Ser Gly Leu Lys
 50                  55                  60

Pro Gly Val Asp Tyr Thr Ile Thr Val Tyr Ala Phe Gly Gly Tyr Tyr
 65                  70                  75                  80

Asn Trp Leu Ser Ser Pro Ile Asn Ser Ile Asn Tyr Arg Thr
                85                  90

<210> SEQ ID NO 113
<211> LENGTH: 100
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (25)..(29)
<223> OTHER INFORMATION: Xaa can be any naturally occurring amino acid

```
<220> FEATURE:
<221> NAME/KEY: MISC_FEATURE
<222> LOCATION: (30)..(30)
<223> OTHER INFORMATION: X or absent
<220> FEATURE:
<221> NAME/KEY: MISC_FEATURE
<222> LOCATION: (31)..(31)
<223> OTHER INFORMATION: X or absent
<220> FEATURE:
<221> NAME/KEY: MISC_FEATURE
<222> LOCATION: (32)..(32)
<223> OTHER INFORMATION: X or absent
<220> FEATURE:
<221> NAME/KEY: MISC_FEATURE
<222> LOCATION: (33)..(33)
<223> OTHER INFORMATION: X or absent
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: MISC_FEATURE
<222> LOCATION: (57)..(59)
<223> OTHER INFORMATION: Isoleucine or leucine
<220> FEATURE:
<221> NAME/KEY: misc_feature
<222> LOCATION: (79)..(86)
<223> OTHER INFORMATION: Xaa can be any naturally occurring amino acid
<220> FEATURE:
<221> NAME/KEY: MISC_FEATURE
<222> LOCATION: (87)..(87)
<223> OTHER INFORMATION: X or absent
<220> FEATURE:
<221> NAME/KEY: MISC_FEATURE
<222> LOCATION: (88)..(88)
<223> OTHER INFORMATION: X or absent
<220> FEATURE:
<221> NAME/KEY: MISC_FEATURE
<222> LOCATION: (89)..(89)
<223> OTHER INFORMATION: X or absent
<220> FEATURE:
<221> NAME/KEY: MISC_FEATURE
<222> LOCATION: (90)..(90)
<223> OTHER INFORMATION: X or absent
<220> FEATURE:
<221> NAME/KEY: MISC_FEATURE
<222> LOCATION: (91)..(91)
<223> OTHER INFORMATION: X or absent
<220> FEATURE:
<221> NAME/KEY: MISC_FEATURE
<222> LOCATION: (92)..(92)
<223> OTHER INFORMATION: X or absent

<400> SEQUENCE: 113

Val Ser Ser Val Pro Thr Lys Leu Glu Val Ala Ala Thr Pro Thr
1               5                   10                  15

Ser Leu Leu Ile Ser Trp Asp Ala Xaa Xaa Xaa Xaa Xaa Xaa Xaa
                20                  25                  30

Val Xaa Tyr Tyr Arg Ile Thr Tyr Gly Glu Thr Gly Gly Asn Ser Pro
        35                  40                  45

Val Gln Glu Phe Thr Val Pro Asx Xaa Xaa Xaa Thr Ala Thr Ile Ser
    50                  55                  60

Gly Leu Lys Pro Gly Val Asp Tyr Thr Ile Thr Val Tyr Ala Xaa Xaa
65                  70                  75                  80

Xaa Xaa Xaa Xaa Xaa Xaa Xaa Xaa Xaa Xaa Ser Pro Ile Ser Ile
                85                  90                  95

Asn Tyr Arg Thr
            100

<210> SEQ ID NO 114
<211> LENGTH: 98
```

<212> TYPE: PRT
<213> ORGANISM: Artificial Sequence
<220> FEATURE:
<223> OTHER INFORMATION: Synthetic Peptide

<400> SEQUENCE: 114

Val Ser Ser Val Pro Thr Lys Leu Glu Val Val Ala Ala Thr Pro Thr
1               5                   10                  15

Ser Leu Leu Ile Ser Trp Asp Ala Pro Tyr Asn Tyr Gly Tyr Tyr Trp
            20                  25                  30

Val Asn Tyr Tyr Arg Ile Thr Tyr Gly Glu Thr Gly Gly Asn Ser Pro
        35                  40                  45

Val Gln Glu Phe Thr Val Pro Gly Tyr Ser Ser Thr Ala Thr Ile Ser
    50                  55                  60

Gly Leu Lys Pro Gly Val Asp Tyr Thr Ile Thr Val Tyr Ala Tyr Tyr
65                  70                  75                  80

Tyr Glu Glu Ser Glu Tyr Ser Asp Gly Ser Pro Ile Ser Ile Asn Tyr
                85                  90                  95

Arg Thr

<210> SEQ ID NO 115
<211> LENGTH: 97
<212> TYPE: PRT
<213> ORGANISM: Artificial Sequence
<220> FEATURE:
<223> OTHER INFORMATION: Synthetic Peptide

<400> SEQUENCE: 115

Val Ser Ser Val Pro Thr Lys Leu Glu Val Val Ala Ala Thr Pro Thr
1               5                   10                  15

Ser Leu Leu Ile Ser Trp Asp Ala Met Gln Tyr Ser Glu Tyr Asp Val
            20                  25                  30

Thr Tyr Tyr Arg Ile Thr Tyr Gly Glu Thr Gly Gly Asn Ser Pro Val
        35                  40                  45

Gln Glu Phe Thr Val Pro Gly Ser Ser Ser Thr Ala Thr Ile Ser Gly
    50                  55                  60

Leu Lys Pro Gly Val Asp Tyr Thr Ile Thr Val Tyr Ala Val Trp Gln
65                  70                  75                  80

Tyr Met His Tyr Met His Ser Tyr Ser Pro Ile Ser Ile Asn Tyr Arg
                85                  90                  95

Thr

<210> SEQ ID NO 116
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 116

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Ser Ser Thr Ala Thr Ile Ser Gly Leu Lys Pro
    50                  55                  60

```
Gly Val Asp Tyr Thr Ile Thr Val Tyr Ala Phe Gly His Tyr Tyr Gly
65                  70                  75                  80

Ser Trp Ala Trp Ser Pro Ile Ser Ile Asn Tyr Arg Thr
                85                  90

<210> SEQ ID NO 117
<211> LENGTH: 93
<212> TYPE: PRT
<213> ORGANISM: Artificial Sequence
<220> FEATURE:
<223> OTHER INFORMATION: Synthetic Peptide

<400> SEQUENCE: 117

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Ser Ser Thr Ala Thr Ile Ser Gly Leu Lys Pro
            50                  55                  60

Gly Val Asp Tyr Thr Ile Thr Val Tyr Ala Phe Gly His Tyr Tyr Gly
65                  70                  75                  80

Ser Trp Val Trp Ser Pro Ile Ser Ile Asn Tyr Arg Thr
                85                  90
```

METHODS AND COMPOSITION FOR MODIFYING ENZYMES

CROSS-REFERENCE TO RELATED APPLICATIONS

This application is a national phase application under 35 U.S.C. § 371 of International Application No. PCT/US2016/042516 filed Jul. 15, 2016, which claims the benefit of priority of U.S. Provisional Patent Application No. 62/193,955, filed Jul. 17, 2015. The entire contents of each of the above-referenced disclosures are specifically incorporated herein by reference without disclaimer.

STATEMENT OF GOVERNMENT SUPPORT

This invention was made with government support under grants R01-GM072688 and R01-GM090324 awarded by the National Institutes of Health. The government has certain rights in the invention.

BACKGROUND OF THE INVENTION

I. Field of the Invention

Embodiments are directed generally to biology, medicine, and protein engineering.

II. Background

Engineering enzymes with desirable catalytic properties remains a major goal of biotechnology, as enzymes are important in many industries including chemical, pharmaceutical, food, dairy and textile. Essentially all standard enzyme-engineering approaches, e.g., structure-guided design and directed evolution, modify the enzyme itself. The prerequisites of these approaches limit their broader application. Structure-guided design requires detailed knowledge of the three-dimensional (3D) structure and catalytic mechanism of the target enzyme, and directed evolution requires effective strategies for generating and screening numerous mutant enzymes. De novo enzyme design also requires detailed understanding of the reaction mechanism. Industrial enzymes are often purified from their native hosts because they cannot be recombinantly produced in organisms suitable for protein engineering such as *Escherichia coli* and yeast. Their 3D structures are seldom known, and their assays are often labor intensive. These characteristics make it a formidable challenge to apply standard protein-engineering approaches to industrial enzymes, although it is often desired to modulate their properties. Thus, there is a need in the art for better methods for modifying enzyme activities and/or specificities, especially for enzymes in which little information is available regarding the three-dimensional structure.

SUMMARY OF THE INVENTION

This disclosure provides a solution for the previously described problem by providing methods for developing novel enzyme substrate specificity modifiers that can be generated in the absence of any knowledge regarding the enzyme's structure. Also described herein are polypeptides that bind to β-galactosidase or lipase 1 and polypeptides that are inhibitors and specificity modifiers of β-galactosidase or lipase 1. Aspects of the disclosure relate to a polypeptide comprising an amino acid sequence that is at least 90% identical to an amino acid sequence selected from SEQ ID NO:1-90, 93-112 or 114-117.

In some embodiments, the polypeptide binds to β-galactosidase. β-galactosidase catalyzes lactose hydrolysis and trans-galactosylation reactions. In some embodiments, the β-galactosidase is from *B. circulans* (ATCC 31382). In some embodiments, the polypeptide binds to Biolacta®. In some embodiments, the polypeptide is an inert binder. The term "inert binder" refers to a binding polypeptide that does not modify any activities of the protein or enzyme. In some embodiments, the inert binder does not reduce an activity of the protein by more than 10, 9, 8, 7, 6, 5, 4, 3, 2, or 1% (or any derivable range therein). Activities include substrate specificity, selectivity, enzyme activity, substrate binding, etc. . . . In some embodiments, the inert binder is a polypeptide comprising an amino acid sequence that is at least 90% identical to SEQ ID NO:1, 8, 14, 23, 26, 30, 38, 39, 47, 52, 62, 67, 69, 70, 75, or 76.

In some embodiments, the polypeptide is an inhibitor of β-galactosidase. In some embodiments, the inhibitor is a polypeptide comprising an amino acid sequence that is at least 90% identical to SEQ ID NO:73, 74, 77, or 83.

In some embodiments, the polypeptide is a specificity modifier of β-galactosidase. The term "specificity modifier," as used herein, is a polypeptide that changes the substrate profile of the enzyme, but does not necessarily change the activity of the enzyme. For example, a specificity modifier may change the binding activity of an enzyme so that the enzyme preferential binds one substrate over another or so that the enzyme binds a substrate not previously bound by the enzyme. However, a specificity modifier will not typically change the level of activity of the enzyme. In some embodiments, the specificity modifier comprises an amino acid sequence that is at least 90% identical to SEQ ID NO:78, 81, 86, 87, or 88. In some embodiments, the specificity modifier is a polypeptide that is at least 90% identical to SEQ ID NO: 87.

In some embodiments, the polypeptide comprises an amino acid sequence that is at least 90% identical to SEQ ID NO:1, 8, 14, 23, 26, 30, 38, 39, 47, 52, 62, 67, 69, 70, 75, or 76. In some embodiments, the polypeptide comprises an amino acid sequence that is at least 90% identical to SEQ ID NO:73, 74, 77, or 83. In some embodiments, the polypeptide comprises an amino acid sequence that is at least 90% identical to SEQ ID NO:78, 81, 86, 87, or 88. In some embodiments, the polypeptide comprises an amino acid sequence that is at least 90% identical to SEQ ID NO:87.

Further aspects relate to a polypeptide that binds to *Candida rugosa* lipase 1 (CRL1). In some embodiments the polypeptide comprises an amino acid sequence that is at least 80% identical to an amino acid sequence selected from SEQ ID NO:93-112 or 114-117. In some embodiments, the polypeptide have at least 70, 75, 80, 81, 82, 83, 84, 85, 86, 87, 88, 89, 90, 91, 92, 93, 94, 95, 96, 97, 98, 99, or 100% identity to SEQ ID NO:93-112 or 114-117. In some embodiments, the polypeptide is an inert binder of CRL1. In some embodiments, the inert binder comprises an amino acid sequence that is at least 90% identical to SEQ ID NO:93, 94, 96, or 97. In some embodiments, the polypeptide is an inhibitor of CRL1. In some embodiments, the inhibitor comprises an amino acid sequence that is at least 90% identical to SEQ ID NO:107, 116, or 117. In some embodiments, the polypeptide is a specificity modifier of CRL1. In some embodiments, the specificity modifier comprises an amino acid sequence that is at least 90% identical to SEQ ID NO:115 or 109.

In some embodiments, a polypeptide of the disclosure is at least or exactly 50, 55, 60, 65, 70, 75, 80, 85, 86, 87, 88, 89, 90, 91, 92, 93, 94, 95, 96, 97, 98, or 99% identical (or any derivable range therein) to a polypeptide with an amino acid sequence of any one of SEQ ID NO:1-90, 93-112, or 114-117

"Homology" or "identity" or "similarity" are used interchangeable and refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure. Identity between two polypeptides is determined by comparing only the regions that that are similar. For example is a polypeptide having a sequence of 20 amino acids is compared to a polypeptide having the same 20 amino acids, but also having a segment that is at the N or C-terminus of that 20 amino acids, the % identity would still be 100%, since both polypeptides have the same stretch of 20 amino acids, without any intervening amino acids.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" or "homology" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology.

Biologically equivalent polynucleotides are those having the specified percent homology and encoding a polypeptide having the same or similar biological activity.

In some embodiments, the percentage identity is calculated by dividing the number of identities by one of: length of shortest sequence, length of alignment, mean length of sequence, number of non-gap positions, or number of equivalenced positions excluding overhangs.

In some embodiments, the polypeptide further comprises a modification. The modification may be pegylation, glycosylation, conjugation to a detectable label, conjugation to a diagnostic agent, conjugation to a fluorescent, luminescent, or bioluminescent material, conjugation to a radioactive material, conjugation to a therapeutic agent, and/or conjugation to a second polypeptide. In some embodiments, the second polypeptide is an Avi, Calmodulin, polyglutamate, polylysine, polyarginine, E, FLAG, HA, His, Myc, polyhistidine, GST, MBP, S, SBP, Softag 1, Softag3, Strep, TC, V5, VSV, lectin, biotin, streptavidin, SUMO, HaloTag, SiTag or Express polypeptide.

Further aspects of the disclosure relate to a polynucleotide encoding a polypeptide described herein. Further aspects relate to a method for making a polypeptide described herein, wherein the method comprises expressing the polynucleotide of the disclosure in a cell. Yet further aspects relate to a host cell comprising a polynucleotide described herein.

Further aspects relate to a method for identifying an enzyme-binding polypeptide (EBP) that modifies substrate specificity of an enzyme binding at least one substrate, the method comprising: contacting the enzyme with a polypeptide library comprising a plurality of EBPs that bind different epitopes of the enzyme; identifying EBPs that bind to the enzyme to form an EBP-enzyme complex; assaying for the activity level and substrate specificity of the EBP-enzyme complex; and identifying EBPs that modify the substrate specificity of the enzyme by identifying EBPs that, when in an EBP-enzyme complex, have a different substrate specificity than un-complexed EBP; wherein the EBP-enzyme complex has a level of activity that is at least 50% of the un-complexed activity level and/or wherein the EBP-enzyme complex retains binding to a substrate.

In some embodiments, the disclosure relates to a method for identifying an EBP that modifies substrate specificity of an enzyme binding at least one substrate, the method comprising: contacting the enzyme with a polypeptide library comprising a plurality of EBPs that bind different epitopes of the enzyme; identifying EBPs that bind to the enzyme to form an EBP-enzyme complex; assaying for the activity level and substrate specificity of the EBP-enzyme complex; and identifying EBPs that modify the substrate specificity of the enzyme by identifying EBPs that, when in an EBP-enzyme complex, have a different substrate specificity than un-complexed EBP; wherein the catalytic rate constant of the EBP-enzyme complex is ≥50% of the un-complexed enzyme for at least one substrate and/or wherein the EBP-enzyme complex retains binding to a substrate.

The term "epitope," as used herein is also used interchangeable with antigen and refers to a polypeptide segment recognized by a binding protein (i.e. EBPs described herein). In some embodiments, the epitope is multiple polypeptide segments (i.e. discontinuous segments of a protein).

In some embodiments, the EBP-enzyme complex has a level of activity that is at least 50, 55, 60, 65, 70, 75, 80, 85, 90, 91, 92, 93, 94, 95, 96, 97, 98, 99, or 100% (or any derivable range therein) of the un-complexed activity level.

In some embodiments, the catalytic rate constant of the EBP-enzyme complex is ≥50% 50, 55, 60, 65, 70, 75, 80, 85, 90, 91, 92, 93, 94, 95, 96, 97, 98, 99, or 100% (or any derivable range therein) of the un-complexed enzyme for at least one substrate.

The activity of the protein may be determined by methods known in the art and by an assay that depends on the enzymatic activity that the enzyme possesses. For example, the activity of the β-galactosidase or lipase 1 may be determined by using an assay as described in the examples. In some embodiments the activity refers to the specific catalytic rate constant ($k_{cat}$), which can be determined by methods known in the art and/or described herein. In some embodiments, the activity refers to the amount of the product of interest per unit of enzyme after a preset duration of reaction.

In some embodiments, the duration of reaction is at least, at most, or exactly 1, 2, 3, 4, 5, 10, 15, 20, 30, 60 minutes or 1, 1.5, 2, 2.5, 3, 6, 12, 24, 48, 72, or 96 hours (or any derivable range therein).

In some embodiments, identifying EBPs that modify the substrate specificity comprises identifying polypeptides that: a) bind to the enzyme that has an un-bound active site; and b) do not bind to the enzyme when a molecule is bound at the active site of the enzyme. In some embodiments, the molecule is an inhibitor. In some embodiments, the molecule is a small molecule or a polypeptide. In some embodiments the small molecule is a low molecular weight organic compound of less than, greater than or exactly 2 kDa, 1.5 kDa, 1 kDa, 900 Da, 800 Da, 700 Da, 600 Da, or 500 Da.

In some embodiments, identifying EBPs that modify the substrate specificity comprises identifying polypeptides that: a) reduce the amount of a first product of interest per unit of enzyme after a preset duration of reaction; and b) do not reduce the amount of a second product of interest per unit of enzyme after a preset duration of reaction.

In some embodiments, identifying EBPs that modify the substrate specificity comprises identifying polypeptides that: a) increase the amount of a first product of interest per unit of enzyme after a preset duration of reaction; and b) do not increase the amount of a second product of interest per unit of enzyme after a preset duration of reaction.

The products may be reduced or increased by at least, at most, or exactly 5, 10, 15, 20, 25, 30, 35, 40, 45, 50, 55, 60, 65, 70, 75, 80, 85, 90, 95, or 100% (or any derivable range therein).

In some embodiments, the EBP that modifies substrate specificity does not bind to the active site of the enzyme. In some embodiments, the EBP that modifies substrate specificity does not bind to the site of catalysis (i.e. region of active site where the catalytic reaction occurs). In some embodiments, the EBP that modifies substrate specificity is a polypeptide that modifies the accessibility of the active site of the enzyme.

In some embodiments, the EBP that modifies substrate specificity inhibits the catalytic activity of the enzyme for a first substrate, but does not inhibit the catalytic activity of the enzyme for a second substrate.

In some embodiments, the method further comprises performing a competition assay with a molecule that binds to the active site of the enzyme. In some embodiments, the method further comprises performing a competition assay with a molecule that inhibits the catalytic activity of the enzyme. In some embodiments, the molecule is an inhibitor of the enzyme. In some embodiments, the method further comprises the use of a mutant enzyme with a substitution in the active site (or putative active site). This mutant may act as a decoy in the assays described herein and be useful for enriching for EBPs.

In some embodiments, the EBP that modifies the substrate specificity of the enzyme is one that competes for binding to the enzyme with an inhibitor that binds to the active site of the enzyme. In some embodiments, the three-dimensional structure of the protein is unknown.

In some embodiments, the method further comprises masking dominant epitopes of the enzyme. A dominant epitope may be an epitope that has a high affinity for one or more binding proteins. In some embodiments, the dominant epitopes are masked by the binding of a molecule to the epitope. In some embodiments, the molecule does not modify the specificity or enzymatic activity of the enzyme. In some embodiments, the molecule is an inert binding polypeptide.

In some embodiments, the enzyme is a protease, peptidase, amidase, glycosidase, lipase, esterase, glycosyltransferase, hydrolase, polymerase, nuclease, nucleotide polymerase, kinase, phosphatase, methyltransferase, acetyltransferase, oxidase, dehydrogenase, peroxidase, catalase, transpeptidase, transamidase, carboxylase, gamma-glutamyltransferase, isomerase, epimerase, lyase, oxygenase, ligase, oxidoreductase, transferase, transglutaminase, protein glutaminase, amylase, deacetylase or demethylase. In some embodiments, the enzyme is a hydrolase. In some embodiments, the enzyme is β-galactosidase. In some embodiments, the enzyme is lipase 1.

In some embodiments, the polypeptide library is a library of antibodies (including nanobodies and fragments of antibodies), disulfide-constrained peptides, affibodies, affilins, anticalins (lipocalins), fynomers, Kunitz variants, fibronectin type III (FN3) domains (monobodies, and related binding protein systems using the FN3 domains), ankyrin repeats (DARPins), APP, camelid $V_{HH}$, disulfide-constrained peptides or other nonantibody scaffolds. In some embodiments, the polypeptide library is one known in the art are described herein. In some embodiments, the polypeptide library is a library of polypeptides that are less than 100 kDa. In some embodiments, the polypeptide library is a library of polypeptides that are less than or exactly about 90, 80, 70, 60, 50, 40, 30, 25, 20, 19, 18, 17, 16, 15, 14, 13, 12, 11, or 10 kDa (or any derivable range therein).

In some embodiments, the polypeptide library is a library of monobodies. In some embodiments, the monobody library comprises a plurality of polypeptides having a variant fibronectin type III (FN3) domain, compared to wildtype (SEQ ID NO:91), comprising one or more alterations in one or more of beta strand C, beta strand D, beta strand F, and/or beta strand G. In some embodiments, one or more of the variant amino acids corresponds to position 30, 31, 33, 49, 47, 75, 76, 84, and/or 85 of SEQ ID NO:91. In certain embodiments the amino acid variations contribute to the binding specificity of a monobody. In a further aspect, beta strand variations can be used in conjunction with variations in the loops of FN3. In certain aspects, beta strand variations can be used in conjunction with variations in the AB loop, the BC loop, the CD loop, the DE loop, and/or the FG loop of FN3 to generate a polypeptide library or a nucleic acid library encoding the same. The AB, BC, CD, DE, and FG correspond to amino acid positions 15-16, 22-30, 39-45, 51-55 and 76-87 of SEQ ID NO:91, respectively. FN3 polypeptides can be modified by inserting or deleting 1, 2, 3, 4, 5, 6, 7, 8, 9, 10, 20 or more amino acids, or any range derivable therein, in a FN3 loop. In certain aspects, variations in loops AB, CD, and EF may be specifically excluded, either individually or in various combinations. In some embodiments it is contemplated that an FN3 variant does not include a substitution, insertion and/or deletion in a bottom loop (loop AB, CD, EF). In further embodiments modifications in the bottom loop(s) is limited to 1, 2, 3, 4, or 5 or fewer substitutions, insertions, and/or deletions.

In certain embodiments, polypeptides comprise a variant fibronectin type III (FN3) domain comprising one or more amino acid substitutions in both a loop region of FN3 and in a non-loop region of FN3. In certain aspects, the one or more amino acid substitution in the non-loop segment is one or more substitution in beta strand C, beta strand D, beta strand F, and/or beta strand G.

In a further aspect the one or more amino acid substitution in beta strand C is one or more amino acid substitution corresponding to position 31, 32, 33, 34, 35, 36, 37, 38, or 39 of SEQ ID NO:91. In certain aspects, the amino acid substitution in beta strand C corresponds to position 31 or 33 of SEQ ID NO:91.

In certain aspects, the one or more amino acid substitution in beta strand D is one or more amino acid substitution corresponding to position 44, 45, 46, 47, 48, 49, 50 or 51 of SEQ ID NO:91. In a further aspect, the amino acid substitution in beta strand D corresponds to position 44, 45, 47, or 49 of SEQ ID NO:91.

In still a further aspect, the one or more amino acid substitution in beta strand F is one or more amino acid substitution corresponding to position 67, 68, 69, 70, 71, 72, 73, 74, or 75 of SEQ ID NO:91. In a further aspect, the amino acid substitution in beta strand F corresponds to position 71, 73, 75 or 76 of SEQ ID NO:91.

In certain aspects, the one or more amino acid substitution in beta strand G is one or more amino acid substitution corresponding to position 85, 86, 87, 88, 89, 90, 91, 92, 93, or 94 of SEQ ID NO:91. In a further aspect, the amino acid substitution in beta strand G corresponds to position 84 or 85 of SEQ ID NO:91.

The polypeptides can include amino acid substitutions correspond to one or more amino acid substitutions at position 31, 33, 47, 49, 73, and/or 75 of SEQ ID NO:91. In certain aspects, the polypeptide further comprises an amino acid substitution corresponding to amino acid position 30 of SEQ ID NO:91. In a further aspect, the polypeptide comprises one or more amino acid substitution corresponding to amino acid position 41, 42, 43, 44, or 45 of SEQ ID NO:91. The polypeptide can further comprise one or more amino acid substitution corresponding to amino acid position 76, 77, 78, 79, 80, 81, 82, 83, 84, or 85 of SEQ ID NO:91.

In certain embodiments, the polypeptide can comprise 1, 2, 3, 4 or more insertions and/or deletions of amino acids corresponding to amino acids of SEQ ID NO:91. Insertions can include, but are not limited to stretches of poly-serine, poly-alanine, poly-valine, poly-threonine, or polymers of any other of the 20 amino acids, that is subsequently mutagenized or diversified for generating a combinatorial polypeptide library. Diversification of these inserted residues can include alteration to 1, 2, 3, 4, 5, 6, 7, 8, 9, 10, 11, 12, 13, 14, 15, 16, 17, 18, or 19 of the other natural amino acids. In certain aspects 1, 2, 3, 4, 5, 6, 7, 8, 9, 10, 11, 12, 13, 14, 15, 16, 17, 18, 19, 20, 21, 22, 23, 24, 25 or more contiguous amino acids are inserted into one or more of the AB, BC, CD, DE, EF, FG loops of a FN3 domain polypeptide. In a further aspect, the polypeptide can comprise an insertion, a deletion, or both an insertion and a deletion. The insertion and deletion need not be located at the same position and may be located at sites distal or proximal to each other. The insertion and/or deletion can be in a loop or non-loop portion of the FN3 domain polypeptide. In certain aspects, at least one loop region of FN3 comprises an insertion of at least 2 amino acids. In a further aspect, at least one region of FN3 comprises an insertion of 2 to 25 amino acids in at least one loop region. In certain aspects at least 2, 3, or more loop regions comprise an insertion. In certain aspects, the polypeptide has at least one loop region of FN3 comprises a deletion of at least 1, 2, 3, 4, 5, 6, 7, 8, 9, or 10 amino acids, including all values and ranges there between. In certain aspects, at least 2, 3, or 4 loop or non-loop segments, portions, or regions comprise a deletion of at least 1 amino acid. In certain aspects, the polypeptide comprises at least one insertion and one deletion in at least one loop or non-loop region. In a further aspect, the polypeptide comprises an insertion and a deletion in the same loop or non-loop region. The term region indicates the amino acids of a particular structural segment of the polypeptide as defined by secondary structure and/or crystal structure corresponding to the amino acids of SEQ ID NO:91 or its variants.

In certain aspects, the polypeptide is at least 50%, 60%, 70%, 80%, or 90%, including all values and ranges there between, identical to SEQ ID NO:91.

The polypeptides of the disclosure can be comprised in a polypeptide library or encoded in a polynucleotide library that can be screened for particular polypeptide characteristics, e.g., biding affinity. One or more members of the library can then be isolated from other members of the library and analyzed. In certain aspects the library comprises or encodes a plurality of those polypeptides described herein. In certain aspects, the polypeptide library is pre-selected to bind a target and those preselected members are then further diversified in selected amino acid position to generate a targeted library that is subsequently screened for a particular characteristic or property.

Certain aspects are directed to polynucleotides encoding one or more polypeptide described herein. In certain embodiments the polynucleotide is an expression cassette or an expression construct. The expression construct can be capable of expressing the encoded polypeptide in a host cell, such as a prokaryotic or eukaryotic cell line or strain. In certain aspects the expression construct is functional in one or more polypeptide expression systems known in the art. In a further aspect, the expression construct is functional in bacteria, yeast, insect cells or the like.

The polypeptide can further comprise a second FN3 domain that may or may not have been selected for affinity to a particular target. The second FN3 domain may or may not contain additional amino acid variations or diversification. In other aspects, the polypeptide can further comprise a non-FN3 polypeptide that enhances the FN3 polypeptide binding affinity for a target molecule. The non-FN3 polypeptide can include, but is not limited to domains involved in phospho-tyrosine binding (e.g., SH2, PTB), phosphoserine binding (e.g., UIM, GAT, CUE, BTB/POZ, VHS, UBA, RING, HECT, WW, 14-3-3, Polo-box), phosphothreonine binding (e.g., FHA, WW, Polo-box), proline-rich region binding (e.g., EVH1, SH3, GYF), acetylated lysine binding (e.g., Bromo), methylated lysine binding (e.g., Chromo, PHD), apoptosis (e.g., BIR, TRAF, DED, Death, CARD, BH), cytoskeleton modulation (e.g., ADF, GEL, DH, CH, FH2), or other cellular functions (e.g., EH, CC, VHL, TUDOR, PUF Repeat, PAS, MH1, LRR1 IQ, HEAT, GRIP, TUBBY, SNARE, TPR, TIR, START, SOCS Box, SAM, RGS, PDZ, PB1, LIM, F-BOX, ENTH, EF-Hand, SHADOW, ARM, ANK), silica binding (e.g., polyarginine, Protein L2), keratin binding (e.g., polylysine, KBD), hydroxyapatite binding (e.g., N15), carbohydrate binding (e.g., CBD).

In certain aspects, variants in any one or more of positions that correspond with amino acid position 15, 16, 17, 21, 22, 23, 24, 25, 26, 27, 28, 29, 30, 38, 39, 40, 41, 42, 43, 44, 45, 51, 52, 53, 54, 55, 56, 60, 61, 62, 63, 64, 65, 66, 76, 77, 78, 79, 80, 81, 82, 83, 84, 85, 86, 87, 88, 93, 95, and/or 96, including all ranges there between, can be specifically included in the claimed embodiments. In other embodiments, variants in any one or more of positions that correspond with amino acid position 15, 16, 17, 21, 22, 23, 24, 25, 26, 27, 28, 29, 30, 38, 39, 40, 41, 42, 43, 44, 45, 51, 52, 53, 54, 55, 56, 60, 61, 62, 63, 64, 65, 66, 76, 77, 78, 79, 80, 81, 82, 83, 84, 85, 86, 87, 88, 93, 95, and/or 96, including all ranges there between, can be specifically excluded. It will be understood that these recited positions are based on the sequence of the tenth domain in human FN3 (SEQ ID NO:91). It is contemplated that embodiments concern FN3 variants in the tenth domain of FN3 in other organisms as well and that a skilled artisan can readily identify the corresponding positions in the tenth domain of FN3 from other organisms based on the position in the human sequence.

Certain embodiments are directed to a monobody library comprising a plurality of polypeptides having a variant fibronectin type III (FN3) domain, compared to wildtype (SEQ ID NO:91), comprising one or more alterations or variants in one or more of beta strand C, beta strand D, beta strand F, and/or beta strand G. In certain aspects one or more of the altered or variant amino acids corresponds to position 30, 31, 33, 49, 47, 75, 76, 84, and/or 85 of SEQ ID NO:91.

The monobody library can comprise variant FN3 domains that further comprise an insertion or deletion of at least 1, 2, 3, 4, 5, 6, 7, 8, 9, 10, 15, 20, 25 amino acids in at least one loop region of FN3. The monobody library can also comprise variant FN3 domains comprising an amino acid insertion in loop FG. The monobody library can also comprise a plurality of those polypeptides described above.

In some embodiments, the polypeptides described herein are non-naturally occurring polyepeptides. In some embodiments, the disclosure relates to a polyeptide that is at least 80% identical to an amino acid sequence selected from SEQ ID NO:1-90, wherein the polypeptide does not comprise SEQ ID NO:91. In some embodiments, the disclosure relates to a polypeptide comprising an amino acid sequence that is at least 80% identical to an amino acid sequence selected from SEQ ID NO:93-112 or 114-117, wherein the polypeptide does not comprise SEQ ID NO:91.

In some embodiments, the polypeptide comprises post-translation modifications that are different than the polypeptide produced in its native environment. For example, the polypeptide may differ in the status of myristoylation, palmitoylation, isoprenylation or prenylation, farnesylation, geranylgeranylation, glypiation, lipoylation, phosphopantetheinylation, diphthamide formation, ethanolamine phosphoglycerol attachment, hypusine formation, acylation, acetylation, formylation, alkylation, methylation, arginylation, polyglutamylation, polyglycylation, butyrylation, glycosylation, polysialylation, malonylation, hydroxylation, iodination (e.g. of thyroglobulin), nucleotide addition such as ADP-ribosylation, oxidation, phosphate ester (O-linked) or phosphoramidate (N-linked) formation, phosphorylation, adenylylation, propionylation, pyroglutamate formation, S-glutathionylation, S-nitrosylation, S-sulfenylation, succinylation, sulfation, glycation, carbamylation, carbonylation, biotinylation, acylation of conserved lysine residues with a biotin appendage, or pegylation.

In some embodiments, the polypeptides are produced in host cells known in the art and/or described herein and including bacteria (such as *E. coli, B. subtilis, S. viofoceoruber*), yeast (such as *S. cerevisiae, P. pastoris*), fungi (such as *A. oryzae*), eukaryotic cells, insect cells, A549, B-cells, B16, BHK-21, C2C12, C6, CaCo-2, CAP/, CAP-T, CHO, CHO2, CHO-DG44, CHO-K1, COS-1, Cos-7, CV-1, Dendritic cells, DLD-1, Embryonic Stem (ES) Cell or derivative, H1299, HEK, 293, 293T, 293FT, Hep G2, Hematopoietic Stem Cells, HOS, Huh-7, Induced Pluripotent Stem (iPS) Cell or derivative, Jurkat, K562, L5278Y, LNCaP, MCF7, MDA-MB-231, MDCK, Mesenchymal Cells, Min-6, Monocytic cell, Neuro2a, NIH 3T3, NIH3T3L1, K562, NK-cells, NS0, Panc-1, PC12, PC-3, Peripheral blood cells, Plasma cells, Primary Fibroblasts, RBL, Renca, RLE, SF21, SF9, SH-SY5Y, SK-MES-1, SK-N-SH, SL3, SW403, Stimulus-triggered Acquisition of Pluripotency (STAP) cell or derivate SW403, T-cells, THP-1, Tumor cells, U2OS, U937, peripheral blood lymphocytes, expanded T cells, hematopoietic stem cells, or Vero cells.

Certain embodiments include methods of making a polypeptide or polynucleotide library comprising a plurality of FN3 variants. In certain aspects the library can contain 10, 100, 1000, $10^4$, $10^5$, $10^6$, $10^7$, $10^8$, $10^9$, $10^{10}$, $10^{11}$, $10^{12}$, $10^{13}$, $10^{14}$, $10^{15}$ or more different polypeptide or polynucleotide variants, including all values and ranges there between, though it will be understood that there may be duplicate variants. The methods of making such a polypeptide or polynucleotide include the engineering of various amino acids substitutions, deletions, and/or insertion described herein.

Certain embodiments include methods of selecting one or more FN3 variants comprising conducting one or more binding assays using a FN3 library having a plurality of different FN3 variants. In certain aspects the library can comprise FN3 polypeptides having amino acid variations in the FN3 loops, FN3 beta-strands, or both FN3 loops and beta-strands. After conducting the binding assay(s) one or more FN3 variants are selected that have a particular property, such as binding specificity and/or binding affinity to a target. In certain aspects, the amino acid or nucleic acid sequence of one or more of the selected library members can be determined using conventional methods. The sequence of the selected FN3 polypeptide(s) can then be used to produce a second library that introduces further variation of the selected sequences. The second library can then be screened for FN3 polypeptides having a particular property. The process can be repeated 1, 2, 3, 4, 5, 6, 7, 8, 9, 10 or more times. Additional iterations would enrich the library as well as potentially include other variants.

In certain aspects the method for selecting a protein binding domain specific for a target comprises (a) detecting target specific binding of one or more members of a polypeptide library comprising a plurality of FN3 domain polypeptides having amino acid substitutions that correspond to at least amino acid position 31, 33, 47, 49, 71, 73, and/or 75 of SEQ ID NO:91; and (b) selecting the protein binding domain that specifically binds the target. The method can further comprise first preparing the plurality of FN3 domain polypeptide variants described herein, e.g., FN3 domains having amino acid substitutions that correspond to at least amino acid position 31, 33, 47, 49, 71, 73, and/or 75 of SEQ ID NO:91. A polypeptide identified as exhibiting a particular characteristic can be isolated. In certain aspects, the method can further comprise determining the nucleic acid and/or the amino acid of sequence of the selected protein binding domain. The selected protein binding domain can then be synthesized or expressed.

Methods can further comprise conducting a first screen of a library having amino acid variations in only FN3 loops or only FN3 beta strands and conducting a second screen using variations in only FN3 loops or only FN3 beta strands. In certain aspects the first screen uses only variations in the FN3 loops and the second screen only uses variations in the FN3 beta-strands. In a further aspect, the second screen can use variations in both FN3 loops and beta-strands. In certain aspects, the FN3 amino acid residues varied in the first screen are or are not varied in the second screen.

Further aspects include methods of identifying a polypeptide that specifically binds a target comprising detecting specific binding of one or more polypeptides of a polypeptide library, the library comprising a plurality of fibronectin type III (FN3) polypeptides as described herein.

Further aspects include methods of detecting a target molecule comprising contacting a sample containing the target with a fibronectin type III (FN3) binding domain that specifically binds the target.

Further aspects include a method for modifying the specificity of an enzyme comprising contacting the enzyme with an EBP.

Certain aspects include methods of producing a fibronectin type III (FN3) variant comprising: (a) expressing a polypeptide comprising an amino acid sequence; and (b) isolating and/or purifying the expressed variant FN3 domain from a host cell expressing the variant FN3.

Certain embodiments are directed to kits. In certain aspects, a kit can comprise a plurality of polypeptides as described herein. In a further aspect, a kit can comprise a plurality of polynucleotides encoding FN3 domain variants as described herein.

The term "fibronectin type III domain" or "FN3 domain" refers to a domain (region) from a wild-type fibronectin from any organism. In specific embodiments, the FN3 domain is the tenth domain of fibronectin type III.

The term "fibronectin type III domain variant" or "FN3 variant domain" refers to a polypeptide region in which one or more amino acid substitutions, deletions, and/or insertions are present as compared to the amino acid sequence of a wildtype FN3 domain. In certain embodiments, the FN3 variant or FN3 variant domain has an alteration with respect to specifically the human tenth module of the fibronectin type III domain sequence (SEQ ID NO:91). The term "substitutional variant" includes the replacement of one or more amino acids in a peptide sequence with a conservative or non-conservative amino acid(s). In some embodiments, the FN3 domain variant has increased binding properties compared to the wildtype FN3 domain relative to a particular target.

The term "FN3-domain polypeptide" refers to a polypeptide that includes at least one FN3 domain. A "variant FN3 domain polypeptide" refers to a polypeptide that includes at least one variant FN3 domain. It is contemplated that such polypeptides are capable of specifically binding a polypeptide or protein.

A "non-FN3 binding sequence" refers to an amino acid sequence of more than 15 contiguous amino acid residues that is not present in an FN3 domain or an FN3 domain variant and that specifically binds to a protein or polypeptide. In some embodiments, a non-FN3 binding sequence is specifically a non-tenth module fibronectin type III domain binding sequence.

The β sheet is a form of regular secondary structure in proteins. Beta sheets consist of beta strands connected laterally by at least two or three backbone hydrogen bonds, forming a generally twisted, pleated sheet. A beta strand (also β strand) is a stretch of polypeptide chain typically 3 to 10 amino acids long with backbone in an almost fully extended conformation.

A loop is a less ordered, flexible stretch of amino acids (as compared to alpha helices and beta sheets) that typically connect other structural elements of a protein. In the context of FN3, the loops are designated by the beta-strands they connect, for example the loop connecting beta-strand A and beta-strand B is the AB loop. The term BC loop refers to the amino acids corresponding to amino acids 22 to 30 of SEQ ID NO:91. The term CD loop refers to the amino acids corresponding to amino acids 39 to 45 of SEQ ID NO:91. The term DE loop refers to the amino acids corresponding to amino acids 51 to 55 of SEQ ID NO:91. The term FG loop refers to the amino acids corresponding to amino acids 76 to 87 of SEQ ID NO:91.

Beta strand A refers to the amino acids preceding the AB loop

Beta strand B refers to the amino acids connecting the AB and BC loops

Beta strand C refers to the amino acids connecting the BC and CD loops.

Beta strand D refers to the amino acids connecting the CD and DE loops.

Beta strand E refers to the amino acids connecting the DE and EF loops.

Beta strand F refers to the amino acids connecting the EF and FG loops.

Beta strand G refers to the amino acids after the FG loop.

The term "binding protein" refers to a polypeptide that specifically binds another compound, such as a polypeptide through non-covalent chemical interactions.

As used herein, "monobody" is intended to mean a polypeptide having a sequence and structure related to the tenth module of the fibronectin type III domain (FN3) that includes a beta-strand domain lacking in disulfide bonds and containing a plurality of beta-strands, two or more loop regions each connecting one beta-strand to another beta-strand, and optionally an N-terminal tail, a C-terminal tail, or both, wherein at least one of the two or more loop regions, the N-terminal tail, and or the C-terminal tail is characterized by activity in binding a target protein or molecule. More specifically, in some embodiments such monobodies can include three or more loop regions or, even more specifically, four or more loop regions. The size of such polypeptide monobodies is preferably less than about 30 kDa, more preferably less than about 20 kDa.

The term "library" refers to a collection (e.g., to a plurality) of polypeptides having different amino acid sequences and different protein binding properties. In some embodiments there is a variant FN3 domain library comprising polypeptides having different variations of the FN3 domain. Unless otherwise noted, the library is an actual physical library of polypeptides or nucleic acids encoding the polypeptides. In further embodiments, there is a database that comprises information about a library that has been generated or a theoretical library that can be generated. This information may be a compound database comprising descriptions or structures of a plurality of potential variant FN3 domains. "FN3-based molecule" refers to a molecule having an amino acid sequence of an FN3 domain or FN3 variant domain.

The term "specifically binds" or "specific binding" refers to the measurable and reproducible ability of an FN3-based molecule to bind another molecule (such as a target), that is determinative of the presence of the target molecule in the presence of a heterogeneous population of molecules including biological molecules. For example, an FN3-based molecule that specifically or preferentially binds to a target is a polypeptide that binds this target with greater affinity, avidity, more readily, and/or with greater duration than it binds to most or all other molecules. "Specific binding" does not necessarily require (although it can include) exclusive binding.

An polypeptide that specifically binds to a target with an affinity of at least $1 \times 10^{-6}$ M at room temperature under physiological salt and pH conditions, as measured by surface plasmon resonance. An example of such a measurement is provided in the Example section.

The term "target" refers to a peptide, antigen or epitope that specifically binds to an FN3-based binding molecule or monobody described herein. Targets include, but are not limited to, epitopes present on proteins, peptides, carbohydrates, lipids, and/or organic/inorganic mineral surfaces.

The term "non-natural amino acid residue" refers to an amino acid residue that is not present in the naturally occurring FN3 domain in a mammal, such as a human.

The terms "tag", "epitope tag" or "affinity tag" is used interchangeably herein, and usually refers to a molecule or domain of a molecule that is specifically recognized by an antibody or other binding partner. The term also refers to the binding partner complex as well. Thus, for example, biotin or a biotin/avidin complex is both regarded as an affinity tag. In addition to epitopes recognized in epitope/antibody interactions, affinity tags also comprise "epitopes" recognized by other binding molecules (e.g., ligands bound by receptors), ligands bound by other ligands to form heterodimers or homodimers, His$_6$ bound by Ni-NTA, biotin bound by avidin, streptavidin, or anti-biotin antibodies, and the like.

Epitope tags are well known to those of skill in the art. Moreover, antibodies specific to a wide variety of epitope tags are commercially available. These include but are not limited to myc epitopes (c-myc antibodies are available from Sigma, St. Louis), the HNK-1 carbohydrate epitope, the HA epitope, the HSV epitope, the His$_4$, His$_5$, and His$_6$ epitopes that are recognized by the His epitope specific antibodies (see, e.g., Qiagen), and the like. In addition, vectors for epitope tagging proteins are commercially available. A polypeptide can be tagged with the FLAG® epitope (N-terminal, C-terminal or internal tagging), the c-myc epitope (C-terminal) or both the FLAG (N-terminal) and c-myc (C-terminal) epitopes.

The term "conjugate" in the context of an FN3-based molecule refers to a chemical linkage between the FN3-based molecule and a non-FN3-based molecule. It is specifically contemplated that this excludes a regular peptide bond found between amino acid residues under physiologic conditions in some embodiments.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "preventing," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any other embodiment discussed herein, and vice versa. Furthermore, compositions and kits can be used to achieve recited methods.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-E. Modulation of enzyme catalytic properties with synthetic binding proteins. (a) Schematic of the monobody scaffold, with the locations of diversified residues shown as spheres and strands, loops and termini labeled. (b) Schematic drawing of different classes of binding proteins. (c-e) Schematic representations of the hydrolysis reaction (c), and the trans-galactosylation reaction of BgaD-D in the absence (d) or the presence (e) of a specificity modifier (yellow). Hypothesized subsites are labeled −1, +1, +2 and +3. The catalytic site where hydrolysis and trans-galactosylation reactions occur is shown as a red triangle. In (d) and (e), the initial step of lactose cleavage is omitted for brevity. A sugar linkage newly formed by the trans-galactosylation reaction is marked in red. The specificity enhancer restricts the access of larger oligosaccharides to the subsites (d).

FIG. 2A-G. Monobodies modulate catalytic properties of BgaD-D. (a) Schematics showing the designs of three selection campaigns. (b) Competitive binding among monobodies. Binding signals of BgaD-D to Mb(BgaD_L23) immobilized on the streptavidin-coated beads in the absence and presence of saturating concentrations of purified monobodies are shown. (c) Affinity and inhibitory effects of monobodies. The $K_d$ values and effects on the ONPG hydrolysis reaction are shown. The absorbance change for the hydrolysis reaction in the presence of BgaD-D and the indicated monobodies are plotted, after subtracting the background reaction without the enzyme. (d) Effects of monobodies on GOS production by BgaD-D (also see FIGS. 4 and 5). The amounts of indicated sugars relative to the total sugar amount (weight/weight) are plotted as a function of reaction time (left column) and the degree of lactose consumption (right column). The concentrations of monobodies used for these experiments are 100 µM for Mb(BgaD_L02), 200 µM for Mb(BgaD_L14) and 100 µM for Mb(BgaD_L23), sufficient to achieve >95% saturation of the enzyme. (e) Relative amounts of oligo-saccharides in each of the reactions shown in d, measured at the time point when the total GOS amount reaches the maximum. The degree of lactose consumption is also shown. The color scheme is the same as in panels a and c. (f) Effects of active site mutations on monobody-BgaD-D interaction (see also FIG. 5A). The bars with asterisks show the lower limit. Each group of four bars corresponds to BgaD-D/WT, BgaD-D/E447Q, BgaD-D/E447K, and BgaD-D/E447R, respectively. (g) Effects of oligo-saccharides on monobody-BgaD-D interaction (see also FIG. 6B). In f and g, monobody names are abbreviated for brevity. The error bars indicate s.d. (n=3). Where no error bars appear, the errors are within the size of the markers. Each group of four bars corresponds to +Lactose, +DP3, +DP4, and +DP5, respectively.

FIG. 3A-D. Monobodies binding to the BgaD-D isozyme of Biolacta®. (a) The amino acid sequences of monobodies, with the wild-type FN3 sequence as a reference. Mutated residues are colored in red. The dissociation constants ($K_D$) determined using yeast surface display are shown. The sequences shown correspond to SEQ ID NOS:91, 8, 52, 62, 74, 81, and 87, respectively. (b) Binding titration curves and the dissociation constants ($K_D$) of the monobodies measured using purified samples. The median fluorescence intensities of streptavidin-coated beads harboring biotinylated monobody are plotted as a function of BgaD-D concentration. The errors shown are the standard deviations from curve fitting of the 1:1 binding model. (c) Competition binding experiments using purified monobodies. Binding of monobodies indicated above each panel to BgaD-D in the presence and absence of competitor monobodies is shown. The BgaD-D concentration used was 10 nM for Mb(BgaD_L02) and Mb(BgaD_S10), 30 nM for Mb(BgaD_L14) and Mb(BgaD_L23), 40 nM for Mb(BgaD_L19) or 180 nM for Mb(BgaD_S09). The monobody concentration used as a competitior was 200× the $K_D$ value for the interaction of each monobody with BgaD-D. (d) ONPG hydrolysis activity of BgaD-D in the absence or presence of monobodies. The absorbance changes at 405 nm after the hydrolysis reaction for 10 min at 25° C. are shown. The absorbance change for the blank reaction containing ONPG but no BgaD-D or monobodies has been subtracted. A subset of these results is shown in FIG. 2C.

DETAILED DESCRIPTION OF THE INVENTION

Figure 3D:
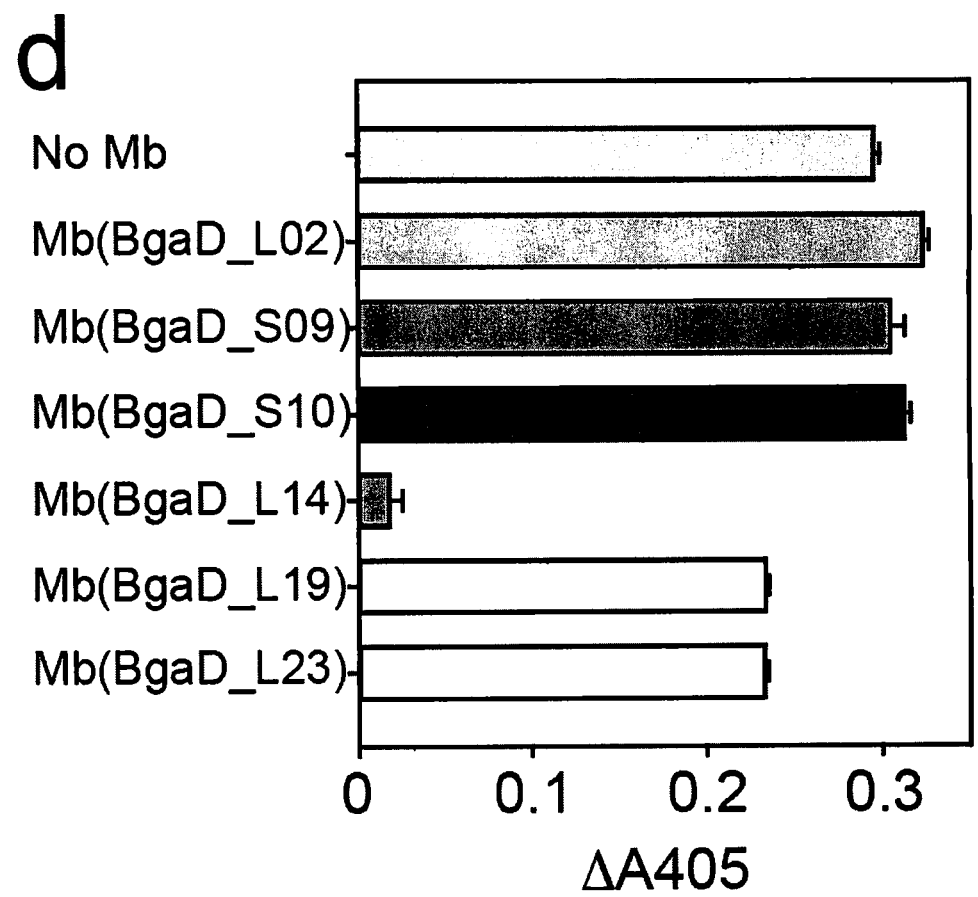

The ability to generate enzyme modifiers has applications in biochemistry and industry. Typically, modifying substrate specificity of an enzyme requires at least some information regarding the enzyme's three-dimensional structure. However, sometimes the three-dimensional structure is not available and/or difficult to achieve. Described herein are methods for developing novel enzyme substrate specificity modifiers that can be generated in the absence of any knowledge regarding the enzyme's structure. Also described herein are polypeptides that bind to β-galactosidase and polypeptides that are inhibitors and specificity modifiers of β-galactosidase. Also described herein are polypeptides that bind to lipase 1 and polypeptides that are inhibitors and specificity modifiers of lipase 1.

I. Enzyme Binding Proteins

In some embodiments, the enzyme binding protein is one that is identified from a library of enzyme binding proteins, wherein the proteins of the library have different binding specificities. In some embodiments, the enzyme binding protein is CDR-based. The term "CDR-based" refers to proteins that employ sequences and/or binding mechanisms that are the same or similar to CDRs (complementary determining region) from an antibody. In some embodiments, the EBP is an antibody mimetic. Antibody mimetics are organic compounds that, like antibodies, can specifically bind antigens, but that are not structurally related to antibodies. They are usually artificial peptides or proteins with a molar mass of about 3 to 20 kDa. Nucleic acids and small molecules are sometimes considered antibody mimetics as well, but not artificial antibodies, antibody fragments and fusion proteins composed from these. Some types have an antibody-like beta-sheet structure. Common advantages over antibodies are better solubility, tissue penetration, stability towards heat and enzymes, and comparatively low production costs. In some embodiments, the advantage of using an antibody mimetic over antibodies relates to the smaller size of the mimetic.

A. Monobodies

In some embodiments, the EBP is a monobody. Monobodies, also known as Adnectins, are genetically engineered proteins that are able to bind to antigens (Koide et al. 1998). Despite their name, they are not parts of antibodies, which make them a type of antibody mimetic. Monobodies may consist of 94 amino acids and have a molecular mass of about 10 kDa, fifteen times smaller than an IgG type antibody and comparable to the size of a single variable domain of an antibody. They are based on the structure of human fibronectin, more specifically on its tenth extracellular type III domain.

Fibronectin is a high-molecular weight (approximately 440 kDa) extracellular matrix glycoprotein that binds to membrane-spanning receptor proteins called integrins (Pankov et al., 2002). Fibronectin exists as a dimer, consisting of two nearly identical polypeptide chains linked by a pair of C-terminal disulfide bonds (Mao and Schwarzbauer, 2005). Each fibronectin monomer contains three types of modules: type I, II, and III. All three modules are composed of two anti-parallel β-sheets; however, type I and type II are stabilized by intra-chain disulfide bonds, while type III modules do not contain any disulfide bridges. The absence of disulfide bonds in type III modules allows them to partially unfold under applied force (Erickson, 2002).

The modules are arranged into several functional and protein-binding domains along the length of a fibronectin monomer. Modules $III_{9-10}$ correspond to the "cell-binding domain" of fibronectin. The RGD sequence (Arg-Gly-Asp) is located in $III_{10}$ and is the site of cell attachment via α5β1 and αVβ3 integrins on the cell surface. The "synergy site" is in $III_9$ and has a role in modulating fibronectin's association with α5β1 integrins (Sechler et al., 1997).

One of the three fibronectin binding domains, the FN3 domain, is about 100 amino acids long and possesses a beta sandwich structure having seven beta strands (strands A, B, C, D, E, F, and G) and has been established as an effective non-antibody, "alternative" scaffold for the generation of novel binding proteins. A member of the immunoglobulin superfamily, FN3 has three surface exposed loops at one end of the molecule. Engineering strategies using this scaffold are based on combinatorial libraries created by diversifying both the length and amino acid sequence of the surface loops. From such libraries, FN3 variants capable of binding to a target of interest can be isolated using various selection methods. The utility of the FN3 scaffold has been demonstrated in producing high-affinity binding proteins to a number of different protein targets (See, for example, Gilbreth R N, et al., *J Mol Biol.* 2008; 381:407-18; Gilbreth R N, et al., *Proc Natl Acad Sci USA.* 2011; 108:7751-6; Grebien F, et al., *Cell.* 2011; 147:306-19; Koide A, et al., *Proc Natl Acad Sci USA.* 2002; 99:1253-8; Koide A, et al., *J Mol Biol.* 1998; 284:1141-51; Koide A, et al., *Proc Natl Acad Sci USA.* 2007; 104:6632-7; Koide A, et al., *J Mol Biol.* 2012; 415:393-405; Sha F, et al., *Proc Natl Acad Sci USA.* 2013; 110:14924-9; and Wojcik J, et al., *Nat Struct Mol Biol.* 2010; 17:519-27, each of which are incorporated by reference for all purposes). These binding proteins generated from this scaffold are referred to as monobodies. With its lack of disulfide bonds, ease of high-level expression in bacterial systems, and small size, the FN3 scaffold offers many advantages compared to conventional antibodies or fragments thereof. One example of a FN3 polypeptide or scaffold has the amino acid sequence (SEQ ID NO: 91)
Val Ser Asp Val Pro Arg Asp Leu Glu Val Val Ala Ala Thr Pro Thr Ser Leu Leu Ile Ser Trp Asp Ala Pro Ala Val Thr Val Arg Tyr Tyr Arg Ile Thr Tyr Gly Glu Thr Gly Gly Asn Ser Pro Val Gln Glu Phe Thr Val Pro Gly Ser Lys Ser Thr Ala Thr Ile Ser Gly Leu Lys Pro Gly Val Asp Tyr Thr Ile Thr Val Tyr Ala Val Thr Gly Arg Gly Asp Ser Pro Ala Ser Ser Lys Pro Ile Ser Ile Asn Tyr Arg Thr.

In certain aspects, the FN3 scaffold or body comprises beta strand A, beta strand B, beta strand C, beta strand D, beta strand E, beta strand F, and beta strand G. Connecting beta strands A, B, C, D, E, F, and G are loop regions AB (15-16), BC (22 to 30), CD (39-45), DE (51-55), EF (60-66), and FG (76-87). Beta strand A precedes the AB loop and beta strand G follows the FG loop.

FN3 polypeptides can be modified by inserting or deleting 1, 2, 3, 4, 5, 6, 7, 8, 9, 10, 20 or more amino acids, or any range derivable therein, in a FN3 loop. Variants are discussed in U.S. Pat. No. 6,673,901, which is hereby incorporated by reference with respect to embodiments regarding FN3 monobodies.

A combinatorial library is a collection of diverse compounds generated by either chemical synthesis or biological synthesis by combining a number of chemical "building blocks." For example, a linear combinatorial chemical library such as a polypeptide (e.g., mutein or variant) library is formed by combining a set of chemical building blocks called amino acids in every possible way for a given compound length. Millions of compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al., 1994).

Embodiments of the disclosure are directed to the use of a combinatorial library of FN3 domains. In certain aspects, polypeptides of the library include variations of amino acid sequence in one or more of the beta strands or body of the FN3 domains. In certain aspects, the library includes variations of amino acid sequences in one or more loops of the FN3 domains. In still further aspects, the library includes variation in both loops and beta strands of the FN3 domain.

FN3 variants can include alanine substitutions at one or more of amino acid positions. Substitutions include, but are not limited to conservative substitutions that have little or no effect on the overall net charge, polarity, or hydrophobicity of the protein.

In certain aspects, FN3 domains will have 1, 2, 3, 4, 5, 6, 7, 8, 9, 10, 11, 12, 13, 14, 15, 16, 17, 18, 19, 20, 21, 22, 23, 24, or 25 amino acid substitutions that include, but are not limited to the following FN3 residue substitutions (corresponding to SEQ ID NO:91): R30A, R30N, R30D, R30C, R30Q, R30E, R30G, R30H, R30I, R30L, R30K, R30M, R30F, R30P, R30S, R30T, R30W, R30Y, R30V, Y31A, Y31R, Y31N, Y31D, Y31C, Y31Q, Y31E, Y31G, Y31H, Y31I, Y31L, Y31K, Y31M, Y31F, Y31P, Y31S, Y31T, Y31W, Y31V, R33A, R33N, R33D, R33C, R33Q, R33E, R33G, R33H, R33I, R33L, R33K, R33M, R33F, R33P, R33S, R33T, R33W, R33Y, R33V, T35A, T35R, T35N, T35D, T35C, T35Q, T35E, T35G, T35H, T35I, T35L, T35K, T35M, T35F, T35P, T35S, T35W, T35Y, T35V, G41A, G41R, G41N, G41D, G41C, G41Q, G41E, G41H, G41I, G41L, G41K, G41M, G41F, G41P, G41S, G41T, G41W, G41Y, G41V, N42A, N42R, N42D, N42C, N42Q, N42E, N42G, N42H, N42I, N42L, N42K, N42M, N42F, N42P, N42S, N42T, N42W, N42Y, N42V, S43A, S43R, S43N, S43D, S43C, S43Q, S43E, S43G, S43H, S43I, S43L, S43K, S43M, S43F, S43P, S43T, S43W, S43Y, S43V, P44A, P44R, P44N, P44D, P44C, P44Q, P44E, P44G, P44H, P44I, P44L, P44K, P44M, P44F, P44S, P44T, P44W, P44Y, P44V, V45A, V45R, V45N, V45D, V45C, V45Q, V45E, V45G, V45H, V45I, V45L, V45K, V45M, V45F, V45P, V45S, V45T, V45W, V45Y, E47A, E47R, E47N, E47D, E47C, E47Q, E47G, E47H, E47I, E47L, E47K, E47M, E47F, E47P, E47S, E47T, E47W, E47Y, E47V, T49A, T49R, T49N, T49D, T49C, T49Q, T49E, T49G, T49H, T49I, T49L, T49K, T49M, T49F, T49P, T49S, T49W, T49Y, T49V, V50A, V50R, V50N, V50D, V50C, V50Q, V50E, V50G, V50H, V50I, V50L, V50K, V50M, V50F, V50P, V50S, V50T, V50W, V50Y, T71A, T71R, T71N, T71D, T71C, T71Q, T71E, T71G, T71H, T71I, T71L, T71K, T71M, T71F, T71P, T71S, T71W, T71Y, T71V, Y73A, Y73R, Y73N, Y73D, Y73C, Y73Q, Y73E, Y73G, Y73H, Y73I, Y73L, Y73K, Y73M, Y73F, Y73P, Y73S, Y73T, Y73W, Y73V, V75A, V75R, V75N, V75D, V75C, V75Q, V75E, V75G, V75H, V75I, V75L, V75K, V75M, V75F, V75P, V75S, V75T, V75W, V75Y, T76A, T76R, T76N, T76D, T76C, T76Q, T76E, T76G, T76H, T76I, T76L, T76K, T76M, T76F, T76P, T76S, T76W, T76Y, T76V, G77A, G77R, G77N, G77D, G77C, G77Q, G77E, G77H, G77I, G77L, G77K, G77M, G77F, G77P, G77S, G77T, G77W, G77Y, G77V, R78A, R78N, R78D, R78C, R78Q, R78E, R78G, R78H, R78I, R78L, R78K, R78M, R78F, R78P, R78S, R78T, R78W, R78Y, R78V, G79A, G79R, G79N, G79D, G79C, G79Q, G79E, G79H, G79I, G79L, G79K, G79M, G79F, G79P, G79S, G79T, G79W, G79Y, G79V, D80A, D80R, D80N, D80C, D80Q, D80E, D80G, D80H, D80I, D80L, D80K, D80M, D80F, D80P, D80S, D80T, D80W, D80Y, D80V, S81A, S81R, S81N, S81D, S81C, S81Q, S81E, S81G, S81H, S81I, S81L, S81K, S81M, S81F, S81P, S81T, S81W, S81Y, S81V, P82A, P82R, P82N, P82D, P82C, P82Q, P82E, P82G, P82H, P82I, P82L, P82K, P82M, P82F, P82S, P82T, P82W, P82Y, P82V, A83R, A83N, A83D, A83C, A83Q, A83E, A83G, A83H, A83I, A83L, A83K, A83M, A83F, A83P, A83S, A83T, A83W, A83Y, A83V, S84A, S84R, S84N, S84D, S84C, S84Q, S84E, S84G, S84H, S84I, S84L, S84K, S84M, S84F, S84P, S84T, S84W, S84Y, S84V, S85A, S85R, S85N, S85D, S85C, S85Q, S85E, S85G, S85H, S85I, S85L, S85K, S85M, S85F, S85P, S85T, S85W, S85Y, and S85V.

In still further embodiments other amino acid substitutions can be introduced before, during, or after introduction of those amino acid substitutions listed above. The other substitutions (corresponding to SEQ ID NO:91) include, but is not limited to 1, 2, 3, 4, 5, 6, 7, 8, 9, 10, 11, or 12 of W22A, W22R, W22N, W22D, W22C, W22Q, W22E, W22G, W22H, W22I, W22L, W22K, W22M, W22F, W22P, W22S, W22T, W22Y, W22V, D23A, D23R, D23N, D23C, D23Q, D23E, D23G, D23H, D23I, D23L, D23K, D23M, D23F, D23P, D23S, D23T, D23W, D23Y, D23V, A24R, A24N, A24D, A24C, A24Q, A24E, A24G, A24H, A24I, A24L, A24K, A24M, A24F, A24P, A24S, A24T, A24W, A24Y, A24V, P25A, P25R, P25N, P25D, P25C, P25Q, P25E, P25G, P25H, P25I, P25L, P25K, P25M, P25F, P25S, P25T, P25W, P25Y, P25V, A26R, A26N, A26D, A26C, A26Q, A26E, A26G, A26H, A26I, A26L, A26K, A26M, A26F, A26P, A26S, A26T, A26W, A26Y, A26V, V27A, V27R, V27N, V27D, V27C, V27Q, V27E, V27G, V27H, V27I, V27L, V27K, V27M, V27F, V27P, V27S, V27T, V27W, V27Y, T28A, T28R, T28N, T28D, T28C, T28Q, T28E, T28G, T28H, T28I, T28L, T28K, T28M, T28F, T28P, T28S, T28W, T28Y, T28V, V29A, V29R, V29N, V29D, V29C, V29Q, V29E, V29G, V29H, V29I, V29L, V29K, V29M, V29F, V29P, V29S, V29T, V29W, V29Y, G52A, G52R, G52N, G52D, G52C, G52Q, G52E, G52H, G52I, G52L, G52K, G52M, G52F, G52P, G52S, G52T, G52W, G52Y, G52V, S53A, S53R, S53N, S53D, S53C, S53Q, S53E, S53G, S53H, S53I, S53L, S53K, S53M, S53F, S53P, S53T, S53W, S53Y, S53V, K54A, K54R, K54N, K54D, K54C, K54Q, K54E, K54G, K54H, K54I, K54L, K54M, K54F, K54P, K54S, K54T, K54W, K54Y, K54V, S55A, S55R, S55N, S55D, S55C, S55Q, S55E, S55G, S55H, S55I, S55L, S55K, S55M, S55F, S55P, S55T, S55W, S55Y, or S55V.

In certain aspects, the library comprises a variation in an amino acid corresponding to amino acid 30, 31, 33, 35, 41, 42, 43, 44, 45, 47, 49, 50, 71, 73, 75, 76, 77, 78, 79, 80, 81, 82, 83, 84, and/or 85 of SEQ ID NO:91 in combination with one or more residue corresponding to amino acid 30, 31, 33, 35, 41, 42, 43, 44, 45, 47, 49, 50, 71, 73, 75, 76, 77, 78, 79, 80, 81, 82, 83, 84, and/or 85.

B. Antibodies

In some embodiments, the EBP is an antibody. The antibody can be any of the various antibodies described herein, non-limiting, examples of such include a polyclonal antibody, a monoclonal antibody, a chimeric antibody, a human antibody, a veneered antibody, a diabody, a humanized antibody, an antibody derivative, a recombinant humanized antibody, a nanobody, a heavy-chain only antibody (e.g. from camelids such as camel, llama, alpaca, etc.) or a derivative or fragment of each thereof.

Antibodies can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum. Common variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit, Rev. Biotechnol. 16:95-118; Eren et al. (1998) Mumma 93:154-161 that are capable of producing a repertoire of human antibodies, as known in the art and/or as described herein. Such techniques, include, but are not limited to, ribosome display Wanes et al. (1997) Proc. Natl. Acad. Sci. USA, 94:4937-4942; Hanes et al, (1998) Proc. Natl. Acad. Sci. USA 95:14130-14135); single cell antibody producing technologies (e.g., selected lymphocyte antibody method ("SLAM") (U.S. Pat. No. 5,627,052, Wen et al, (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al, (1995) Bio. Technol. 13:787-790); B-cell selection (Steenbakkers et al. (1994) Molec. Biol. Reports 19:125-134).

C. Affibodies

In some embodiments, the EBP is an affibody. Affibody molecules are small proteins engineered to bind to a large number of target proteins or peptides with high affinity, imitating monoclonal antibodies, and are therefore a member of the family of antibody mimetics. Affibody molecules are based on a three-helix bundle domain, which can be expressed in soluble and proteolytically stable forms in various host cells on its own or via fusion with other protein partners. They tolerate modification and are independently folding when incorporated into fusion proteins. Head-to-tail fusions of Affibody molecules of the same specificity have proven to give avidity effects in target binding, and head-to-tail fusion of Affibody molecules of different specificities makes it possible to get bi- or multi-specific affinity proteins. Fusions with other proteins can also be created. A site for site-specific conjugation is facilitated by introduction of a single cysteine at a desired position.

A number of different Affibody molecules have been produced by chemical synthesis. Since they do not contain cysteines or disulfide bridges, they fold spontaneously and reversibly into the correct three-dimensional structures when the protection groups are removed after synthesis.

An Affibody molecule consists of three alpha helices with 58 amino acids and has a molar mass of about 6 kDa. Affibody molecules have been shown to withstand high temperatures (90° C.) or acidic and alkaline conditions (pH 2.5 or pH 11, respectively). Binders with an affinity of down to sub-nanomolar have been obtained from naïve library selections, and binders with picomolar affinity have been obtained following affinity maturation.

D. Anticalins

In some embodiments, the EBP is an anticalin. Anticalins are artificial proteins that are able to bind to antigens, either to proteins or to small molecules. They are not structurally related to antibodies, which makes them a type of antibody mimetic. Instead, they are derived from human lipocalins which are a family of naturally binding proteins. Anticalins can be used in place of monoclonal antibodies, but are about eight times smaller with a size of about 180 amino acids and a mass of about 20 kDa.

Anticalins have better tissue penetration than antibodies and are stable at temperatures up to 70° C. Unlike antibodies, they can be produced in bacterial cells like *E. coli* in large amounts. While antibodies can only be directed at macromolecules such as proteins and at small molecules (haptens) only if bound to macromolecules, anticalins are able to selectively bind to small molecules as well.

Characteristic for anticalins is their barrel structure formed by eight antiparallel β-strands pairwise connected by loops and an attached α-helix. The main structure of anticalins is identical to wild type lipocalins. Conformational deviations are primarily located in the four loops reaching in the ligand binding site. Mutagenesis of amino acids at the binding site allows for changing the affinity and selectivity.

E. Kunitz Variants

In some embodiments, the EBP is a Kunitz variant. Kunitz domains are the active domains of proteins that inhibit the function of protein degrading enzymes or, more specifically, domains of Kunitz-type are protease inhibitors. They are relatively small with a length of about 50 to 60 amino acids and a molecular weight of 6 kDa. Examples of Kunitz-type protease inhibitors are aprotinin (bovine pancreatic trypsin inhibitor, BPTI), Alzheimer's amyloid precursor protein (APP), and tissue factor pathway inhibitor (TFPI).

The structure is a disulfide rich alpha+beta fold. Bovine pancreatic trypsin inhibitor is an extensively studied model structure. Certain family members are similar to the tick anticoagulant peptide (TAP, P17726). This is a highly selective inhibitor of factor Xa in the blood coagulation pathways. TAP molecules are highly dipolar, and are arranged to form a twisted two-stranded antiparallel beta sheet followed by an alpha helix.

The majority of the sequences having this domain belong to the MEROPS inhibitor family I2, clan IB; the Kunitz/bovine pancreatic trypsin inhibitor family, they inhibit proteases of the S1 family and are restricted to the metazoa with a single exception: Amsacta moorei entomopoxvirus, a species of poxvirus. They are short (about 50 to 60 amino acid residues) alpha/beta proteins with few secondary structures. The fold is constrained by three disulfide bonds. The type example for this family is BPTI (or basic protease inhibitor), but the family includes numerous other members, such as snake venom basic protease; mammalian inter-alpha-trypsin inhibitors; trypstatin, a rat mast cell inhibitor of trypsin; a domain found in an alternatively spliced form of Alzheimer's amyloid beta-protein; domains at the C-termini of the alpha-1 and alpha-3 chains of type VI and type VII collagens; tissue factor pathway inhibitor precursor; and Kunitz STI protease inhibitor contained in legume seeds.

Kunitz domains are stable as standalone peptides, able to recognise specific protein structures, and also work as competitive protease inhibitors in their free form. These properties are useful for developing EBPs. Candidate EBPs are selected from molecular libraries containing over 10 million variants with the aid of display techniques like phage display, and can be produced in large scale by genetically engineered organisms.

F. DARPins

In some embodiments, the EPB is a DARPin. DARPins (an acronym for designed ankyrin repeat proteins) are genetically engineered antibody mimetic proteins typically exhibiting highly specific and high-affinity target protein binding. They are derived from natural ankyrin proteins and consist of at least three, usually four or five repeat motifs of these proteins. Their molecular mass is about 14 or 18 kDa (kilodaltons) for four- or five-repeat DARPins, respectively.

DARPins are derived from naturally occurring ankyrin proteins, a protein class that is mediating high-affinity protein-protein interactions in nature. Sequence alignments of several thousand natural ankyrin repeat motifs (of about 33 amino acids each) combined with structure based design and recombinant DNA methods is used for generation of these proteins. DARPins are composed of repetitive structural units forming a stable protein domain with a large potential target interaction surface. Typically, DARPins are composed of four or five repeats, corresponding to the average size of natural ankyrin repeat protein domains. Proteins with less than three repeats do not form a tertiary structure. The molecular mass depending on the number of repeats is as follows:

| | Repeats | | | | | |
| --- | --- | --- | --- | --- | --- | --- |
| | 3 | 4 | 5 | 6 | 7 | ... |
| Approximate mass (kDa) | 10 | 14 | 18 | 22 | 26 | ... |

Libraries of DARPins with randomized potential target interaction residues with diversities of over 1012 variants have been generated at the DNA level. From these libraries, DARPins binding the target of choice with picomolar affinity and specificity can be selected using ribosome display or signal recognition particle (SRP) phage display.

DARPins are expressed in the cytoplasm of *Escherichia coli* at high levels (over 10 g/l in fermentation, 1 g/l in shake flask) in soluble form. The proteins exhibit high thermal and thermodynamic stability (denaturation midpoint: Tm>66° C., equilibrium unfolding: ΔG>9.5 kcal/mol), which is increasing with increasing repeat number. DARPins are stable in human blood serum and do not contain T-cell epitopes. The high specificity and affinity of binding DARPins has been attributed rigid body binding mode. Multi-specific or multi-valent constructs made by genetic fusion show similar properties as single domain DARPins. The absence of cysteines in the scaffold enables engineering of site-specific cysteines, allowing site-directed coupling of chemicals to the molecule.

G. Other EBP Scaffolds

Other some embodiments, the EBP is one known in the art. Further examples include affilins, affimers, affitins, alphabodies, avimers, and fynomers.

H. Library Screening

Library screening can be conducted in order to select EBPs that bind to specific ligands or targets and/or confer a specific activity modification (e.g. substrate specificity modifier, inhibitor, etc. . . . ) to the target (i.e. enzyme). Combinatorial screening can easily produce and screen a large number of EBPs, which is not feasible with specific mutagenesis ("rational design") approaches. EBPs with desired binding capabilities can be selected in vitro, recovered and amplified. The amino acid sequence of a selected clone can be identified readily by sequencing the nucleic acid encoding the selected EBP.

In some embodiments, a particular EBP has an affinity for a target that is at least 2-fold greater than the affinity of the polypeptide prior to substitutions discussed herein. In some embodiments, the affinity is, is at least, or is at most about 2-, 3-, 4-, 5-, 6-, 7-, 8-, 9-, 10-, 15-, 20-, 25-, 30-, 35-, 40-, 45-, 50-, 60-, 70-, 80-, 90-, 100-fold increased compared to another FN3-based molecule.

Library construction of various different types of EBPs are known in the art, and are also available commercially for purchase. For example, Koide and Koide, *Methods Mol. Biol.*, 352:95-109, 2007, which is herein incorporated by reference, describes construction of monobody libraries.

II. Polypeptide Compositions

The present invention concerns methods and compositions related to the identification and use of monobodies and/or other binding polypeptides. In some embodiments, the binding polypeptide and/or monobody is an enzyme binding polypeptide (EBP). As used herein, a "monobody"

is a polypeptide that binds to a specific antigen or antigens of another protein. As used herein, a "polypeptide" generally is defined herein to refer to a peptide sequence of about 10 to about 1,000 or more amino acid residues.

In certain embodiments, the polypeptide is a fusion polypeptide that is linked at the N- or C-terminus to a second peptide or polypeptide. The second polypeptide may be another binding polypeptide or a detectable label, for example. In other embodiments, the polypeptide comprises a linker interposed between the binding polypeptide and the second peptide or polypeptide sequence. Linkers are discussed in greater detail in the specification below.

Furthermore, the polypeptides set forth herein may comprise a sequence of any number of additional amino acid residues at either the N-terminus or C-terminus of the amino acid sequence. For example, there may be an amino acid sequence of about 3 to about 1,000 or more amino acid residues at either the N-terminus, the C-terminus, or both the N-terminus and C-terminus of the amino acid sequence that includes the binding polypeptide.

The polypeptide may include the addition of an antibody epitope or other tag, to facilitate identification, targeting, and/or purification of the polypeptide. The use of 6×His and GST (glutathione S transferase) as tags is well known. Inclusion of a cleavage site at or near the fusion junction will facilitate removal of the extraneous polypeptide after purification. Other amino acid sequences that may be included in the polypeptide include functional domains, such as active sites from enzymes such as a hydrolase, glycosylation domains, cellular targeting signals or transmembrane regions. The polypeptide may further include one or more additional tissue-targeting moieties.

Polypeptides may possess deletions and/or substitutions of amino acids relative to the native sequence. Sequences with amino acid substitutions are contemplated, as are sequences with a deletion, and sequences with a deletion and a substitution. In some embodiments, these polypeptides may further include insertions or added amino acids.

Substitutional or replacement variants typically contain the exchange of one amino acid for another at one or more sites within the protein and may be designed to modulate one or more properties of the polypeptide, particularly to increase its efficacy or specificity. Substitutions of this kind may or may not be conservative substitutions. Conservative substitution is when one amino acid is replaced with one of similar shape and charge. In embodiments wherein the binding polypeptide is a monobody library, the monobody library serves to provide a diversity of amino acid sequences and binding selectivity conservative substitutions are not required. However, if used, conservative substitutions are well known in the art and include, for example, the changes of alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Changes other than those discussed above are generally considered not to be conservative substitutions. It is specifically contemplated that one or more of the conservative substitutions above may be included as embodiments. In some embodiments, such substitutions are specifically excluded. Furthermore, in additional embodiments, substitutions that are not conservative are employed in variants.

In addition to a deletion or substitution, the polypeptides may possess an insertion of one or more residues.

The binding polypeptide sequence may be structurally equivalent to the native counterparts. For example, the binding polypeptide sequence forms the appropriate structure and conformation for binding targets, proteins, or peptide segments.

The following is a discussion based upon changing of the amino acids of a polypeptide to create a library of molecules or a second-generation molecule. For example, certain amino acids may be substituted for other amino acids in a polypeptide without appreciable loss of function, such as ability to interact with a target peptide sequence. Since it is the interactive capacity and nature of a polypeptide that defines that polypeptide's functional activity, certain amino acid substitutions can be made in a polypeptide sequence and nevertheless produce a polypeptide with like properties.

In making such changes, the hydropathic index of amino acids may be considered. The importance of the hydropathic amino acid index in conferring interactive function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. However, in some aspects a non-conservative substitution is contemplated. In certain aspects a random substitution is also contemplated. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's GenBank and GenPept databases (on the World Wide Web at ncbi.nlm.nih.gov/). The all or part of the coding regions for these genes may be amplified and/or expressed using the techniques disclosed herein or as would be known to those of ordinary skill in the art.

Amino acid sequence variants of other polypeptides of these compositions can be substitutional, insertional, or deletion variants. A modification in a polypeptide may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 or more non-contiguous or contiguous amino acids of a peptide or polypeptide, as compared to the original polypeptide.

Proteins may be recombinant, or synthesized in vitro. Alternatively, a recombinant protein may be isolated from bacteria or other host cell.

The term "functionally equivalent codon" is used herein to refer to codons that encode the same amino acid, such as the six codons for arginine or serine, and also refers to codons that encode biologically equivalent amino acids.

It also will be understood that amino acid and nucleic acid sequences may include additional residues, such as additional N- or C-terminal amino acids, or 5' or 3' nucleic acid sequences, respectively, and yet still be essentially as set forth in one of the sequences disclosed herein, so long as the sequence meets the criteria set forth above, including the maintenance of biological protein activity. The addition of terminal sequences particularly applies to nucleic acid sequences that may, for example, include various non-coding sequences flanking either of the 5' or 3' portions of the coding region.

It is contemplated that in composition embodiments, there is between about 0.001 mg and about 10 mg of total protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 50, 100 .mu·g/ml or mg/ml or more (or any range derivable therein).

The polypeptides described herein may be fused, conjugated, or operatively linked to a label. As used herein, the term "label" intends a directly or indirectly detectable compound or composition that is conjugated directly or indirectly to the composition to be detected, e.g., polynucleotide or protein to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluoresecence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6.sup.th ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6.sup.th ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Attachment of the fluorescent label may be either directly to the cellular component or compound or alternatively, can by via a linker. Suitable binding pairs for use in indirectly linking the fluorescent label to the intermediate include, but are not limited to, antigens/antibodies, e.g., rhodamine/anti-rhodamine, biotin/avidin and biotin/strepavidin.

III. Polynucleotides

Aspects of the disclosure relate to polypeptides and polynucleotides encoding such polypeptides. The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of the disclosure that is a polynucleotide encompasses both the double-stranded form and each of two complementary single-stranded forms known or predicted to make up the double-stranded form.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'. It will be recognized by one of skill in the art that two complementary nucleotide sequences include a sense strand and an antisense strand.

Polypeptides may be encoded by a nucleic acid molecule in the composition. In certain embodiments, the nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce an antibody.

The term "expression vector" refers to a vector containing a nucleic acid sequence coding for at least part of a gene product capable of being transcribed or stably integrate into a host cell's genome and subsequently be transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein. It is contemplated that expression vectors that express a marker may be useful in the invention. In other embodiments, the marker is encoded on an mRNA and not in an expression vector.

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

The particular promoter that is employed to control the expression of a peptide or protein encoding polynucleotide is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter. In some embodiments, the host cell is an eukaryotic cell. In some embodiments, using eukaryotic cells is beneficial, as it provides for secondary modifications that may not be present in certain prokaryotic systems.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.)

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

The vectors or constructs will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels. In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

In expression, particularly eukaryotic expression, one will typically include a polyadenylation signal to effect proper polyadenylation of the transcript.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The polynucleotides and polypeptides of the disclosure may be transfected of transformed into host cells or expressed in host cells. As used herein, the terms "cell," "cell line," and "cell culture" may be used interchangeably. All of these terms also include both freshly isolated cells and ex vivo cultured, activated or expanded cells. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny. Common host cells include bacteria (such as *E. coli, B. subtilis, S. viofoceoruber*), yeast (such as *S. cerevisiae, P. pastoris*), fungi (such as *A. oryzae*) or eukaryotic cells.

IV. Kits

Kits are also contemplated as being made or used in certain aspects of the disclosure. For instance, a polypeptide or nucleic acid of the disclosure can be included in a kit. A kit can be included in a sealed container. Non-limiting examples of containers include a microtiter plate, a bottle, a metal tube, a laminate tube, a plastic tube, a dispenser, a pressurized container, a barrier container, a package, a compartment, or other types of containers such as injection or blow-molded plastic containers into which the dispersions or compositions or desired bottles, dispensers, or packages are retained. Other examples of containers include glass or plastic vials or bottles. The kit and/or container can include indicia on its surface. The indicia, for example, can be a word, a phrase, an abbreviation, a picture, or a symbol.

The containers can dispense or contain a pre-determined amount of a composition of the disclosure. The composition can be dispensed as a liquid, a fluid, or a semi-solid. A kit can also include instructions for using the kit and/or compositions. Instructions can include an explanation of how to use and maintain the compositions.

Kits may also include libraries of binding polypeptides (e.g. monobody libraries) and instructions for identifying enzyme substrate modifiers, inhibitors, and/or binding proteins. The kits may include additional components such as buffers, diluents, and specific assay compents to determine enzyme activity and/or enzyme substrate specificity.

Table 1 describes polypeptides of the disclosure.

TABLE 1

| SEQ ID NO: | Amino Acid Sequence |
|---|---|
| | 10・  20・  30 BC βC  40 •CD |
| 91 | VSDVPRDLEVVAATPTSLLISWDA<u>PAVT</u>----<u>VR</u>YYRITYGETGGNSPV-- |
| 1 | VS<u>S</u>VP<u>TK</u>LEVVAATPTSLLISWDA<u>MDHTPY</u>--<u>VY</u>YYRITYGETGGNSPV-- |
| 2 | VS<u>S</u>VP<u>TK</u>LEVVAATPTSLLISWDA<u>IFWS</u>----<u>VA</u>YYRITYGETGGNSPV-- |
| 3 | VS<u>S</u>VP<u>TK</u>LEVVAATPTSLLISWDA<u>GQSY</u>----<u>VY</u>YYRITYGETGGNSPV-- |
| 4 | VS<u>S</u>VP<u>TK</u>LEVVAATPTSLLISWDA<u>YFWGWYYSV</u>W<u></u>YRITYGETGGNSPV-- |
| 5 | VS<u>S</u>VP<u>TK</u>LEVVAATPTSLLISWDA<u>GVKGWNY</u>-<u>VD</u>YYRITYGETGGNSPV-- |
| 6 | VS<u>S</u>VP<u>TK</u>LEVVAATPTSLLISWDA<u>DYYN</u>----<u>VM</u>YYRITYGETGGNSPV-- |

TABLE 1-continued

| SEQ ID NO: | Amino Acid Sequence |
|---|---|
| 7 | VS<u>S</u>VP<u>TK</u>LEVVAATPTSLLISWDAP<u>VYWNH</u>--<u>V</u>NYYRITYGETGGNSPV-- |
| 8 | VS<u>S</u>VP<u>TK</u>LEVVAATPTSLLISWDA<u>NGWNY</u>---<u>VK</u>YYRITYGETGGNSPV-- |
| 9 | VS<u>S</u>VP<u>TK</u>LEVVAATPTSLLISWDA<u>QGWNY</u>---<u>VQ</u>YYRITYGETGGNSPV-- |
| 10 | VS<u>S</u>VP<u>TK</u>LEVVAATPTSLLISWDA<u>WASFNY</u>--<u>VS</u>YYRITYGETGGNSPV-- |
| 11 | VS<u>S</u>VP<u>TK</u>LEVVAATPTSLLISWDA<u>SGWNY</u>---<u>VS</u>YYRITYGETGGNSPV-- |
| 12 | VS<u>S</u>VP<u>TK</u>LEVVAATPTSLLISWDA<u>YGWNY</u>---<u>VS</u>YYRITYGETGGNSPV-- |
| 13 | VS<u>S</u>VP<u>TK</u>LEVVAATPTSLLISWDA<u>WASFNY</u>--<u>VS</u>YYRITYGETGGNSPV-- |
| 14 | VS<u>S</u>VP<u>TK</u>LEVVAATPTSLLISWDA<u>GDYW</u>----<u>VY</u>YYRITYGETGGNSPV-- |
| 15 | VS<u>S</u>VP<u>TK</u>LEVVAATPTSLLISWDA<u>QGYP</u>----<u>VY</u>YYRITYGETGGNSPV-- |
| 16 | VS<u>S</u>VP<u>TK</u>LEVVAATPTSLLISWDA<u>YYGD</u>----<u>VY</u>YYRITYGETGGNSPV-- |
| 17 | VS<u>S</u>VP<u>TK</u>LEVVAATPTSLLISWDA<u>SSSS</u>----<u>VS</u>YYRITYGETGGNSPV-- |
| 18 | VS<u>S</u>VP<u>TK</u>LEVVAATPTSLLISWDA<u>WRGEG</u>---<u>VA</u>YYRITYGETGGNSPV-- |
| 19 | VS<u>S</u>VP<u>TK</u>LEVVAATPTSLLISWDA<u>YYPSWG</u>--<u>VS</u>YYRITYGETGGNSPV-- |
| 20 | VS<u>S</u>VP<u>TK</u>LEVVAATPTSLLISWDA<u>YSYP</u>----<u>VS</u>YYRITYGETGGNSPV-- |
| 21 | VS<u>S</u>VP<u>TK</u>LEVVAATPTSLLISWDA<u>YEHWSG</u>--<u>VY</u>YYRITYGETGGNSPV-- |
| 22 | VS<u>S</u>VP<u>TK</u>LEVVAATPTSLLISWDA<u>YEHWSG</u>--<u>VY</u>YYRITYGETGGNSPV-- |
| 23 | VS<u>S</u>VP<u>TK</u>LEVVAATPTSLLISWDA<u>YEHWSG</u>--<u>VY</u>YYRITYGETGGNSPV-- |
| 24 | VS<u>S</u>VP<u>TK</u>LEVVAATPTSLLISWDA<u>YVYQSSSD</u><u>V</u>YYRITYGETGGNSPV-- |
| 25 | VS<u>S</u>VP<u>TK</u>LEVVAATPTSLLISWDA<u>YYSPYY</u>-<u>VS</u>YYRITYGETGGNSPV-- |
| 26 | VS<u>S</u>VP<u>TK</u>LEVVAATPTSLLISWDA<u>YKSLGG</u>--<u>VD</u>YYRITYGETGGNSPV-- |
| 27 | VS<u>S</u>VP<u>TK</u>LEVVAATPTSLLISWDAPAVT---- |
| 28 | VS<u>S</u>VP<u>TK</u>LEVVAATPTSLLISWDAPAVT---- |
| 29 | VS<u>S</u>VP<u>TK</u>LEVVAATPTSLLISWDAPAVT---- |
| 30 | VS<u>S</u>VP<u>TK</u>LEVVAATPTSLLISWDAPAVT---- |
| 31 | VS<u>S</u>VP<u>TK</u>LEVVAATPTSLLISWDAPAVT---- |
| 32 | VS<u>S</u>VP<u>TK</u>LEVVAATPTSLLISWDAPAVT----V<u>VFY</u>VITYGETG<u>AVWPGY</u>- |
| 33 | VS<u>S</u>VP<u>TK</u>LEVVAATPTSLLISWDAPAVT----V<u>DLYL</u>ITYGETG<u>HSAAWP</u>- |
| 34 | VS<u>S</u>VP<u>TK</u>LEVVAATPTSLLISWDAPAVT----V<u>DLY</u>VITYGETGG<u>SGWP</u>-- |
| 35 | VS<u>S</u>VP<u>TK</u>LEVVAATPTSLLISWDAPAVT----V<u>DLY</u>VITYGETGG<u>PGWP</u>-- |
| 36 | VS<u>S</u>VP<u>TK</u>LEVVAATPTSLLISWDAPAVT----V<u>VYY</u>VITYGETG<u>HHWPGY</u>- |
| 37 | VS<u>S</u>VP<u>TK</u>LEVVAATPTSLLISWDAPAVT---- |
| 38 | VS<u>S</u>VP<u>TK</u>LEVVAATPTSLLISWDAPAVT----V<u>DLYL</u>ITYGETG<u>FSYGFP</u>- |
| 39 | VS<u>S</u>VP<u>TK</u>LEVVAATPTSLLISWDAPAVT----V<u>DFYL</u>ITYGETGG<u>PSWP</u>-- |
| 40 | VS<u>S</u>VP<u>TK</u>LEVVAATPTSLLISWDAPAVT----V<u>DFYL</u>ITYGETGG<u>PSWP</u>-- |
| 41 | VS<u>S</u>VP<u>TK</u>LEVVAATPTSLLISWDAPAVT----V<u>DLYI</u>ITYGETG<u>YVGSWP</u>- |
| 42 | VS<u>S</u>VP<u>TK</u>LEVVAATPTSLLISWDAPAVT----V<u>DLYL</u>ITYGETGG<u>FSWP</u>-- |
| 43 | VS<u>S</u>VP<u>TK</u>LEVVAATPTSLLISWDAPAVT----V<u>DLY</u>VITYGETGG<u>YSWP</u>-- |
| 44 | VS<u>S</u>VP<u>TK</u>LEVVAATPTSLLISWDAPAVT----V<u>DLYI</u>ITYGETGG<u>SAWP</u>-- |

TABLE 1-continued

| SEQ ID NO: | Amino Acid Sequence |
|---|---|
| 45 | VS<u>S</u>V<u>PT</u>KLEVVAATPTSLLISWDAPAVT----V<u>DLY</u>I<u>I</u>TYGETGG<u>SAWP</u>-- |
| 46 | VS<u>S</u>V<u>PT</u>KLEVVAATPTSLLISWDAPAVT----V<u>DFY</u>F<u>I</u>TYGETGG<u>SSWV</u>-- |
| 47 | VS<u>S</u>V<u>PT</u>KLEVVAATPTSLLISWDAPAVT----V<u>DLY</u>V<u>I</u>TYGETGG<u>SSWP</u>-- |
| 48 | VS<u>S</u>V<u>PT</u>KLEVVAATPTSLLISWDAPAVT----V<u>DLY</u>V<u>I</u>TYGETGG<u>SSWP</u>-- |
| 49 | VS<u>S</u>V<u>PT</u>KLEVVAATPTSLLISWDAPAVT----V<u>DLY</u>V<u>I</u>TYGETGP<u>GSGWP</u>- |
| 50 | VS<u>S</u>V<u>PT</u>KLEVVAATPTSLLISWDAPAVT----V<u>DFY</u>V<u>I</u>TYGETGG<u>VVWP</u>-- |
| 51 | VS<u>S</u>V<u>PT</u>KLEVVAATPTSLLISWDAPAVT----V<u>VLY</u>L<u>I</u>TYGETGG<u>NSPV</u>-- |
| 52 | VS<u>S</u>V<u>PT</u>KLEVVAATPTSLLISWDAPAVT----V<u>VYY</u>V<u>I</u>TYGETGG<u>NSPV</u>-- |
| 53 | VS<u>S</u>V<u>PT</u>KLEVVAATPTSLLISWDAPAVT----V<u>VLY</u>V<u>I</u>TYGETGG<u>NSPV</u>-- |
| 54 | VS<u>S</u>V<u>PT</u>KLEVVAATPTSLLISWDAPAVT----V<u>VFY</u>V<u>I</u>TYGETGG<u>NSPV</u>-- |
| 55 | VS<u>S</u>V<u>PT</u>KLEVVAATPTSLLISWDAPAVT----V<u>VFY</u>V<u>I</u>TYGETGG<u>NSPV</u>-- |
| 56 | VS<u>S</u>V<u>PT</u>KLEVVAATPTSLLISWDAPAVT----V<u>VLY</u>V<u>I</u>TYGETGG<u>NSPV</u>-- |
| 57 | VS<u>S</u>V<u>PT</u>KLEVVAATPTSLLISWDAPAVT----V<u>DFY</u>F<u>I</u>TYGETGG<u>NSPV</u>-- |
| 58 | VS<u>S</u>V<u>PT</u>KLEVVAATPTSLLISWDAPAVT----V<u>VLY</u>I<u>I</u>TYGETGGY<u>GGWP</u>- |
| 59 | VS<u>S</u>V<u>PT</u>KLEVVAATPTSLLISWDAPAVT----V<u>VFY</u>V<u>I</u>TYGETG<u>AHWPGY</u>- |
| 60 | VS<u>S</u>V<u>PT</u>KLEVVAATPTSLLISWDAPAVT---- |
| 61 | VS<u>S</u>V<u>PT</u>KLEVVAATPTSLLISWDAPAVT---- |
| 62 | VS<u>S</u>V<u>PT</u>KLEVVAATPTSLLISWDAPAVT---- |
| 63 | VS<u>S</u>V<u>PT</u>KLEVVAATPTSLLISWDAPAVT---- |
| 64 | VS<u>S</u>V<u>PT</u>KLEVVAATPTSLLISWDAPAVT---- |
| 65 | VS<u>S</u>V<u>PT</u>KLEVVAATPTSLLISWDAPAVT----V<u>VFY</u>V<u>I</u>TYGETG<u>SAWPGY</u>- |
| 66 | VS<u>S</u>V<u>PT</u>KLEVVAATPTSLLISWDAPAVT----V<u>VFY</u>V<u>I</u>TYGETGY<u>AWPGY</u>- |
| 67 | VS<u>S</u>V<u>PT</u>KLEVVAATPTSLLISWDAPAVT---- |
| 68 | VS<u>S</u>V<u>PT</u>KLEVVAATPTSLLISWDAPAVT----V<u>VLY</u>V<u>I</u>TYGETG<u>SGSWP</u>-- |
| 69 | VS<u>S</u>V<u>PT</u>KLEVVAATPTSLLISWDAPAVT---- |
| 70 | VS<u>S</u>V<u>PT</u>KLEVVAATPTSLLISWDAPAVT----V<u>VFY</u>V<u>I</u>TYGETG<u>VHWPGY</u>- |
| 71 | VS<u>S</u>V<u>PT</u>KLEVVAATPTSLLISWDAPAVT----V<u>DLY</u>L<u>I</u>TYGETGGY<u>SWP</u>-- |
| 72 | VSSVPTKLEVVAATPTSLLISWDA<u>IFWN</u>----VA<u>YYR</u>I<u>T</u>YGETGG<u>NSPV</u>-- |
| 73 | VSSVPTKLEVVAATPTSLLISWDA<u>YFWGWYYSV</u>WYYRITYGETGG<u>NSPV</u>-- |
| 74 | VSSVPTKLEVVAATPTSLLISWDA<u>SSYYGV</u>--V<u>SYYR</u>I<u>T</u>YGETGG<u>NSPV</u>-- |
| 75 | VSSVPTKLEVVAATPTSLLISWDA<u>SSYYGV</u>--V<u>EYYR</u>I<u>T</u>YGETGG<u>NSPV</u>-- |
| 76 | VSSVPTKLEVVAATPTSLLISWDA<u>SYRSHW</u>--V<u>HYYR</u>I<u>T</u>YGETGG<u>NSPV</u>-- |
| 77 | VSSVPTKLEVVAATPTSLLISWDA<u>WSAQDEYYIS</u>YYRITYGETGG<u>NSPV</u>-- |
| 78 | VSSVPTKLEVVAATPTSLLISWDA<u>ESWYWPYYV</u>SYYRITYGETGG<u>NSPV</u>-- |
| 79 | VSSVPTKLEVVAATPTSLLISWDA<u>WDWVYPYYV</u>SYYRITYGETGG<u>NSPV</u>-- |
| 80 | VSSVPTKLEVVAATPTSLLISWDA<u>SYPWWSY</u>-V<u>S</u>YYRITYGETGG<u>NSPV</u>-- |
| 81 | VSSVPTKLEVVAATPTSLLISWDA<u>FDGYWYDYV</u>SYYRITYGETGG<u>NSPV</u>-- |
| 82 | VSSVPTKLEVVAATPTSLLISWD<u>TYSYSPYNYV</u>SYYRITYGETGG<u>NSPV</u>-- |

TABLE 1-continued

| SEQ ID NO: | Amino Acid Sequence<br>10          20        BC    30 βC    40 •CD |
|---|---|
| 83 | VS<u>S</u>VP<u>TK</u>LEVVAATPTSLLISWDAPAVT----V<u>DYYL</u>ITYGETGGNSPV-- |
| 84 | VS<u>S</u>VP<u>TK</u>LEVVAATPTSLLISWDAPAVT----V<u>DLYH</u>ITYGETGGNSPV-- |
| 85 | VS<u>S</u>VP<u>TK</u>LEVVAATPTSLLISWDAPAVT----V<u>DLYH</u>ITYGETGGNSPV-- |
| 86 | VS<u>S</u>VP<u>TK</u>LEVVAATPTSLLISWDA<u>FDGYWYDYVS</u>YRITYGETGGNSPV-- |
| 87 | VS<u>S</u>VP<u>TK</u>LEVVAATPTSLLISWDA<u>FDGYWYDYVS</u>FYRITYGE<u>S</u>GGNSPV-- |
| 88 | VS<u>S</u>VP<u>TK</u>LEVVAA<u>P</u>TTLLISWDA<u>FDGYWYDYVS</u>YRITYGETGGNSPV-- |
| 89 | VS<u>S</u>VP<u>TK</u>LEVVAATPTSLLISWDA<u>FDGYWYYYVS</u>YRITYGETGGNSPV-- |
| 90 | VS<u>S</u>VP<u>TK</u>LEVVAATPTSLLISWDA<u>FDGYWYDYVS</u>YRITYGETGGNSPV-- |

| SEQ ID NO: | 30 βC    40 •CD    50 βD •DE    60    70    80 FG    90 |
|---|---|
| 91 | QEFTVPGSKSTATISGLKPGVDYTITVYA<u>VTGRGDSPASS</u>--KPISINYRT |
| 1 | QEFTVPG<u>YY</u>STATISGLKPGVDYTITVYA<u>GDLSWNFDFY</u>---SPISINYRT |
| 2 | QEFTVPG<u>YY</u>STATISGLKPGVDYTITVYA<u>GDLSWNFDFY</u>---SPISINYRT |
| 3 | QEFTVPG<u>YY</u>STATISGLKPGVDYTITVYA<u>GDLSWNFDFY</u>---SPISINYRT |
| 4 | QEFTVPG<u>YS</u>STATISGLKPGVDYTITVYA<u>IMESWYYGSY</u>---SPISINYRT |
| 5 | QEFTVPG<u>YY</u>STATISGLKPGVDYTITVYA<u>KGWYGYDY</u>-----SPISINYRT |
| 6 | QEFTVPG<u>YS</u>STATISGLKPGVDYTITVYA<u>GLYDWGYYH</u>----SPISINYRT |
| 7 | QEFTVPG<u>YY</u>STATISGLKPGVDYTITVYA<u>GSFHYPYQEY</u>---SPISINYRT |
| 8 | QEFTVPG<u>SS</u>STATISGLKPGVDYTITVYA<u>YEYYSESSS</u>----SPISINYRT |
| 9 | QEFTVPG<u>YS</u>STATISGLKPGVDYTITVYA<u>YEYYSVGYE</u>----SPISINYRT |
| 10 | QEFTVPG<u>YS</u>STATISGLKPGVDYTITVYA<u>QEYYRGTSYAP</u>--SPISINYRT |
| 11 | QEFTVPG<u>YS</u>STATISGLKPGVDYTITVYA<u>YEFYSSYG</u>-----SPISINYRT |
| 12 | QEFTVPG<u>YS</u>STATISGLKPGVDYTITVYA<u>YEFYSSYG</u>-----SPISINYRT |
| 13 | QEFTVPG<u>SS</u>STATISGLKPGVDYTITVYA<u>YEFYSSYG</u>-----SPISINYRT |
| 14 | QEFTVPG<u>YS</u>STATISGLKPGVDYTITVYA<u>GDLSFNTYYY</u>---SPISINYRT |
| 15 | QEFTVPG<u>SS</u>STATISGLKPGVDYTITVYA<u>GDLSFNTYYY</u>---SPISINYRT |
| 16 | QEFTVPG<u>YS</u>STATISGLKPGVDYTITVYA<u>GDLSFNTYYY</u>---SPISINYRT |
| 17 | QEFTVPG<u>SS</u>STATISGLKPGVDYTITVYA<u>GDIAFNWYYY</u>---SPISINYRT |
| 18 | QEFTVPG<u>SS</u>STATISGLKPGVDYTITVYA<u>GDIAFNWYYY</u>---SPISINYRT |
| 19 | QEFTVPG<u>SY</u>TATISGLKPGVDYTITVYA<u>GDIAFNWYYY</u>---SPISINYRT |
| 20 | QEFTVPG<u>SS</u>STATISGLKPGVDYTITVYA<u>GDIAFNWYYY</u>---SPISINYRT |
| 21 | QEFTVPG<u>YS</u>STATISGLKPGVDYTITVYA<u>YSYSYASMY</u>----SPISINYRT |
| 22 | QEFTVP<u>S</u>YSSTATISGLKPGVDYTITVYA<u>YSYSYASMY</u>----SPISINYRT |
| 23 | QEFTVPG<u>SS</u>STATISGLKPGVDYTITVYA<u>YSYSYASMY</u>----SPISINYRT |
| 24 | QEFTVPG<u>SS</u>STATISGLKPGVDYTITVYA<u>YGWWGSYYSFA</u>--SPISINYRT |
| 25 | QEFTVPG<u>SS</u>STATISGLKPGVDYTITVYA<u>YDDWGWT</u>------SPISINYRT |
| 26 | QEFTVPG<u>SS</u>STATISGLKPGVDYTITVYA<u>GYLWYPYGEW</u>---SPISINYRT |
| 27 | VV<u>YYI</u>ITYGETG<u>AAVWPGH</u>QEFTVPGSKSTATISGLKPGVDYTITVYA<u>VGPWDYY</u>------SPISINYRT |
| 28 | VV<u>YYH</u>ITYGETG<u>AAVWPGH</u>QEFTVPGSKSTATISGLKPGVDYTITVYA<u>QGPWVGY</u>------SPISINYRT |
| 29 | VV<u>YYH</u>ITYGETG<u>AAVWPGH</u>QEFTVPGSKSTATISGLKPGVDYTITVYA<u>QSGWYRY</u>------SPISINYRT |
| 30 | VV<u>FYV</u>ITYGETG<u>AAVWPGH</u>QEFTVPGSKSTATISGLKPGVDYTITVYA<u>QGGRWKS</u>------SPISINYRT |
| 31 | VV<u>FYV</u>ITYGETG<u>AAVWPGY</u>QEFTVPGSKSTATISGLKPGVDYTITVYA<u>QHPWMES</u>------SPISINYRT |
| 32 | QEFTVPGSKSTATISGLKPGVDYTITVYA<u>QSPFWVW</u>------SPISINYRT |
| 33 | Q<u>A</u>FTVPGSKSTATISGLKPGVDYTITVYA<u>QGQYYQY</u>------SPISINYRT |
| 34 | Q<u>A</u>FTVPGSKSTATISGLKPGVDYTITVYA<u>QGSFYSY</u>------SPISINYRT |
| 35 | Q<u>T</u>FTVPGSKSTATISGLKPGVDYTITVYA<u>QGPHMLY</u>------SPISINYRT |
| 36 | QEFTVPGSKSTATISGLKPGVDYTITVYA<u>QGPWYSY</u>------SPISINYRT |
| 37 | VV<u>YYV</u>ITYGETG<u>ASSWPGY</u>QEFTVPGSKSTATISGLKPGVDYTITVYA<u>QGPFVSY</u>------SPISINYRT |
| 38 | Q<u>A</u>FTVPGSKSTATISGLKPGVDYTITVYA<u>STVDGHS</u>------SPISINYRT |
| 39 | Q<u>AFA</u>VPGSKSTATISGLKPGVDYTITVYA<u>SSSSRISSSSS</u>--KPISINYRT |
| 40 | Q<u>AFA</u>VPGSKSTATISGLKPGVDYTITVYA<u>EHPYFSG</u>------SPISINYRT |
| 41 | Q<u>A</u>FTVPGSKSTATISGLKPGVDYTITVYA<u>YSVYGHW</u>------SPISINYRT |
| 42 | Q<u>T</u>FTVPGSKSTATISGLKPGVDYTITVYA<u>YKYPYGVYK</u>----SPISINYRT |
| 43 | Q<u>T</u>FTVPGSKSTATISGLKPGVDYTITVYA<u>YNYNDY</u>-------SPISINYRT |
| 44 | Q<u>T</u>FTVPGSKSTATISGLKPGVDYTITVYA<u>YSYYGVEG</u>-----SPISINYRT |
| 45 | Q<u>T</u>FTVPGSKSTATISGLKPGVDYTITVYA<u>YSVNPYYMSY</u>---SPISINYRT |
| 46 | Q<u>T</u>FTVPGSKSTATISGLKPGVDYTITVYA<u>VGPWDYY</u>------SPISINYRT |
| 47 | Q<u>A</u>FTVPGSKSTATISGLKPGVDYTITVYA<u>HSWDHSY</u>------SPISINYRT |
| 48 | Q<u>A</u>FTVPGSKSTATISGLKPGVDYTITVYA<u>HSFQGPY</u>------SPISINYRT |
| 49 | Q<u>A</u>FTVPGSKSTATISGLKPGVDYTITVYA<u>YSWSGVLG</u>-----SPISINYRT |
| 50 | Q<u>A</u>FTVPGSKSTATISGLKPGVDYTITVYA<u>GMVYSYPYREY</u>--SPISINYRT |
| 51 | QE<u>A</u>VPGSKSTATISGLKPGVDYTITVYA<u>YYYEAAYGSYEFYSP</u>ISINYRT |
| 52 | QEFTVPGSKSTATISGLKPGVDYTITVYA<u>YSDQVEYYEFYGSP</u>ISINYRT |
| 53 | QE<u>A</u>VPGSKSTATISGLKPGVDYTITVYA<u>YYPHSMWPYSHSS</u>PISINYRT |
| 54 | QEFTVPGSKSTATISGLKPGVDYTITVYA<u>QYGWARS</u>------SPISINYRT |

TABLE 1-continued

```
SEQ  Amino Acid Sequence
ID            10        20        30        40
NO:            •         •  BC    βC        •CD
55                          QEFTVPGSKSTATISGLKPGVDYTITVYAYAVEPYFEY----SPISINYRT
56                          QEFAVPGSKSTATISGLKPGVDYTITVYAYDLWYPYVYG---SPISINYRT
57                          QEFAVPGSKSTATISGLKPGVDYTITVYAPWNGGYID-----SPISINYRT
58                          QAFTVPGSKSTATISGLKPGVDYTITVYAHNWSGGY------SPISINYRT
59                          QKFTVPGSKSTATISGLKPGVDYTITVYAQFPWYMG------SPISINYRT
60   VVYYVITYGETGAHAWPGYQEFTVPGSKSTATISGLKPGVDYTITVYAQYPWYGG------SPISINYRT
61   VVYYYITYGETGASSWPGYQEFTVPGSKSTATISGLKPGVDYTITVYAQSGWYKY------SPISINYRT
62   VVFYLITYGETGASSWPGYQEFTVPGSKSTATISGLKPGVDYTITVYAQYPWDTG------SPISINYRT
63   VVYYYITYGETGASSWPGYQEFTVPGSKSTATISGLKPGVDYTITVYAQYGWYSG------SPISINYRT
64   VVFYVITYGETGAHAWPGYQEFTVPGSKSTATISGLKPGVDYTITVYAQYGYHQS------SPISINYRT
65                          QEFTVPGSKSTATISGLKPGVDYTITVYAQYPYYGS------SPISINYRT
66                          QEFTVPGSKSTATISGLKPGVDYTITVYAVGPYVVY------SPISINYRT
67   VVLYVITYGETGPGHSAWPQAFTVPGSKSTATISGLKPGVDYTITVYAYWDWDSHRY----SPISINYRT
68                          QAFTVPGSKSTATISGLKPGVDYTITVYAVMPWYRS------SPISINYRT
69   VVFYIITYGETGAAVWPGHQEFTVPGSKSTATISGLKPGVDYTITVYAVGPWDYY------SPISINYRT
70                          QKFTVPGSKSTATISGLKPGVDYTITVYAQFPWYMG------SPISINYRT
71                          QTFTVPGSKSTATISGLKPGVDYTITVYAYKYPYGVYK----SPISINYRT
72                          QEFTVPGYSSTATISGLKPGVDYTITVYAGDLSWNFDFY---SPISINYRT
73                          QEFTVPGYSSTATISGLKPGVDYTITVYAIMESWYYGSY---SPISINYRT
74                          QEFTVPGYSSTATISGLKPGVDYTITVYASYYYWYTSYTK--SPISINYRT
75                          QEFTVPGYSSTATISGLKPGVDYTITVYAFYYYWYSYSSSV-SPISINYRT
76                          QEFTVPSSSTATISGLKPGVDYTITVYAMDYPGMWYG----SPISINYRT
77                          QEFTVPSSSTATISGLKPGVDYTITVYAMYASYSKQYWGQGSPISINYRT
78                          QEFTVPSSSTATISGLKPGVDYTITVYAFEHHEQRYY----SPISINYRT
79                          QEFTVPSSSTATISGLKPGVDYTITVYAYSHYQMSEY----SPISINYRT
80                          QEFTVPSSSTATISGLKPGVDYTITVYAYSHYQMSEY----SPISINYRT
81                          QEFTVPSSSTATISGLKPGVDYTITVYAYSHSQQQYL----SPISINYRT
82                          QEFTVPSSSTATISGLKPGVDYTITVYAYSHYQMSEY----SPISINYRT
83                          QEFTVPGSKSTATISGLKPGVDYTITVYAFPSYVWWYNPI--SPISINYRT
84                          QEFTVPGSKSTATISGLKPGVDYTITVYAYHYWSGVYSYYP-SPISINYRT
85                          QEFTVPGSKSTATISGLKPGVDYTITVYAYYYWSGVYSYYP-SPISINYRT
86                          QVFTVPSSSTATISGLKPGVDYTITVYAYSHSQLQYL----SPISINYRT
87                          QEFTVPSSSTATISGLKPGVDYTITVYAYSHSQQQYL----SPNSINYRT
88                          QEFTVPSSSTAIISGLKPGVDYTITVYAYHHSQQQYL----SPISINYRT
89                          QEFTVPSSSTATITGLKPGVGYTITVYAYSHSQLQYL----SPISINYRT
90                          QEFTVPSSSTATITGLKPGVDYTIAVYAFSHSQLQYL----SPNSINYRT
```

Clones from Loop Library have mutations (underlined) in aa 24-29 (Double underline in WT (SEQ ID NO: 91)).

V. Examples

The following examples are given for the purpose of illustrating various embodiments and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Monobody-Mediated Enhancement of β-Galactosidase Enzyme Specificity

Current methods for engineering enzymes modify enzymes themselves and require a detailed mechanistic understanding or a high-throughput assay. The current methods of the disclosure describe a new approach where catalytic properties are modulated with binding proteins directed to an unmodified enzyme. This example uses synthetic binding proteins called monobodies. Using the example of a β-galactosidase of unknown three-dimensional structure, monobodies that restricted its substrates and selectively enhanced the production of small oligosaccharide prebiotics were identified.

Engineering enzymes with desirable catalytic properties remains a major goal of biotechnology, as enzymes are important in many industries including chemical, pharmaceutical, food, dairy and textile. Essentially all standard enzyme-engineering approaches, e.g., structure-guided design and directed evolution (See, for example, Wilks, H. M. et al. *Science* 242, 1541-1544 (1988); Chen, K. Q. & Arnold, F. H. *Biotechnology* (N Y) 9, 1073-1077 (1991); Bornscheuer, U. T. et al. *Nature* 485, 185-194 (2012); Davids, T., Schmidt, M., Bottcher, D. & Bornscheuer, U. T. *Curr Opin Chem Biol* 17, 215-220 (2013); and Goldsmith, M. & Tawfik, D. S. *Curr Opin Struct Biol* 22, 406-412 (2012)), modify the enzyme itself. The prerequisites of these approaches limit their broader application. Structure-guided design requires detailed knowledge of the three-dimensional (3D) structure and catalytic mechanism of the target enzyme, and directed evolution requires effective strategies for generating and screening numerous mutant enzymes. De novo enzyme design also requires detailed understanding of the reaction mechanism (Mak, W. S. & Siegel, J. B. *Curr Opin Struct Biol* 27, 87-94 (2014)). Industrial enzymes are often purified from their native hosts because they cannot be recombinantly produced in organisms suitable for protein engineering such as *Escherichia coli* and yeast. Their 3D structures are seldom known, and their assays are often labor intensive. These characteristics make it a formidable challenge to apply standard protein-engineering approaches to industrial enzymes, although it is often desired to modulate their properties.

This example describes a new approach to modulate catalytic properties of enzymes that are recalcitrant to traditional enzyme-engineering techniques, by using synthetic binding proteins termed monobodies (FIG. 1A). Protein design technologies are applied to the generation of synthetic binding proteins that bind to the target enzyme. Importantly, this method leaves the target enzyme itself unchanged, and it can be applied to any enzyme. Whereas different classes of binding proteins in terms of their effect and their respective utilities can be envisioned (FIG. 1B), the present study is focused on enhancing the substrate specificity, a generally challenging task in protein engineering.

This approach was tested on the modulation of substrate specificity of a β-galactosidase from *B. circulans* ATCC 31382. This enzyme catalyzes lactose hydrolysis and trans-galactosylation reactions (FIG. 1C and FIG. 1D, respectively)(Song, J. et al. *Biosci Biotechnol Biochem* 75, 1194-1197 (2011)). Because its trans-galactosylation reactions yield galacto-oligosaccharides (GOSs) that are recognized as beneficial prebiotics, it is utilized for industrial production of GOSs under the trademark of Biolacta®. However, because GOSs of any length can be the substrate of the trans-galactosylation reaction (FIG. 1D), the enzyme produces a wide range of GOSs, leading to low yields of GOSs of a specific size. Such broad substrate specificity is observed for many enzyme families that form and/or break biopolymers, including proteases, glycosidases, and lipases. Tailoring substrate specificity of these classes of enzymes is often desired but challenging.

Applicants envisioned enhancing the production of short GOSs by engineering the β-galactosidase in such a way that prevented the enzyme from using large GOS species as substrates. Cloning and functional expression of this enzyme in *E. coli* have recently been reported, and four residues that constitute the putative active-site have been identified via inactivating mutations[8]. It is a large protein, and its shortest active fragment used in this work was ~100 kDa (termed BgaD-D; see Methods)[9]. Its 3D structure or molecular details of its substrate recognition has not been elucidated. Furthermore, no high-throughput assays for profiling GOSs are available. Thus, it has been challenging to alter catalytic properties of BgaD-D using conventional approaches. In fact, none among hundreds of BgaD-D mutations constructed based on homology models exhibited the desired catalytic profile defined above (unpublished).

Applicants hypothesized that BgaD-D has subsites (−1, +1, +2, +3 and so on), each recognizing a glycosyl residue, with hydrolysis and trans-galactosylation occurring using the same catalytic site located between −1 and +1 (FIG. 1C, D). Applicants further hypothesized that blocking subsite +3 diminishes the production of tetra- and larger oligosaccharides while minimally affecting lactose hydrolysis and tri-saccharide production (FIG. 1E). Structure-guided mutagenesis directed to subsites distant from the catalytic residues has successfully altered substrate specificity of other glycosyltransferases and other enzyme types (See, for example, van der Veen, B. A. et al. *J Mol Biol* 296, 1027-1038 (2000); Chen-Goodspeed, M., Sogorb, M. A., Wu, F. & Raushel, F. M. *Biochemistry* 40, 1332-1339 (2001); and Schmitt, J., Brocca, S., Schmid, R. D. & Pleiss, *J. Protein Eng* 15, 595-601 (2002)), supporting this concept. However, it is emphasized that this method is performed without any knowledge of the presence and precise locations of such subsites in BgaD-D. These hypotheses in turn posit that binding proteins with desired specificity-enhancing characteristics should bind to the close vicinity of the catalytic center but should not inhibit lactose hydrolysis.

A series of monobodies, synthetic binding proteins based on the 10th human fibronectin type III (FN3) domain (FIG. 1A), directed to BgaD-D were generated by performing combinatorial library selection using phage- and yeast-display technologies as previously established (Koide, A., Bailey, C. W., Huang, X. & Koide, S. *J Mol Biol* 284, 1141-1151 (1998) and Koide, A., Wojcik, J., Gilbreth, R. N., Hoey, R. J. & Koide, S. *J Mol Biol* 415, 393-405 (2012)). The monobody system has generated numerous potent and specific binding proteins (Wojcik, J. et al. *Nat Struct Mol Biol* 17, 519-527 (2010)). Monobodies have strong tendency to bind to a functional site in the target protein (Gilbreth, R. N. et al. *Proc Natl Acad Sci USA* 108, 7751-7756 (2011) and Sha, F. et al. *Proc Natl Acad Sci USA* 110, 14924-14929 (2013)), and it was envisioned that its small size might be beneficial in precisely targeting a specific subsite. The monobodies from the initial, unbiased selection, represented by Mb(BgaD_L02), Mb(BgaD_S09) and Mb(BgaD_S10) bound strongly to three distinct epitopes of BgaD-D in the absence of substrates, as determined in competitive binding experiments using purified monobody samples (FIG. 2A and FIG. 3). However, none showed significant effects on BgaD-D catalytic activity (FIG. 2C and FIG. 3), suggesting that they are inert binders binding to locations distant from the active site (FIGS. 1A and 2A).

To obtain monobodies that bind to the close vicinity of the active site, second selection campaign was performed in which the three monobodies were used to mask the dominant, non-functional epitopes (FIG. 2A). This selection yielded a monobody, Mb(BgaD_L14), that bound tightly to BgaD-D ($K_D=31\pm2.3$ nM; FIG. 3B) and potently inhibited BgaD-D as assayed with o-nitro-phenyl β-D-glucopyranoside (ONPG) hydrolysis, a proxy assay for the di-saccharide hydrolysis activity (FIG. 2C). These results suggest that Mb(BgaD_L14) may bind to regions critical to catalysis, e.g. subsites −1 and/or +1 (FIG. 1C).

It was then hypothesized that desired specificity enhancers should bind to the close vicinity of the active site pocket and that their epitopes may overlap with the epitope of the inhibitory monobody, Mb(BgaD_L14). Accordingly, Applicants performed the third selection campaign, in which monobodies that are competed by Mb(BgaD_L14) but showed low inhibition of ONPG hydrolysis were recovered. A new monobody, Mb(BgaD_L19), was obtained that was competitively inhibited by Mb(BgaD_L14) but minimally affected ONPG hydrolysis (FIG. 2C). Because it bound weakly to BgaD-D ($K_D=600\pm170$ nM as assayed using yeast-surface display; FIG. 3A), the affinity of Mb(BgaD_L19) was then improved by error-prone PCR and directed evolution. A new monobody, Mb(BgaD_L23), had higher affinity ($K_D=12\pm3$ nM as assayed using yeast surface display) and maintained the desired binding profile of Mb(BgaD_L19) (FIG. 2B and FIG. 3). Both Mb(BgaD_L19) and Mb(BgaD_L23) did not compete with the three inert monobodies, as expected (FIG. 2B).

Figure 4:
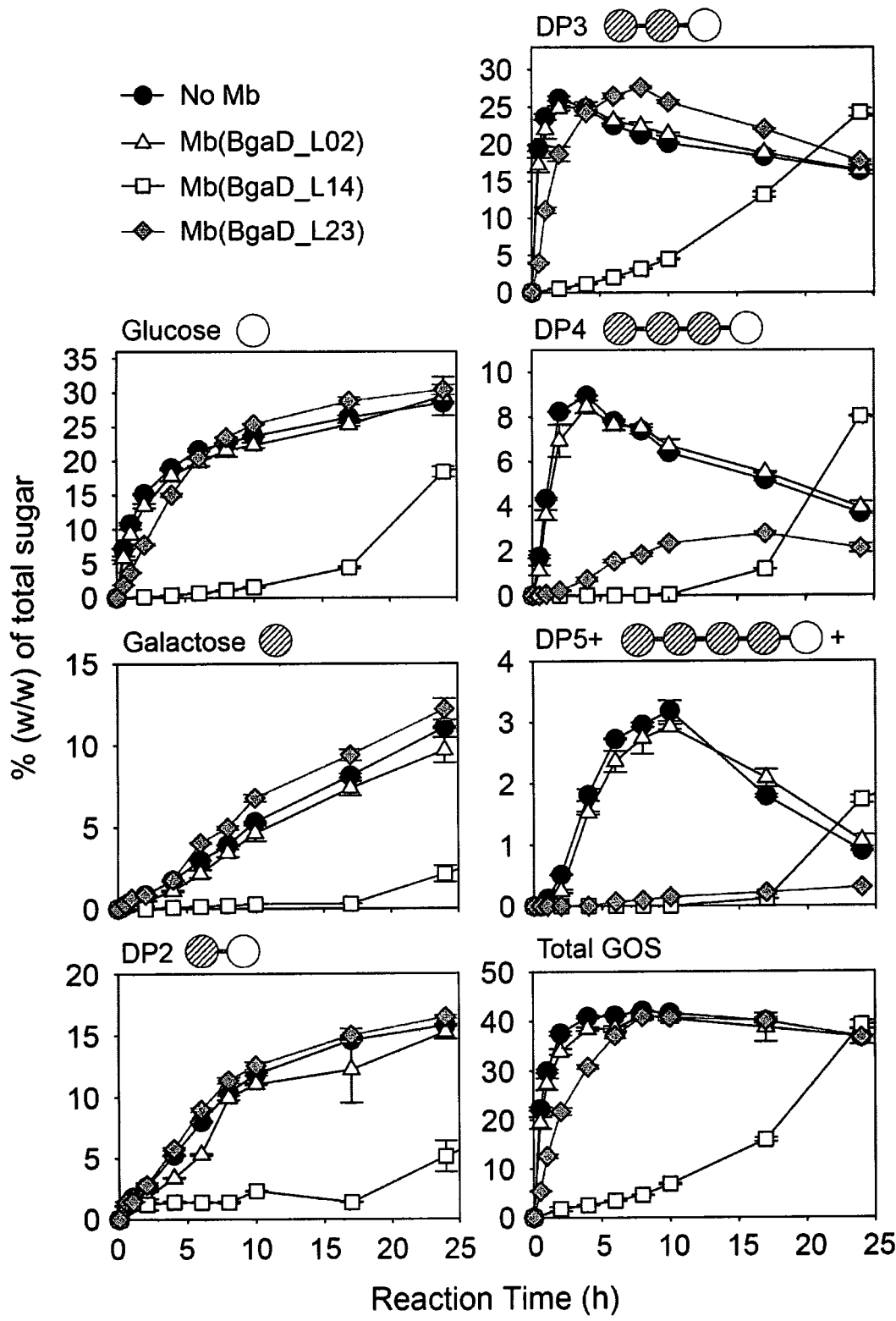
FIG. 4. Time courses of GOS production by BgaD-D in the absence or presence of monobodies. The amounts of individual sugars relative to the total sugar amount are plotted versus reaction time. The reactions started with 5% (w/v) lactose. The concentrations of monobodies used for these experiments were: 100 μM for Mb(BgaD_L02), 200 μM for Mb(BgaD_L14) and 100 μM for Mb(BgaD_L23). Data are represented as mean±s.d., n=3.
Figure 5:
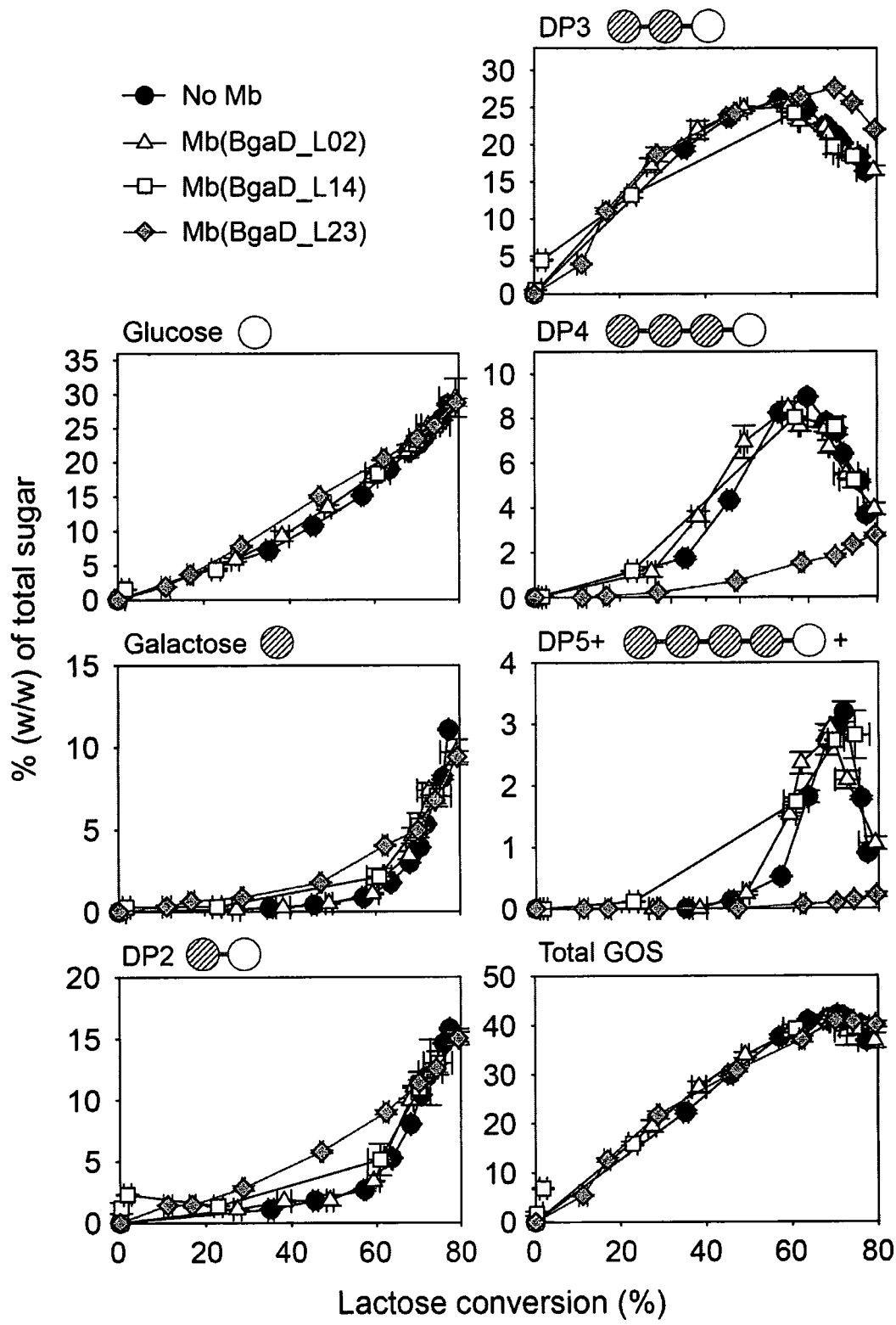
FIG. 5. GOS production by BgaD-D in the absence or presence of monobodies, with respect to the degree of lactose consumption. The amounts of individual sugars relative to the total sugar amount (weight/weight), the same data as shown in FIG. 5, are re-plotted as a function of the degree of lactose conversion, instead of reaction time. The concentrations of monobodies used for these experiments were 100 μM for Mb(BgaD_L02), 200 μM for Mb(BgaD_L14) and 100 μM for Mb(BgaD_L23). Data are represented as mean±s.d., n=3.

Next, Applicants characterized these monobodies to determine whether they alter the substrate specificity of the enzyme as was hypothesized (FIG. 1E). Their effects are shown in plots of the amount of each oligosaccharide versus reaction time and also the amount of consumed lactose, a common presentation format for comparing oligosaccharide productivity that compensates for different catalytic rates (FIG. 2D, FIG. 4, and FIG. 5). Mb(BgaD_L23) showed little effect on lactose hydrolysis and the production of mono-, di-, and tri-saccharides (FIG. 2D) By contrast, it greatly diminished the production of tetra-oligosaccharides and larger species (DP4+) (FIG. 2D). FIG. 2E compares the product profiles at the time point when the total amount of oligosaccharides reaches the maximum, a comparison that reflects the actual use of the enzyme (due to the galactosidase activity of the enzyme, longer reaction times beyond this point lead to GOS hydrolysis). Notably, the BgaD-D/Mb(BgaD_L23) complex produced the highest amount of tri-saccharide (DP3) and reduced the production of DP4 and DP5+ species by 4.5 and 30 folds, respectively, compared with BgaD-D alone and with the other monobodies (FIG. 2E). This pattern of restricted GOS production is consistent with our model (FIG. 1E). Interestingly, although Mb(BgaD_L14) potently inhibited the hydrolysis activity of BgaD-D toward lactose and similarly reduced the rates of trans-galactosylation reactions (FIG. 4), it did not affect the oligosaccharide production profile (FIG. 2D). These results are consistent with a model in which the inhibitor monobody occupies the enzyme active site (e.g. −1 and/or +1 in FIG. 1B), and only the free enzyme is catalytically active for either lactose hydrolysis or trans-galactosylation. The inert monobody, Mb(BgaD_L02) likewise showed no effects, as expected (FIG. 2D).

Mb(BgaD_L23) showed little effect on lactose hydrolysis and the production of mono-, di- and tri-saccharides (FIG. 2D). By contrast, it greatly diminished the production of tetra-oligosaccharides (DP4) and larger species (DP5+) (FIG. 2D). Notably, it enhanced tri-saccharide (DP3) production in a higher lactose conversion regime. This production pattern is consistent with Applicant's model (FIG. 1E).

Figure 6:
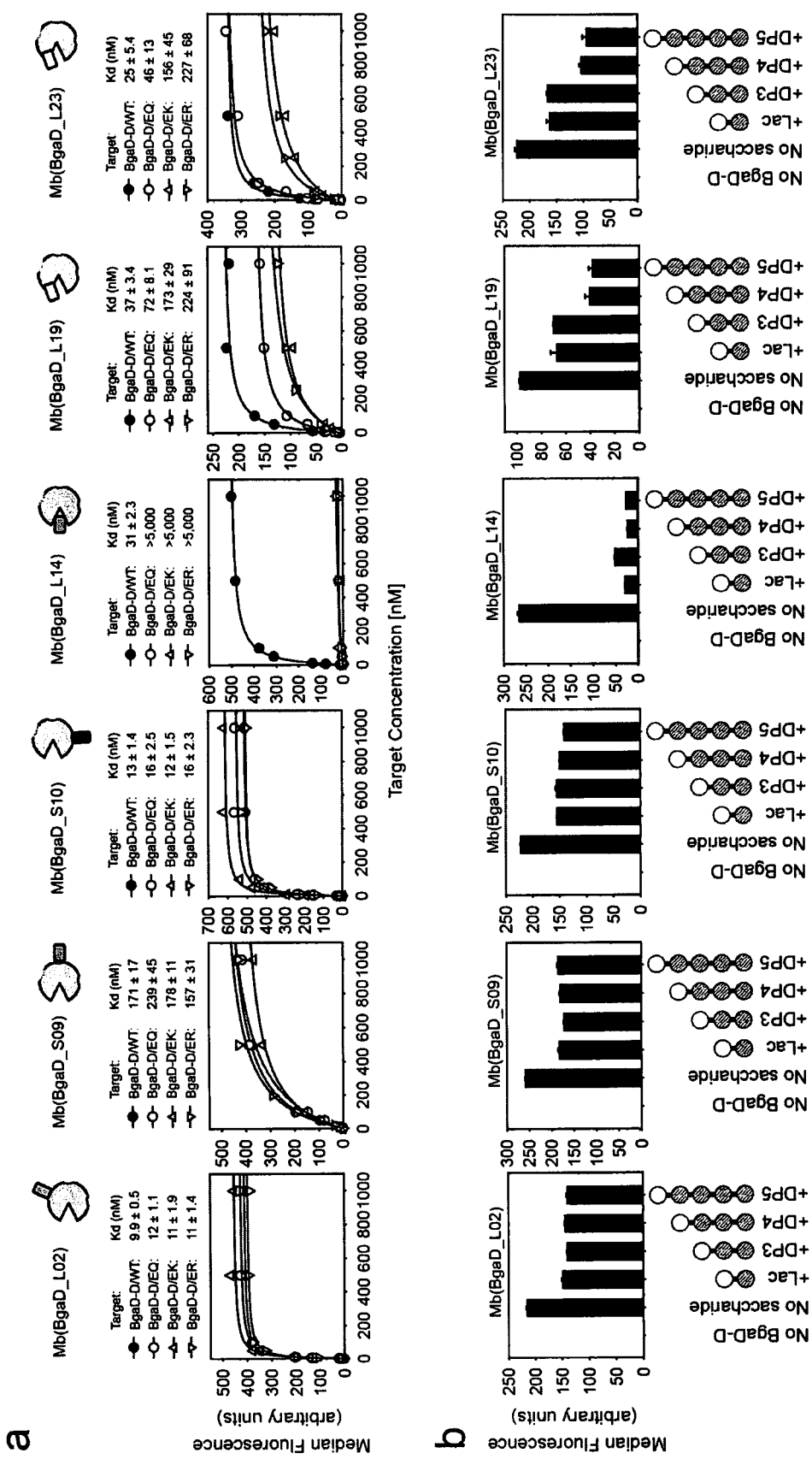
FIG. 6A-B. Effects of BgaD-D mutations and reaction products on monobody binding. (a) Binding titrations of the indicated monobodies (purified proteins) to BgaD-D and its mutants, as measured using the bead assay. The errors in the $K_D$ values are the s.d. from curve fitting. (b) Binding of the indicated monobodies (purified proteins) to BgaD-D in the presence of the indicated oligosaccharides. The concentration of BgaD-D used was 10 nM for Mb(BgaD_L02) and Mb(BgaD_S10), 30 nM for Mb(BgaD_L14) and Mb(BgaD_L23), 40 nM for Mb(BgaD_L19) or 180 nM for Mb(BgaD_S09). The oligosaccharide concentration used as a competitor was 20% (w/v). The errors shown are the s.d. from triplicate experiments. Lac, lactose.

To characterize the action mechanisms of the monobodies, effects of mutations at a putative active-site residue, E447 were tested. Mutating this residue to Gln, Arg or Lys did not affect binding of the inert monobodies, as expected (FIG. 2F and FIG. 6). By contrast, these mutations all abolished binding of Mb(BgaD_L14). The sensitivity of Mb(BgaD_L14) to the subtle perturbation by E447Q suggests that it directly binds to the active site. The specificity-enhancing monobodies, Mb(BgaD_L19) and Mb(BgaD_L23), were moderately affected by the mutations, more strongly so by E447K and E447R than E447Q (FIG. 2F and FIG. 6), suggesting that they bound to a region near E447. Together with the binding competition results (FIG. 2B), these results further support the model (FIG. 2A) that Mb(BgaD_L14) binds directly to the active site and Mb(BgaD_L19) and Mb(BgaD_L23) binds near the active site.

To clarify whether the specificity-enhancing monobodies achieve their function by limiting access of larger substrates to the enzyme, the effects of oligosaccharides on the monobody-BgaD-D interactions were then tested. The competition between the reaction products and monobodies were tested. Whereas oligosaccharides of different sizes all blocked the binding of the inhibitor monobody, Mb(BgaD_L14), the specificity-enhancing monobodies were inhibited only by longer oligosaccharides, DP4 and DP5, but not by DP3 (FIG. 2G). DP4 and DP5 are precisely the oligosaccharides whose production was reduced by the specificity-enhancing monobodies (FIG. 2D). The results strongly support the proposed mechanism of the specificity-enhancing monobodies (FIG. 1E).

Applicant's success in enhancing enzyme specificity using monobodies illustrates that synthetic binding proteins can precisely modulate enzyme properties without modifying the enzyme itself. This goal was accomplished with very limited knowledge of the structure-function relationship of the enzyme and without a high-throughput screening method. Instead, Applicants started this project with a general reaction mechanism for this class of enzymes (FIG. 1) and a back-of-envelop design for monobody action (FIG. 1E). The ability to define a desired profile for monobodies in terms of target binding was effective in identifying candidate monobodies using high-throughput techniques readily available for monobody generation and in minimizing the number of monobodies for detailed characterization, an important factor for Applicant's GOS profiling assay that takes a week to complete. Applicants successfully identified a desired specificity enhancer by performing detailed enzyme assays with only 20 monobodies. These monobodies will be powerful tools for the investigation of the substrate recognition mechanism, which will help recapitulate the specificity modifying effect of the monobody with mutations within the enzyme. Although this study is focused on modulating the substrate specificity, the other two classes of monobodies (i.e. inhibitors and inert binders; FIG. 1B) will be useful tools for different types of applications. Many enzymes recognize substrates using subsites in a manner conceptually similar to glycosyltransferases. Therefore, this strategy provides a novel and generalizable means of engineering enzymes including those inaccessible by structure-guided design or directed evolution, thereby substantially expanding enzyme-engineering technologies as well as the utility of synthetic binding proteins.

Described in the foregoing are details of the methods used in this example.

Protein Expression and Purification.

Figure 7:
FIG. 7. SDS-PAGE analysis of purified proteins used in this work. Each protein (1.5 μg) was loaded per well onto 4-20% gradient SDS-polyacrylamide gels and stained with Coomassie Brilliant Blue. The molecular weights of standard protein are also indicated.

The commercially available Biolacta® preparation (Amano Enzyme) contains four isozymes, termed BgaD-A (residues 36-1737), BgaD-B (residues 36-1422), BgaD-C (36-1249) and BgaD-D (residues 36-847), and GOSs are produced mostly by three isozymes other than BgaD-A. Applicants used the smallest isozyme, BgaD-D, for all experiments in this study. BgaD-D and its active site mutants (E447Q, E447K and E447R) were prepared as a fusion protein C-terminal to a biotin-acceptor tag (Avi-tag) and $His_6$ tag using pCold II vector (Takara). The proteins were produced as previously described, except that the protein was produced in BL21(DE3) containing the pBirAcm plasmid (Avidity) in the presence of 50 µM D-biotin for in vivo biotinylation. Monobodies were prepared as $His_{10}$-tagged proteins using the pHFT2 vector or as $His_6$-tagged and biotinylated proteins using the pHBT vector as previously described (Koide, A., Gilbreth, R. N., Esaki, K., Tereshko, V. & Koide, S. *Proc Natl Acad Sci USA* 104, 6632-6637 (2007)). All proteins were purified using Ni-Sepharose columns (GE Healthcare) and further purified with a Superdex size-exclusion column (Superdex200 for BgaD-D and Superdex75 for monobodies, GE Healthcare). Representative SDS-PAGE of purified samples is shown in Supplementary FIG. 7. For enzyme assay experiments, Applicants used BgaD-D without Avi-tag[7] and monobodies from which the affinity tag had been removed.

Phage Display and Yeast-Surface Display.

The monobody libraries used and general selection methods have been described previously (Koide, A., Wojcik, J., Gilbreth, R. N., Hoey, R. J. & Koide, S. *J Mol Biol* 415, 393-405 (2012) and Wojcik, J. et al. *Nat Struct Mol Biol* 17, 519-527 (2010)). The buffers used for binding reaction and washing were BSS (50 mM Tris-HCl, pH 7.4, containing 150 mM NaCl and 1 mg/mL bovine serum albumin) and BSST (BSS and 0.1% Tween 20), respectively, for both phage-display and yeast surface-display selection experiments. In the initial selection campaign, apo BgaD-D was used as a target and the selection was performed in an unbiased manner. The BgaD-D concentrations used for rounds 1, 2 and 3 of phage-display selection were 300 nM, 200 nM and 100 nM, respectively. Monobody-displayed phages were captured onto biotinylated target enzyme immobilized to streptavidin-coated magnetic beads (Z5481/2, Promega) and then eluted in 0.1 M Gly-HCl, pH 2.1. After gene shuffling among phage clones within each enriched population and transfer of the resulting gene pool to a yeast-surface display vector, Applicants performed library sorting using the target enzyme concentration of 100 nM, as described previously.

In the second selection campaign that intended to identify monobodies that bind to new epitopes including the active site, library sorting experiments were performed as described above except that 2 μM of Mb(BgaD_L02), 40 μM of Mb(BgaD_S09) and 3 μM of Mb(BgaD_S10) for "non functional" epitopes were added to the biotinylated target enzyme prior to mixing the target and a monobody library.

In the third campaign that aimed to enrich monobodies that bind to the vicinity of the active site, Applicants performed library sorting in an unbiased manner as described above and then the recovered population was subjected to negative selection using 2 μM of Mb(BgaD_L14) as a competitor, in which Applicants collected monobodies that are competed by Mb(BgaD_L14).

Affinity of monobodies to BgaD-D was initially determined using yeast-surface display, as described previously. Yeast cells displaying a monobody was incubated with varying concentrations of BgaD-D, washed with the buffer and stained with appropriate fluorescently labeled secondary detection reagents, prior to analysis on a flow cytometer (Guava EasyCyte 6/L, Millipore). $K_D$ values were determined from plots of the mean fluorescent intensity against BgaD-D concentration by fitting the 1:1 binding model using SigmaPlot software (Systat Software).

Affinity Maturation Using Error Prone Mutagenesis.

To generate error prone PCR library from the Mb(BgaD_L19) parent sequence, Applicants performed PCR in the presence of 0.3 mM $MnCl_2$, 7 mM $MgCl_2$, 0.2 mM each of dATP, dGTP, dCTP and dTTP, and 2.5 units of Taq DNA polymerase, and constructed the library using yeast homologous recombination, as described previously. The resultant yeast-surface display library was subjected to selections using yeast-surface display as described above.

Affinity Measurements Using Purified Proteins.

Affinity of purified monobodies were determined using a bead-based assay. Streptavidin-coated Dynabeads M280 (Invitrogen) at 20 μg/mL were incubated with an appropriate concentration of biotinylated monobody (10-30 nM) at 4° C. for 30 min with rotation, and then blocked with 10 μM D-biotin for 15 min. The monobody-immobilized beads were washed and re-suspended in BSS. 10 μL of the beads solution was then transferred to a well of a 96-well filter plate (MultiScreenHTS HV, 0.45 μm pore size, Millipore) and drained by vacuum. 20 μL of biotinylated BgaD-D or its active site mutant at various concentrations (0-5,000 nM) in BSS was added to the wells of the filter plate containing the monobody-immobilized beads and the plate was incubated at 25° C. with shaking for 20 min. The wells were drained and washed twice with BSST. After draining, 20 μL of 10 μg/mL of DyLight650-conjugated to streptavidin (Thermo) in BSS was added to each of the wells. After incubation at 4° C. with shaking for 30 min, the wells were drained and washed twice with BSST. The beads were re-suspended in 180 μL of BSS and the fluorescence emission in the far-red channel was analyzed on Guava EasyCyte 6/L. $K_D$ values were determined from plots of the median fluorescent intensity against BgaD-D concentration by fitting the 1:1 binding model using SigmaPlot software (Systat Software). $K_D$ values obtained using purified monobodies generally agreed with those determined using yeast surface display (FIGS. 3A and B), consistent with previous observations.

Competition Binding Assay.

Competition binding assay was performed using the bead-based assay with purified proteins as described above. The monobody-competition binding assay for testing the specificity of monobodies was carried out as described above except that 20 μL of an appropriate concentration of biotinylated BgaD-D pre-incubated with or without a competitor monobody added at 200 times the $K_D$ value for the monobody-BgaD-D interaction in BSS. The concentration of biotinylated BgaD-D used was 10 nM for Mb(BgaD_L02) and Mb(BgaD_S10), 30 nM for Mb(BgaD_L14) and Mb(BgaD_L23), 40 nM for Mb(BgaD_L19) or 180 nM for Mb(BgaD_S09) to account for different affinity. For the oligosaccharide-competition binding assay, the biotinylated BgaD-D was pre-incubated with or without 20% (w/v) of oligosaccharide (Lactose, DP3, DP4 or DP5) in BSS for 5 min on ice, and then 20 μL of the mixture was transferred to the wells where monobody binding took place. Experiments were performed in triplicate.

Hydrolysis Activity Assay.

Hydrolysis activity was assayed using 4 mM o-nitrophenyl β-D-glucopyranoside (ONPG) as a substrate in the assay buffer (50 mM sodium phosphate buffer, pH 7.4, containing 150 mM NaCl and 0.01% Triton X-100) at 25° C. All reagents were pre-incubated at 25° C. for 10 min, and the reaction was initiated by mixing 50 μL of substrate solution containing 8 mM ONPG and 50 μL of protein solution containing 62 nM BgaD-D and/or 10 μM monobody. After 10 min incubation at 25° C., the reactions were terminated by the addition of 250 μL of 2% (w/v) $Na_2CO_3$, and then the absorbance at 405 nm was measured using a SpectraMax 340PC plate reader (Molecular Devices). The absorbance for the assay solution containing the substrate but no proteins was subtracted as the background from the other reaction solutions to determine the catalytic activity.

Quantification of GOS Production.

The production of GOSs was measured using 5% (w/v) lactose as a substrate in the assay buffer (20 mM sodium phosphate buffer, pH 7.0, containing 150 mM NaCl) at 25° C. The reactions were initiated by mixing 125 μL of substrate solution containing 20% (w/v) lactose and 375 μL of protein solution containing 0.4 BgaD-D and/or an appropriate concentration of monobody (133-266 μM). Samples were withdrawn periodically and boiled for 10 min to terminate the reaction. The amounts of monosaccharides, disaccharides and GOSs were determined using a CK04S column (Mitsubishi Chemical) on an HPLC (LC-30AD, Shimadzu) equipped with an evaporative light scattering detector (ELSD-LTII, Shimadzu). The assay samples were eluted from the column using $H_2O$ at a flow rate of 0.4 mL/min at 80° C. For separation and determination of lactose and other disaccharides (DP2), a Asahipak NH2P-40 3E column (Shodex) was used with a gradient of $H_2O$ (solvent A) and acetonitrile (solvent B) at a flow rate of 0.3 mL/min at 30° C. Sugar concentrations were determined from peak areas. Glucose, galactose, lactose and 4'-Galactosyllactose purchased from Wako Chemicals, and tetra- and larger oligosaccharides prepared from a commercially available GOSs (Vivinal® GOS, FrieslandCampina), were used as reference compounds for producing standard curves for these assays.

The Kd and functional activity was determined for each of the Biolacta monobodies, and is shown in the table below:

| SEQ ID NO: | Clone | Kd (nM) | Function |
|---|---|---|---|
| 1 | 1Mb01: also called Mb(BgaD_L01) | 163 ± 18 | Inert |
| 2 | 1Mb02 L | | |
| 3 | 1Mb03 L | | |
| 4 | 1Mb04 L | | |
| 5 | 1Mb05 L | | |
| 6 | 1Mb06 L | | |
| 7 | 1Mb07 L | | |
| 8 | 1Mb08: Mb(BgaD_L02) | 5.7 ± 1.2 | Inert |
| 9 | 1Mb09 L | | |
| 10 | 1Mb10 L | | |
| 11 | 1Mb11 L | | |
| 12 | 1Mb12 L | | |
| 13 | 1Mb13 L | | |
| 14 | 1Mb14: Mb(BgaD_L03) | 76 ± 11 | Inert |
| 15 | 1Mb15 L | | |
| 16 | 1Mb16 L | | |
| 17 | 1Mb17 L | | |
| 18 | 1Mb18 L | | |
| 19 | 1Mb19 L | | |
| 20 | 1Mb20 L | | |
| 21 | 1Mb21 L | | |
| 22 | 1Mb22 L | | |
| 23 | 1Mb23: Mb(BgaD_L04) | 137 ± 29 | Inert |
| 24 | 1Mb24 L | | |
| 25 | 1Mb25 L | | |
| 26 | 1Mb26: Mb(BgaD_L05) | 515 ± 208 | Inert |
| 27 | 1Mb27 S | | |
| 28 | 1Mb28 S | | |
| 29 | 1Mb29 S | | |
| 30 | 1Mb30: Mb(BgaD_S06) | 24 ± 10 | Inert |
| 31 | 1Mb31 S | | |
| 32 | 1Mb32 S | | |
| 33 | 1Mb33 S | | |
| 34 | 1Mb34 S | | |
| 35 | 1Mb35 S | | |
| 36 | 1Mb36 S | | |
| 37 | 1Mb37 S | | |
| 38 | 1Mb38: Mb(BgaD_S07) | 488 ± 136 | Inert |
| 39 | 1Mb39 S | 476 ± 47 | Inert |
| 40 | 1Mb40 S | | |
| 41 | 1Mb41 S | | |
| 42 | 1Mb42 S | | |
| 43 | 1Mb43 S | | |
| 44 | 1Mb44 S | | |
| 45 | 1Mb45 S | | |
| 46 | 1Mb46 S | | |
| 47 | 1Mb47: Mb(BgaD_S08) | 214 ± 21 | Inert |
| 48 | 1Mb48 S | | |
| 49 | 1Mb49 S | | |
| 50 | 1Mb50 S | | |
| 51 | 1Mb51 S | | |
| 52 | 1Mb52: Mb(BGL_S09) | 184 ± 15 | Inert |
| 53 | 1Mb53 S | | |
| 54 | 1Mb54 S | | |
| 55 | 1Mb55 S | | |
| 56 | 1Mb56 S | | |
| 57 | 1Mb57 S | | |
| 58 | 1Mb58 S | | |
| 59 | 1Mb59 S | | |
| 60 | 1Mb60 S | | |
| 61 | 1Mb61 S | | |
| 62 | 1Mb62: Mb(BgaD_S10) | 15 ± 3.2 | Inert |
| 63 | 1Mb63 S | | |
| 64 | 1Mb64 S | | |
| 65 | 1Mb65 S | | |
| 66 | 1Mb66 S | | |
| 67 | 1Mb67: Mb(BgaD_S11) | 246 ± 18 | Inert |
| 68 | 1Mb68 L | | |
| 69 | 2Mb01: Mb(BgaD_S12) | 18 ± 1.4 | Inert |
| 70 | 2Mb02: Mb(BgaD_S13) | 50 ± 5.9 | Inert |
| 71 | 2Mb03 L | | |
| 72 | 2Mb04 L | | |
| 73 | 2Mb05 L | | Inhibitor |
| 74 | 2Mb06: Mb(BgaD_L14) | 37 ± 7.2 | Inhibitor |
| 75 | 3Mb01: Mb(BgaD_L15) | | Inert |
| 76 | 3Mb02: Mb(BgaD_L16) | | Inert |
| 77 | 3Mb03: Mb(BgaD_L17) | | Inhibitor |
| 78 | 3Mb04: Mb(BgaD_L18) | 147 ± 84 | Modifier |
| 79 | 3Mb05 | | |
| 80 | 3Mb06 | | |
| 81 | 3Mb07: Mb(BgaD_L19) | 598 ± 167 | Modifier |
| 82 | 3Mb08 L | | |
| 83 | 3Mb09: Mb(BgaD_S20) | | Inhibitor |
| 84 | 3Mb10: Mb(BgaD_S21) | | |
| 85 | 3Mb11 S | | |
| 86 | 4Mb01: Mb(BgaD_L22) | 33 ± 7.6 | Modifier |
| 87 | 4Mb02: Mb(BgaD_L23) | 12 ± 2.9 | Modifier |
| 88 | 4Mb03: Mb(BgaD_L24) | 11 ± 4.1 | Modifier |
| 89 | 4Mb04 L | | |
| 90 | 4Mb05 L | | |

Example 2: Monobody-Mediated Alteration of Lipase Substrate Specificity

The inventors have established a new strategy for altering enzyme specificity in which proxy synthetic binding proteins (termed monobodies) modulate the specificity of an otherwise unmodified enzyme. Here, the inventors tested the strategy on *Candida rugosa* lipase 1 (CRL1). The inventors successfully identified proxy monobodies that restricted the substrate specificity of CRL1 toward short-chain lipids. The successes with CRL1 here and with a β-galactosidase previously suggest broad applicability of the strategy to enzymes with distinct architectures of substrate binding sites.

Enzymes are important components in a wide range of applications in industries including food, pharmaceutical, dairy and textile, but naturally occurring enzymes often lack properties desired for the applications of interests and are needed to be engineered. However, engineering enzymes with desired catalytic properties remains a challenging task in biotechnology. Advances in techniques of DNA manipulation and molecular biology allow one to create a polypeptide with any amino acid sequence, yet one's current knowledge of enzyme's sequence-structure-function relationships is still at its early stages for de novo design and rational enzyme design, making it still a formidable challenge to design and produce an enzyme with desired functionality. Directed evolution has become a powerful tool for engineering enzymes in the absence of such knowledge and led to many successful examples. However, directed evolution experiments can be easily hampered if an efficient production system in a suitable heterologous host (e.g., *Escherichia coli*) and a high-throughput enzyme assay are unavailable. Thus, there remain many challenges in enzyme engineering for which conventional approaches are ineffective or impractical.

Described in Example 1 is a new strategy for altering enzyme specificity with proxy binding proteins directed to the precise potion within the enzyme substrate-binding site. Using the example of a β-galactosidase, BgaD-D, from *Bacillus circulans* and monobodies, synthetic binding proteins based on the 10th human fibronectin type III (FN3) domain, the inventors successfully altered the enzyme's substrate specificity for its trans-galactosylation reaction and selectively enhanced the production of short oligosaccharide. The strategy was designed based on a general mechanism of substrate recognition by β-galactosidases in which discrete sub-sites recognize different sugar moieties within a substrate. By generating a monobody that binds an appropriate sub-site and thereby blocking the binding of substrates that requires the blocked sub-site, the inventors can restrict the range of substrates that an enzyme acts on. Because this strategy does not modify the target enzyme itself, it can be applied to an enzyme system that does not require either heterologous expression systems or detailed knowledge of structure information of the enzyme. Furthermore, monobodies with desired target-binding profiles can be readily identified through a high-throughput protein design platform, eliminating the need for a high-throughput enzyme assay. Therefore, this strategy should be an attractive alternative to conventional methods for engineering substrate specificity, particularly for restricting substrates to the smaller shorter species among natural substrates of an enzyme.

In this example, the inventors tested the strategy on restricting the substrate specificity of a lipase, lipase 1 from *Candida rugosa* (CRL1), an enzyme distinctly different from β-galactosidase used in Example 1. The crystal structures of CRL1 as well as other iso-forms have been determined. Lipases (triacylglycerol lipase EC 3.1.1.3) catalyze both hydrolysis and synthesis of triacylglycerides and several other esters. They have broad specificity in terms of substrate size (short to long fatty acids) and in terms of substrate shape and chemistry (saturated and poly-unsaturated fatty acids). Their broad specificity is useful in certain applications such as food processing, pharmaceutical synthesis, oil refining, flavor development, or oil wastewater treatment, but it is not necessarily desirable for manufacturing of a defined product. For example, in ripening and enhancing cheese flavor, lipases ideally should hydrolyze only short chain fatty acids to produce cheese flavor. In reality, however, lipases also hydrolyze long-chain fatty acids that contribute to an undesired soapy flavor. Therefore, tailoring the substrate specificity of lipases toward a specific fatty-acid chain length is often desired.

Although lipases catalyze hydrolysis and synthesis reactions toward their substrates similar to the β-galactosidase, BgaD-D, used in Example 1, these two types of enzymes differ substantially in terms of the architecture of substrate binding site. The substrate-binding site of BgaD-D consists of shallow, surface-exposed pockets readily accessible by proxy monobodies, whereas that of CRL1 is a deeply buried tunnel whose inner surface is unlikely to be directly accessibly by monobodies. Furthermore, the level of discrimination needed for CRL1 (one or two hydrocarbon units) is much finer than that for BgaD-D (a sugar unit), and the lipase substrate-binding site does not have discrete sub-sites for discriminating hydrocarbon chains of different lengths. Taken together, although chain length specificity of CRL1 and its homologs has been altered by structure-guided mutations of residues lining the substrate-binding tunnel, it is unclear whether a proxy monobody can achieve a similar effect. Thus, the inventors considered alteration of CRL1 substrate specificity an interesting and informative challenge for their enzyme engineering strategy.

The inventors generated a series of monobodies directed to CRL1 by performing combinatorial library selection using phage- and yeast-display technologies by following previously established procedures. In most lipases, a mobile segment named lid covers the active site and keeps the enzymes in the closed and inactive form. In the presence of a hydrophobic solute such as a detergent, the lid opens, making the lipase active site accessible to the substrate and thus the lipase is active. To generate monobodies to the catalytically active state of CRL1, the inventors included Triton X-100 to all buffers used during monobody generation. The inventors reasoned that this way the inventors would enrich monobodies that bound in or near the substrate-binding site.

Figure 8:
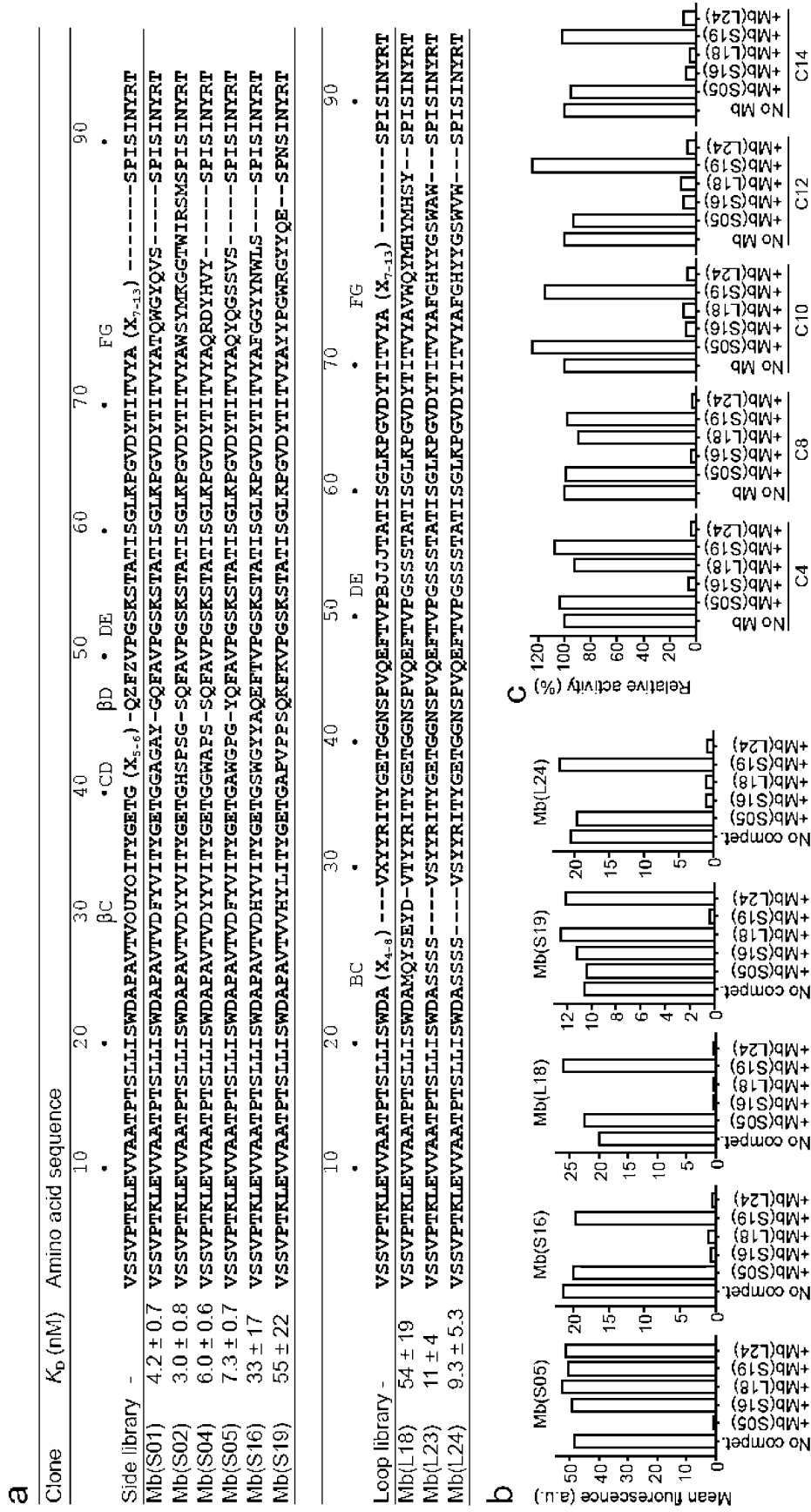
FIG. 8A-C. Monobodies binding to CRL1. (a) Amino acid sequences of monobodies generated from the side (upper) and loop (lower) libraries. "X" denotes a mixture of 30% Tyr, 15% Ser, 10% Gly, 5% Phe, 5% Trp and 2.5% each of all the other amino acids except for Cys; "B", a mixture of Gly, Ser and Tyr; "J", a mixture of Ser and Tyr; "0", a mixture of Asn, Asp, His, Ile, Leu, Phe, Tyr and Val; "U", a mixture of His, Leu, Phe and Tyr; "Z", a mixture of Ala, Glu, Lys and Thr. The sequences shown correspond to SEQ ID NOS: 92, 93, 94, 96, 97, 107, 109, 113, 115, 116, and 117, respectively. (b) Competition binding experiments using yeast-surface display. Binding of monobodies indicated above each panel to CRL1 in the presence and absence of competitor monobodies is shown. The CRL1 concentrations used were 10 nM for Mb(S01), Mb(S02), Mb(S03) and Mb(S05), 20 nM for Mb(L23) and Mb(L24), and 100 nM for Mb(S16), Mb(L18) and Mb(S19). The monobody concentrations used as a competitor was 100-200 fold greater than the $K_D$ value for the interaction of each competitor monobody with CRL1. (c) pNP-ester hydrolysis activity of CRL1 in the absence or presence of monobodies. The protein concentrations used for this assay were 10 nM and 1 μM for CRL1 and monobodies, respectively. The activities for each chain length of pNP-esters were separately normalized against those of CRL1 in the absence of a monobody.

The initial unbiased selection yielded a total of 11 unique monobodies. Based on phylogenetic analysis of these monobodies, the inventors produced 4 clones as purified proteins, Mb(CRL_S01), Mb(CRL_S02), Mb(CRL_S04) and Mb(CRL_S05) (FIG. 8A), representing each "family" of these monobodies. Despite the sequence diversity in these monobodies, all of them bound to an overlapping surface ("epitope") of CRL1, as determined in competitive binding experiments using purified monobody samples (data not shown). For brevity, hereafter in the text abbreviated names for monobodies is used where "CRL_" is omitted. None of them from the initial pool of monobodies showed significant effects on CRL1 catalytic activity (data for only Mb(S05) is shown in FIG. 8C), suggesting that they are inert binders binding to a location distant from the active site.

To obtain monobodies that bind to the close vicinity of the active site, the inventors performed the second selection campaign in which the inventors used one of the inert binders, Mb(S05), to mask the dominant, non-functional epitope. This selection yielded 11 different monobodies, and of them the inventors identified three different types of monobodies with similar $K_D$ values of approximately 50 nM (FIG. 8A). Mb(S16) potently inhibited CRL1 activity toward all chain lengths tested of synthetic p-nitrophenyl (pNP)-esters with a single aliphatic chain. The inventors used these pNP esters as proxy substrates for characterizing the chain-length specificity at the scissile fatty acid binding site (FIG. 8C). This result suggests that Mb(S16) may bind to a region critical for catalysis such as the active site. Mb(L18) showed a desired profile as a specificity modifier in which the monobody significantly reduced the activity of CRL1 toward the chain lengths longer than C8 but showed little effect on the activity toward C4 and C8 (FIG. 8C). The binding of Mb(L18) was competed by Mb(S16), suggesting that Mb(L18) may bind to a position close vicinity to the active site (FIG. 8B). Mb(S19) did not show any significant effect on CRL1 catalytic activity and the binding was not competed with either Mb(S16) or Mb(L18) (FIGS. 8B and 8C). Further selection campaign to obtain monobodies that are competed by Mb(L18) but have different profiles produced two additional inhibitory monobodies, Mb(L23) and Mb(L24) with a single amino acid difference (FIG. 8A-C).

The sequence of the CRL monobodies is provided in the table below:

Amino acid sequences of CRL1-binding monobodies

| SEQ ID NO | Clone | $K_D$ (nM) | Amino acid sequence |
|---|---|---|---|
| 92 | Side library | — | VSSVPTKLEVVAATPTSLLISWDAPAVTVTVYA(X$_{5-6}$)-QZFZVPGSKSTATISGLKPGVDYTITVYA(X$_{7-13}$)------SPISINYRT |
| 93 | Mb(S01) | 4.2 ± 0.7 | VSSVPTKLEVVAATPTSLLISWDAPAVTVDFYVITYGETGTGGAGAYGQ-FAVPGSKSTATISGLKPGVDYTITVYATQWGYQVS-----SPISINYRT |
| 94 | Mb(S02) | 3.0 ± 0.8 | VSSVPTKLEVVAATPTSLLISWDAPAVTVDYYVITYGETGTGSHSPSGSQ-FAVPGSKSTATISGLKPGVDYTITVYAWSYMKGGTWIRSMSPISINYRT |
| 95 | Mb(S03) | — | VSSVPTKLEVVAATPTSLLISWDAPAVTVHYFITYGETGSAVPPSQKPKVPGSKSTATISGLKPGVDYTITVYAKYDYWGYMGYY-SPISINYRT |
| 96 | Mb(S04) | 6.0 ± 0.6 | VSSVPTKLEVVAATPTSLLISWDAPAVTVDYYVITYGETGGWAPSSQ-FAVPGSKSTATISGLKPGVDYTITVYAQRDYHVY-----SPISINYRT |
| 97 | Mb(S05) | 7.3 ± 0.7 | VSSVPTKLEVVAATPTSLLISWDAPAVTVDFYVITYGETGAWGPGYQ-FAVPGSKSTATISGLKPGVDYTITVYAQYQGSSVS-----SPISINYRT |
| 98 | Mb(S06) | — | VSSVPTKLEVVAATPTSLLISWDAPAVTVDYYVITYGETGGSHGGGQ-FAVPGSKSTATISGLKPGVDYTITVYAQHGYAVY-----SPISINYRT |
| 99 | Mb(S07) | — | VSSVPTKLEVVAATPTSLLISWDAPAVTVDYYVITYGETGSSGPSSQ-FAVPGSKSTATISGLKPGVDYTITVYAQGYHQGYWVS---SPISINYRT |
| 100 | Mb(S08) | — | VSSVPTKLEVVAATPTSLLISWDAPAVTVDYYVITYGETGSHSPSGSQ-FAVPGSKSTATISGLKPGVDYTITVYATQWGYQVS-----SPISINYRT |
| 101 | Mb(S09) | — | VSSVPTKLEVVAATPTSLLISWDAPAVTVDYYVITYGETGGSHGGGQ-FAVPGSKSTATISGLKPGVDYTITVYATQWGYQVS-----SPISINYRT |
| 102 | Mb(S10) | — | VSSVPTKLEVVAATPTSLLISWDAPAVTVDYYVITYGETGWSHGSSQ-FAVPGSKSTATISGLKPGVDYTITVYAQGYHQGYWVS---SPISINYRT |
| 103 | Mb(S11) | — | VSSVPTKLEVVAATPTSLLISWDAPAVTVLHYLITYGETGGVPPSQKPKVPGSKSTATISGLKPGVDYTITVYAKSYSMWY-----SPISINYRT |
| 104 | Mb(S12) | — | VSSVPTKLEVVAATPTSLLISWDAPAVTVVHYFITYGETGGPSSPSQKPKVPGSKSTATISGLKPGVDYTITVYAYYWRGYS-----NPISINYRT |
| 105 | Mb(S13) | — | VSSVPTKLEVVAATPTSLLISWDAPAVTVVHYFITYGETGSAVPPSQKPKVPGSKSTATISGLKPGVDYTITVYAYFGSYDWVQ---SPISINYRT |
| 106 | Mb(S14) | — | VSSVPTKLEVVAATPTSLLISWDAPAVTVHHYFITYGETGSYSPSPSQKFAVPGSKSTATISGLKPGVDYTITVYAYYPGWRGYYQE-SPISINYRT |
| 107 | Mb(S16) | 33 ± 17 | VSSVPTKLEVVAATPTSLLISWDAPAVTVDHYVITYGETGSWGYYAQEFTVPGSKSTATISGLKPGVDYTITVYAFGGYYNWLS----SPISINYRT |
| 108 | Mb(S17) | — | VSSVPTKLEVVAATPTSLLISWDAPAVTVDHYVITYGETGSHVPSVSQKFAVPGSKSTATISGLKPGVDYTITVYAFGQYYEWIY---SPISINYRT |
| 109 | Mb(S19) | 55 ± 22 | VSSVPTKLEVVAATPTSLLISWDAPAVTVHYLITYGETGAPVPPSQKFAVPGSKSTATISGLKPGVDYTITVYAYYPGWRGYYQE-SPNSINYRT |
| 110 | Mb(S20) | — | VSSVPTKLEVVAATPTSLLISWDAPAVTVHHYFITYGETGYVPSPSVPSQKFAVPGSKSTATISGLKPGVDYTITVYAFGGYYNWLS---SPISINYRT |
| 111 | Mb(S21) | — | VSSVPTKLEVVAATPTSLLISWDAPAVTVVHHYFITYGETGFHVPPSQKFAVPGSKSTATISGLKPGVDYTITVYAFGGYYNWLS---SPISINYRT |
| 112 | Mb(S22) | — | VSSVPTKLEVVAATPTSLLISWDAPAVTVHHYLITYGETGGSVPVSQKFAVPGSKSTATISGLKPGVDYTITVYAFGGYYNWLS---SPINSINYRT |

-continued

Amino acid sequences of CRL1-binding monobodies

| SEQ ID NO | Clone | K_D (nM) | Amino acid sequence |
|---|---|---|---|
| | | | 10          20          30       40       50       60       70       90 |
| | | | ·           ·           βC       ·CD      βD ·DE    ·        ·  FG     · |
| 113 | Loop library | — | VSSVPTKLEVVAATPTSLLISWDA(X_{4-8})---VXYRITYGETGGNSPVQEFTVPBJJTATISGLKPGVDYTITVYA(X_{7-13})------SPISINYRT |
| 114 | Mb(L15) | — | VSSVPTKLEVVAATPTSLLISWDDAPYNYGYWNYRITYGETGNSPVQEFTVPGYSSTATISGLKPGVDYTITVYAYYEESEYSDG--SPISINYRT |
| 115 | Mb(L18) | 54 ± 19 | VSSVPTKLEVVAATPTSLLISWDAMQYSEYD-VTYYRITYGETGNSPVQEFTVPGSSTATISGLKPGVDYTITVYAVWQYMHYMHSY--SPISINYRT |
| 116 | Mb(L23) | 11 ± 4 | VSSVPTKLEVVAATPTSLLISWDASSSS    VSYYRITYGETGNSPVQEFTVPGSSTATISGLKPGVDYTITVYAFGHYYGSWAW-- SPISINYRT |
| 117 | Mb(L24) | 9.3 ± 5.3 | VSSVPTKLEVVAATPTSLLISWDASSSS----VSYYRITYGETGNSPVQEFTVPGSSTATISGLKPGVDYTITVYAFGHYYGSWVW---SPISINYRT |

Figure 9:
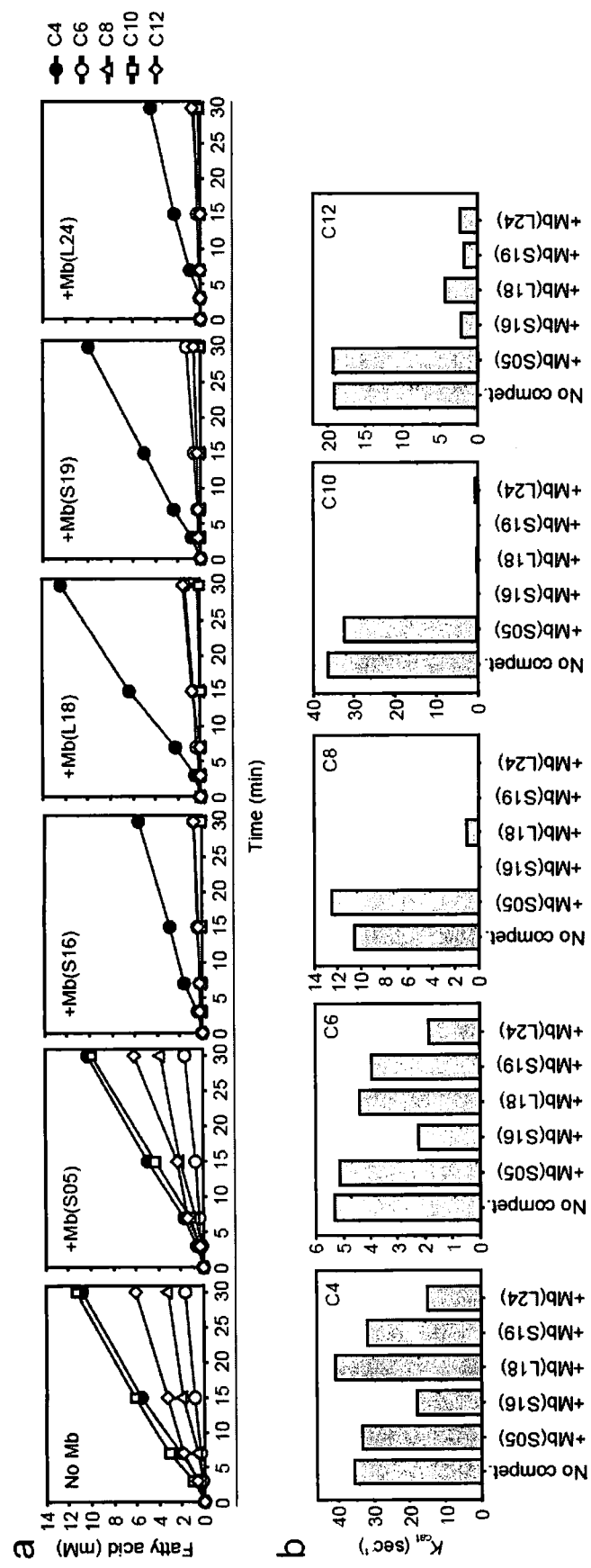
FIG. 9A-B. Monobodies modulate chain length specificity of CRL1. (a) Time courses of triacylglyceride hydrolysis catalyzed by CRL1 (175 nM) in the absence or presence of monobodies (50 μM). The concentrations of indicated fatty acids (mM) are plotted as a function of reaction time. (b) $K_{cat}$ values for each chain length of triacylglycerides. The $K_{cat}$ values were calculated by fitting the data (upper panel) to a linear function. Note that the the vertical scales are different for each panel to better illustrate the effects of monobodies.

Next, the inventors characterized these monobodies to determine whether they alter the chain length specificity of CRL1 on triacylglycerides. The effects of monobodies are shown in plots of the amount of each fatty acid produced versus reaction time (FIG. 9A) and in comparisons of the $K_{cat}$ values ($sec^{-1}$) for each length of triacylglyceride substrate (FIG. 9B). Mb(L18), the specificity modifier as tested with the pNP substrate, showed little effect on the activity toward C4 and C6 but potently inhibited the activity toward C8, C10 and C12 as these activities were reduced by 11-, 102- and 4.5-fold relative to CRL1 alone, respectively (FIG. 9B). Mb(S16) and Mb(L24) both inhibited the activity of CRL1 toward all chain lengths tested (FIG. 9). Of them, Mb(L24) showed more potent inhibition, probably because the monobody had higher affinity to CRL1 (FIG. 8B) and consequently the binding with CRL1 was more complete than Mb(S16) at the same monobody and enzyme concentrations. The inert monobody, Mb(S05), showed no effects, as expected (FIG. 9). Thus, their profiles observed for triacylglycerides were generally similar to those observed for pNP-esters, with a few exceptions. Mb(L18) did not inhibit the CRL1 activity on the C8 pNP ester (FIG. 8C) but it was a potent inhibitor of the activity on the C8 triacylglyceride (FIG. 9). Similarly, despite the inert profile of Mb(S19) against pNP-esters (FIG. 8C), this monobody significantly reduced CRL1 activity on triacylglycerides with chain lengths longer than C6 (FIG. 9). These results indicate that effects of monobodies on CRL1 activity on pNP-esters and on triacylglycerides can be different, and these differences are likely due to the different numbers of aliphatic chains in these substrates and how they are recognized by CRL1, as discussed below.

Figure 10:
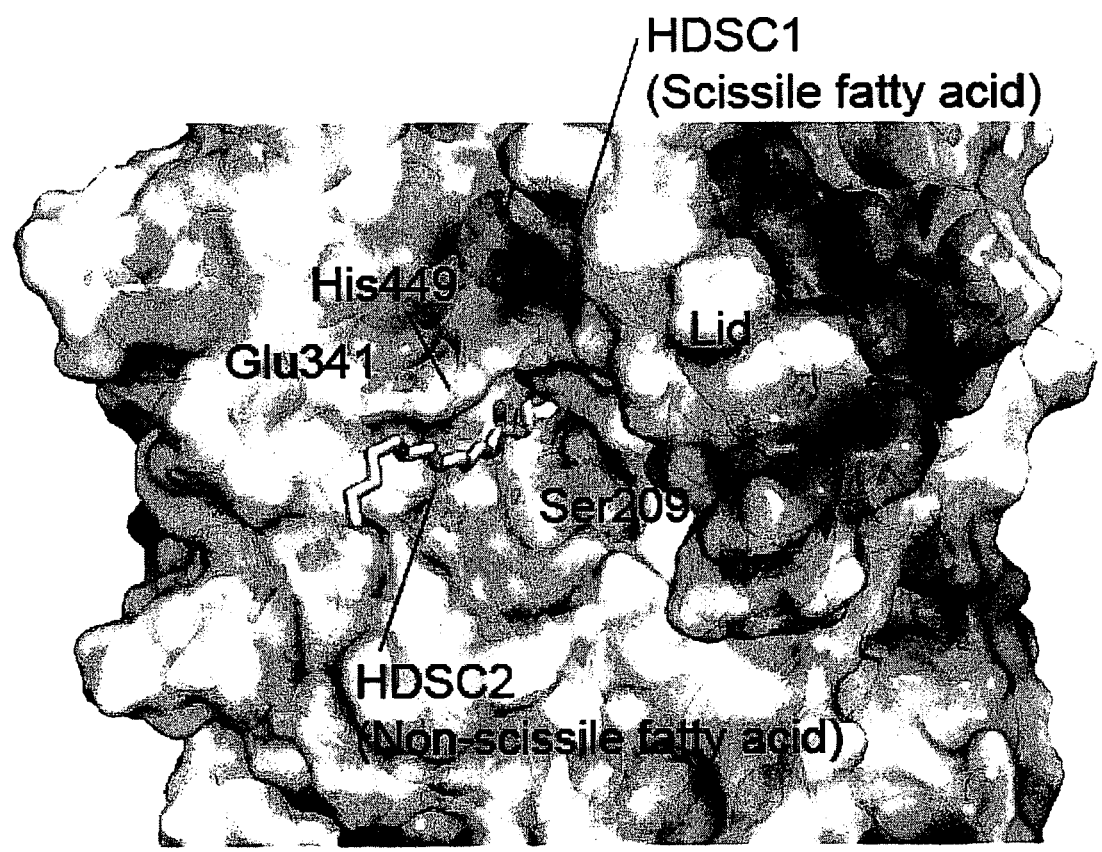
FIG. 10. Structure of CRL1 in complex with a substrate analogue showing scissile and non-scissile fatty acid binding sites. The electrostatic potentials were calculated and mapped on the surface model of the CRL1 structure (PD-BID: 1LPP) using PyMOL (found on the world wide web at pymol.org). The active-site residues are indicated as yellow stick models in which the oxygen and nitrogen atoms are colored red and blue, respectively, and labeled. The two molecules of a substrate analogue, HDS (1-hexadecano-sulfonic acid), respectively binding to the scissile and non-scissile fatty acid binding sites are shown as stick model whose carbon atoms are colored green and labeled. A hydrophobic patch proposed as a non-scissile fatty acid-binding site is located behind the label "Ser209". The helical segment "Lid" that covers the scissile substrate-binding site is also indicated.

The available crystal structures of CRL1 in complex with a substrate analogue (FIG. 10) give a hint of the action mechanisms of two modifiers, Mb(L18) and Mb(S19). The crystal structures reveal three hydrophobic sites that accommodate the sn-1, sn-2, and sn-3 fatty acids of triacylglyceride. The scissile fatty acid (sn-1 or sn-3) binding site has a deep tunnel-like architecture and the other fatty acid binding sites are hydrophobic patches exposed to the solvent (FIG. 10). pNP-ester substrates must bind to the tunnel-like binding site to be cleaved, and therefore these substrates do not report changes in the non-scissile site. According to the results that Mb(L18) altered chain length specificity of CRL1 toward pNP-esters and was competed by the inhibitor, Mb(L18) may bind to a position close vicinity to the active site and affect binding of scissile fatty acid to the tunnel-like binding site. It has been reported for CRL1 and other iso-forms that mutations of residues not only inside the tunnel but also at the entrance of the tunnel alter the chain length specificity. Because monobodies are not small enough to directly access a space inside the tunnel without grossly disrupting the tunnel, Mb(L18) may bind to a certain position around the entrance of the tunnel and interfere with entering of longer chain substrates into the tunnel. However, binding to other regions indirectly affecting the size or shape of the tunnel cannot be excluded. Mb(S19) was not competed by Mb(S16) and was inert against pNP-esters, but it altered the chain length specificity of CRL1 toward triacylglycerides. These results suggest that Mb(S19) may not affect binding of scissile fatty acid but rather affect binding of another position of fatty acid in triacylglyceride to the binding site. Binding sites of non-scissile fatty acids are relatively large and exposed to the solvent, and each binding site is cleanly separated from scissile fatty acid binding site (FIG. 10). Thus, precisely pointing and blocking of a certain position within the non-scissile fatty acid binding site(s) by monobodies without interfering binding of scissile fatty acid may be possible. Altering chain length specificity against triacylglycerides with retaining specificity for pNP-esters by mutations at the non-scissile fatty acid binding sites have been reported for other iso-forms.

In this Example, experimental evidence that the substrate specificity of CRL1 can be altered by monobodies is provided. Despite the difficulty of directly binding to the scissile substrate binding site of CRL1 and the relatively large size of the monobody with respect to the small differences among the lipase substrates, the inventors successfully identified a modifier that altered the substrate specificity by screening only a total of 24 monobodies. Tunnel-like substrate binding site is now recognized as a ubiquitous architecture and spans across all six major classes of enzymes. Therefore, it is anticipated that this strategy would be useful for engineering catalytic properties of a wide range of enzymes.

The following materials and methods were used in this example and are applicable to the methods described herein.

Preparation of Biotinylated CRL1:

Purified CRL1 was obtained from c-LEcta (Germany). The protein was biotinylated using the EZ-Link Sulfo-NHS-LC-Biotinylation Kit (ThermoScientific). Briefly, CRL1 was dissolved in and further dialyzed against PBS (50 mM sodium phosphate buffer, pH 7.4, containing 150 mM NaCl), and incubated with a 5-fold molar excess of NHS-LC-biotin at 4° C. for 16 hrs. Non-reacted biotin was removed using a desalting column, and the resultant protein sample was purified with a Superdex size-exclusion column (Superdex200, GE Healthcare). Biotin incorporation into CRL1 was estimated to be about 2 per CRL1 molecule by a colorimetric HABA dye assay.

Expression and Purification of Monobodies:

Monobodies were prepared as $His_{10}$-tagged proteins using the pHFT2 vector as previously described. All proteins were purified using Ni-Sepharose columns (GE Healthcare) and further purified with a Superdex size-exclusion column (Superdex75, GE Healthcare). For enzyme assay experiments, we used monobodies from which the affinity tag had been removed by TEV protease cleavage.

Phage Display and Yeast-Surface Display:

The monobody libraries used and general selection methods have been described previously. The buffer used for binding reaction and washing was BSST (50 mM Tris-HCl, pH 7.4, containing 150 mM NaCl, 1 mg/mL bovine serum albumin and 0.5% (v/v) Triton X-100) for both phage-display and yeast surface-display experiments. In the initial selection campaign, the selection was performed in an unbiased manner. The biotinylated target enzyme concentration used for rounds 1, 2 and 3 of phage-display selection was 100 nM. Monobody-displayed phages were captured onto biotinylated target enzyme immobilized to streptavidin-coated magnetic beads (Z5481/2, Promega) and then eluted in 0.1 M Gly-HCl, pH 2.1.

After gene shuffling among phage clones within each enriched population and transfer of the resulting gene pool to a yeast-surface display vector, we performed library sorting using the target enzyme concentrations of 100 nM and 20 nM for the first and second round sorting, respectively, as described previously. The amino acid sequences of the identified monobodies were deduced by DNA sequencing of the yeast display vectors. Phylogenetic tree analysis was performed using the program Phylogeny (EMBL-EBI).

In the second selection campaign, library sorting experiments were performed as described above except that 2 µM of Mb(S05) was added to the biotinylated target enzyme prior to mixing the target and a monobody library. We alternated library sorting with the enzyme-monobody complex and sorting with the enzyme only to ensure that selected monobodies bound to the enzyme, not to the competitor monobodies. In the third campaign, we performed library sorting in an unbiased manner as described above and then the recovered population was subjected to negative selection using 4 µM of Mb(L18) as a competitor.

Affinity of monobodies to CRL1 was determined using yeast-surface display, as described previously. Yeast cells displaying a monobody were incubated with varying concentrations of CRL1, washed with the buffer and stained with appropriate fluorescently labeled secondary detection reagents, prior to analysis on a flow cytometer (Guava EasyCyte 6/L, Millipore). $K_D$ values were determined from plots of the mean fluorescent intensity against CRL1 concentration by fitting the 1:1 binding model using SigmaPlot software (Systat Software).

Competition Binding Assay:

Competition binding assay was performed using yeast-surface display as described above. The monobody-competition binding assay for testing the specificity of monobodies was carried out as described above except that 20 µL of an appropriate concentration of biotinylated CRL1 pre-incubated with or without a competitor monobody added at 100-200 times the $K_D$ value for the monobody-CRL1 interaction in BSST. The concentration of biotinylated CRL1 used was 10 nM for Mb(S01), Mb(S02), Mb(S03) and Mb(S05), 20 nM for Mb(L23) and Mb(L24), or 100 nM for Mb(S16), Mb(L18) and Mb(S19) to account for different affinity.

Hydrolysis Activity Assay with pNP-Esters:

Fatty chain length profiles were determined using 1 mM p-nitrophenyl (pNP)-esters of acetate (C2), butyrate (C4), caprylate (C8), caprate (C10), laurate (C12) and myristate (C14) (all from Sigma-Aldrich) as substrates in the assay buffer (50 mM HEPES-NaOH, pH 6.8, containing 0.5% Triton X-100) at 25° C. All reagents were pre-incubated at 25° C. for 10 min, and the reaction was initiated by mixing 225 µL of substrate solution containing 1.12 mM pNP ester and 25 µL of protein solution containing 100 nM CRL1 and/or 10 µM monobody. Enzyme activity was determined from the initial hydrolysis rate of pNP-esters using a SpectraMax 340PC plate reader (Molecular Devices) following the absorbance at 405 nm. The absorbance for the assay solution containing the substrate but no proteins was subtracted as the background from the other reaction solutions to determine the catalytic activity.

Hydrolysis Activity Assay with Triacylglycerides:

Hydrolysis activity against triacylglycerides was measured using tributyrin (C4; Sigma-Aldrich), tricaproin (C6; Tokyo Kasei), tricaprylin (C8; Wako Pure Chemicals), tricaprin (C10; Tokyo Kasei) and trilaurin (C12; Tokyo Kasei) as substrates. The substrate solution consisted of 0.5% (w/v) polyvinyl alcohol and 80 mM of tributyrin or 40 mM of one of the other triacylglycerides, and was emulsified by ultrasonication. Immediately after emulsification, 0.3 mL of the emulsified substrate solution was mixed with 0.6 mL of a buffer solution (0.1 M sodium phosphate buffer, pH 7.0) and the resultant solution was incubated at 25° C. for 10 min. The assay was initiated by mixing the substrate solution (0.9 mL) and 0.3 mL of protein solution containing 0.7 µM CRL1 and/or 200 µM monobody, and incubated at 25° C. with constant shaking. Samples were withdrawn periodically and 150 µL of the samples were mixed with 50 µL of 0.5 M HCL and 25 mM nonanoic acid (C9 used as an internal standard; Wako Pure Chemicals) to terminate the reaction. After fatty acid extraction with addition of 0.8 mL chloroform, 5 µL of the samples were run on a gas chromatography system (model 7890 A, Agilent Technologies) equipped with a capillary column (CP-FFAP CB; 25 m×0.15 mm×0.25 µm, Agilent Technologies). Helium was used as carrier gas; the split ratio was 50:1 and the split flow was 50 mL/min. The column temperature was kept at 100° C. for 1 min and raised to 240° C. at 10° C./min, then maintained for 17 min. The temperatures of the injector and detector were set at 250° C. and 280° C., respectively. Concentrations of fatty acids produced were calculated by peak areas calibrated with the peak area of an internal standard (nonanic acid). Butyric acid (C4) from Wako Pure Chemicals, caproic acid (C6), caprylic acid (C8), capric acid (C10), lauric acid (C12) from Tokyo Kasei were used as reference compounds for producing standard curves for these assays. A blank experiment without enzyme was used to determine autohydrolysis of substrates.

The foregoing description is considered as illustrative only of the principles of the invention. Further, since numerous modifications and changes will readily occur to those skilled in the art, it is not desired to limit the invention to the exact construction and process as described above. Accordingly, all suitable modifications and equivalents may be resorted to falling within the scope of the invention as defined by the claims that follow. The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

REFERENCES

The following references, to the extent that they provide exemplary procedural or other details supplementary to those set forth herein, are specifically incorporated herein by reference.

U.S. Pat. No. 4,554,101
U.S. Pat. No. 6,673,901
U.S. Patent Ser. 61/369,160
Bloom and Calabro, *Drug Discov Today*, 14, 949-55, 2009.
Boder and Wittrup, *Methods Enzymol.*, 328:430-444, 2000.
Bohren et al., *Protein Express. Purif.*, 54:289-294, 2007.
Brunger et al., *Acta Crystallographica*, 54:905-921, 1998.
Chang et al., *J. Biological Chem.*, 285:5266-5273, 2010.
Chupreta et al., *Molec. Cell. Biol.*, 25:4272-4282, 2005.
Clamp et al., *Bioinformatics*, 20:426-7, 2004.
Cobaugh et al., *J. Mol. Biol.*, 378:622-33, 2008.
Crooks et al., *Genome Res.*, 14:1188-90, 2004.
Current Protocols in Molecular Biology, John Wiley & Sons, 1987-1997.
Dickinson et al., *J. Molec. Biol.*, 236:1079-1092, 1994.
Duda et al., *J. Molec. Biol.*, 369:619-630, 2007.
Emsley and Cowtan, *Acta Crystallographica*, 60:2126-2132, 2004.
Erickson, *J. Muscle Res. Cell Motility*, 23(5-6):575-80, 2002.
Farmer et al., *Nature Struct. Biol.*, 3:995-997, 1996.
Fellouse et al., *J. Mol. Biol.*, 348:1153-1162, 2005.
Gallop et al., *J. Med. Chem.*, 37(9):1233-1250, 1994.
Gareau and Lima, *Nature Rev.*, 11:861-871, 2010.
Getmanova et al., *Chem Biol.*, 13, 549-56, 2006.
Hackel et al., *J. Mol. Biol.*, 381:1238-52, 2008.
Hecker et al., *J. Biol. Chem.*, 281:16117-16127, 2006.
Huang et al., *J. Molec. Biol.*, 281:61-67, 1998.
Huang et al., *Protein Expr. Purif*, 47:348-54, 2006.

Johnson, *Annual Rev. Biochem.*, 73:355-382, 2004.
Kerscher, *EMBO Repts.*, 8:550-555, 2007.
Koide and Koide, *Methods Mol. Biol.*, 352:95-109, 2007.
Koide et al., *J. Molec. Biol.*, 284:1141-1151, 1998.
Koide et al., *Proc. Natl. Acad. Sci. USA*, 104:6632-6637, 2007.
Koide et al., *Proc. Natl. Acad. Sci. USA*, 99:1253-8, 2002.
Koide et al., *Protein Eng. Des. Sel.*, 22(11):685-690, 2009.
Kontermann & Dubel, In: *Antibody Engineering: Miniantibodies*, 637-647, Springer-Verlag, 2001
Kyte and Doolittle, *J. Mol. Biol.*, 157(1):105-132, 1982.
Lawrence and Colman, *J. Molec. Biol.*, 234:946-950, 1993.
Li et al., *Oncogene*, 29:3509-3518, 2010.
Liao et al., *J. Mol. Biol.*, 284:17512-20, 2009.
Livingstone and Barton, *Comput. Appl. Biosci.*, 9:745-756, 1993.
Lo Conte et al., *J. Mol. Biol.*, 285:2177-2198, 1999.
Macauley et al., *J. Biological Chem.*, 279:49131-49137, 2004.
Mahajan et al., *Cell*, 88:97-107, 1997.
Mao and Schwarzbauer, *J. Intl. Soc. Matrix Biol.*, 24(6): 389-99, 2005.
Matunis et al., *J. Cell Biol.*, 135:1457-1470, 1996.
Minty et al., *J. Biological Chem.*, 275, 36316-36323, 2000.
Molecular Cloning, A Laboratory Manual, Second Edition, Cold Spring Harbor Laboratory Press, 1989
Murshudov et al., *Acta Crystallographica*, 53:240-255, 1997.
Olsen et al., *Nature*, 463:906-912, 2010.
Otwinowski and Minor, *Methods Enz.*, 276:307-326, 1997.
Owerbach et al., *Biochemical Biophysical Res. Comm.*, 337:517-520, 2005.
Pankov et al., *J. Cell Sci.*, 115(Pt 20):3861-3863, 2002.
Pawson and Nash, *Science*, 300:445-52, 2003.
PCT Appln. WO92/01047
Persson et al., *J. Mol. Biol.*, 357:607-20, 2006.
Reichel et al., *Analytical Chem.*, 79:8590-8600.
Reverter and Lima, *Nature*, 435:687-692, 2005.
Reynolds et al., *Bioinformatics (Oxford, England)*, 25:413-414, 2009.
Saitoh and Hinchey, *J. Biolog. Chem.*, 275:6252-6258, 2000.
Schneider and Stephens, *Nucleic Acids Res.*, 18:6097-100, 1990.
Sechler et al., *Molec. Biol. Cell*, 8(12):2563-73, 1997.
Sekiyama et al., *J. Biological Chem.*, 283:35966-35975, 2008.
Shen et al., *Nat. Struct. Mol. Biol.*, 13:1069-1077, 2006.
Sheng and Liao, *Protein Sci.*, 11:1482-1491, 2002.
Sidhu et al., *Methods Enzymol.*, 328:333-63, 2000.
Song et al., *J. Biological Chem.*, 280:40122-40129, 2005.
Song et al., *Proc. Natl. Acad. Sci. USA*, 101:14373-14378, 2004.
Steiner et al., *Nat. Biotechnol.*, 24:823-831, 2006.
Stols et al., *Protein Express. Purif.*, 53:396-403, 2007.
Studier, *Protein Express. Purif.*, 41:207-234, 2005.
Tatham and Hay, *Methods Mol. Biol.*, 497:253-268, 2009.
Tatham et al., *Nat. Struct. Mol. Biol.*, 12:67-74, 2005.
The CCP4 Suite, *Acta Crystallographica*, 50:760-763, 1994.
Vertegaal et al., *Mol. Cell Proteomics*, 5:2298-2310, 2006.
Wojcik et al., *Nat. Struct. Mol. Biol.*, 17:519-527, 2010.
Zhu et al., *J. Biological Chem.*, 283:29405-29415, 2008.
Gurung N, Ray S, Bose S, Rai V. A Broader View: Microbial Enzymes and Their Relevance in Industries, Medicine, and Beyond. BioMed Research International 2013; 2013: 1-18.
Ghaffari-Moghaddam M, Eslahi H, Omay D, Zakipour-Rahimabadi E. Industrial applications of enzymes. Review Journal of Chemistry 2014; 4(4):341-361.
Mak W S, Siegel J B. Computational enzyme design: Transitioning from catalytic proteins to enzymes. Current Opinion in Structural Biology 2014; 27:87-94.
Xiao H, Bao Z, Zhao H. High Throughput Screening and Selection Methods for Directed Enzyme Evolution. Ind Eng Chem Res 2015; 54(16):4011-4020.
Tanaka S, Takahashi T, Koide A, Ishihara S, Koikeda S, Koide S. Monobody-mediated alteration of enzyme specificity. Nat Chem Biol 2015; 11(10):762-4.
Koide A, Wojcik J, Gilbreth R N, Hoey R J, Koide S. Teaching an old scaffold new tricks: monobodies constructed using alternative surfaces of the FN3 scaffold. J Mol Biol 2012; 415(2):393-405.
Brocca S, Schmidt-Dannert C, Lotti M, Alberghina L, Schmid R D. Design, total synthesis, and functional overexpression of the *Candida rugosa* lip1 gene coding for a major industrial lipase. Protein Science: A Publication of the Protein Society 1998; 7(6):1415-1422.
Grochulski P, Li Y, Schrag J D, Bouthillier F, Smith P, Harrison D, Rubin B, Cygler M. Insights into interfacial activation from an open structure of *Candida rugosa* lipase. Journal of Biological Chemistry 1993; 268(17): 12843-7.
Grochulski P, Bouthillier F, Kazlauskas R J, Serreqi A N, Schrag J D, Ziomek E, Cygler M. Analogs of Reaction Intermediates Identify a Unique Substrate Binding Site in *Candida rugosa* Lipase. Biochemistry 1994; 33(12): 3494-3500.
Mancheño J M, Pernas MaA, Martínez MaJ, Ochoa B, Rúa M L, Hermoso J A. Structural Insights into the Lipase/esterase Behavior in the *Candida rugosa* Lipases Family: Crystal Structure of the Lipase 2 Isoenzyme at 1.97 Å Resolution. Journal of Molecular Biology 2003; 332(5): 1059-1069.
Ghosh D, Wawrzak Z, Pletnev V Z, Li N, Kaiser R, Pangborn W, Jörnvall H, Erman M, Duax W L. Structure of uncomplexed and linoleate-bound *Candida cylindracea* cholesterol esterase. Structure 1995; 3(3):279-288.
Pletnev V, Addlagatta A, Wawrzak Z, Duax W. Three-dimensional structure of homodimeric cholesterol esterase-ligand complex at 1.4 Å resolution. Acta Crystallographica Section D 2003; 59(1):50-56.
Osada K, Takahashi K, Hatano M. Polyunsaturated fatty glyceride syntheses by microbial lipases. Journal of the American Oil Chemists' Society 1990; 67(12):921-922.
Jaeger K-E, Dijkstra B W, Reetz M T. Bacterial Biocatalysts: Molecular Biology, Three-Dimensional Structures, and Biotechnological Applications of Lipases. Annual Review of Microbiology 1999; 53(1):315-351.
Hasan F, Shah A A, Hameed A. Industrial applications of microbial lipases. Enzyme and Microbial Technology 2006; 39(2):235-251.
Ishikawa K, Kataoka M, Yanamoto T, Nakabayashi M, Watanabe M, Ishihara S, Yamaguchi S. Crystal structure of beta-galactosidase from *Bacillus circulans* ATCC 31382 (BgaD) and the construction of the thermophilic mutants. FEBS J 2015; 282(13):2540-52.
Schmitt J, Brocca S, Schmid R D, Pleiss J. Blocking the tunnel: engineering of *Candida rugosa* lipase mutants with short chain length specificity. Protein Engineering 2002; 15(7):595-601.
Lee L C, Chen Y T, Yen C C, Chiang T C, Tang S J, Lee G C, Shaw J F. Altering the substrate specificity of *Candida* rugosa LIP4 by engineering the substrate-binding sites. J Agric Food Chem 2007; 55(13):5103-8.

Yen C-C, Malmis C C, Lee G-C, Lee L-C, Shaw J-F. Site-Specific Saturation Mutagenesis on Residues 132 and 450 of *Candida rugosa* LIP2 Enhances Catalytic Efficiency and Alters Substrate Specificity in Various Chain Lengths of Triglycerides and Esters. Journal of Agricultural and Food Chemistry 2010; 58(20):10899-10905.

Koide A, Bailey C W, Huang X, Koide S. The fibronectin type III domain as a scaffold for novel binding proteins1. Journal of Molecular Biology 1998; 284(4):1141-1151.

Kingsley L J, Lill M A. Substrate tunnels in enzymes: structure-function relationships and computational methodology. Proteins 2015; 83(4):599-611.

Green N M. A SPECTROPHOTOMETRIC ASSAY FOR AVIDIN AND BIOTIN BASED ON BINDING OF DYES BY AVIDIN. *Biochem J* 1965; 94:23c-24c.

Gilbreth R N, Truong K, Madu I, Koide A, Wojcik J B, Li N S, Piccirilli J A, Chen Y, Koide S. Isoform-specific monobody inhibitors of small ubiquitin-related modifiers engineered using structure-guided library design. Proceedings of the National Academy of Sciences 2011; 108(19):7751-7756.

Wojcik J, Hantschel O, Grebien F, Kaupe I, Bennett K L, Barkinge J, Jones R B, Koide A, Superti-Furga G, Koide S. A potent and highly specific FN3 monobody inhibitor of the Ab1 SH2 domain. Nat Struct Mol Biol 2010; 17(4):519-27.

Larkin M A, Blackshields G, Brown N P, Chenna R, McGettigan P A, McWilliam H, Valentin F, Wallace I M, Wilm A, Lopez R and others. Clustal W and Clustal X version 2.0. Bioinformatics 2007; 23(21):2947-8.

Goujon M, McWilliam H, Li W, Valentin F, Squizzato S, Paern J, Lopez R. A new bioinformatics analysis tools framework at EMBL-EBI. Nucleic Acids Res 2010; 38(Web Server issue):W695-9.

---

The invention claimed is:

1. A method for identifying substrate specificity modifier from a library of monobodies comprising:
   (i) contacting an enzyme with a FN3 combinatorial polypeptide library comprising a plurality of monobodies that bind different epitopes of the enzyme and are defined as having a variant fibronectin type III (FN3) domain, compared to wildtype (SEQ ID NO:91), comprising diversification in the loop regions and/or beta strand C, D, and/or F regions; and
   (ii) contacting the enzyme with an inhibitor that binds to the active site of the enzyme to form an enzyme-inhibitor complex; and
   (iii) identifying monobodies that bind to the enzyme in (i) but do not bind to the enzyme-inhibitor complex.

2. The method of claim 1, wherein identifying monobodies that modify the substrate specificity comprises identifying polypeptides that:
   a) reduce the amount of a first product of interest per unit of enzyme after a preset duration of reaction; and
   b) do not reduce the amount of a second product of interest per unit of enzyme after a preset duration of reaction.

3. The method of claim 1, wherein the monobody that modifies substrate specificity does not bind to the site of catalysis.

4. The method of claim 1, wherein the monobody that modifies substrate specificity is a polypeptide that modifies the accessibility of the active site of the enzyme.

5. The method of claim 1, wherein the monobody-enzyme complex has a level of activity that is at least 75% of the un-complexed activity level.

6. The method of claim 1, wherein the FN3 domain comprises an insertion, deletion, or substitution at one or more amino acids corresponding to position 30, 31, 33, 49, 47, 75, 76, 84, and/or 85 of SEQ ID NO:91.

7. The method of claim 1, wherein the variant FN3 domains further comprise an insertion or deletion of at least 1, 2, 3, 4, 5, 6, 7, 8, 9, 10, 15, 20, 25 amino acids in at least one loop region of FN3.

8. The method of claim 7, wherein the variant FN3 domains comprise an amino acid insertion in loop FG.

9. The method of claim 1, wherein the polypeptide library comprises a plurality of FN3 domain polypeptides comprising one or more amino acid substitutions corresponding to amino acid positions 31, 33, 47, 49, 73, and/or 75 of SEQ ID NO:91.

10. The method of claim 9, wherein the FN3 domain polypeptides further comprise one or more amino acid substitutions corresponding to amino acid positions 30, 41, 42, 43, 44, 45, 76, 77, 78, 79, 80, 81, 82, 83, 84, and/or 85 of SEQ ID NO:91.

11. The method of claim 9, wherein the FN3 domain polypeptides further comprise one or more amino acid substitutions corresponding to amino acid positions 15, 16, 17, 18, 19, 20, 21, 22, 23, 24, 25, 26, 27, 28, 29, 32, 34, 35, 36, 37, 38, 39, 40, 46, 48, 50, 51, 52, 53, 54, 55, 56, 57, 58, 59, 60, 61, 62, 63, 64, 65, 66, 67, 68, 69, 70, 72, 74, 75, 86, 87, 88, 89, 90, 91, 92, 93, and/or 94 of SEQ ID NO:91.

12. The method of claim 1, wherein the three-dimensional structure of the enzyme is unknown.

13. The method of claim 1, wherein the method further comprises masking dominant epitopes of the enzyme.

14. The method of claim 1, wherein the enzyme is a protease, peptidase, amidase, glycosidase, lipase, esterase, glycosyltransferase, hydrolase, polymerase, nuclease, nucleotide polymerase, kinase, phosphatase, methyltransferase, acetyltransferase, oxidase, dehydrogenase, peroxidase, catalase, transpeptidase, transamidase, carboxylase, gamma-glutamyltransferase, isomerase, epimerase, lyase, oxygenase, ligase, oxidoreductase, transferase, transglutaminase, protein glutaminase, amylase, deacetylase or demethylase.

* * * * *